United States Patent
Navia et al.

(10) Patent No.: US 11,752,200 B2
(45) Date of Patent: *Sep. 12, 2023

(54) METHODS OF TREATING NEUROLOGICAL DISORDERS

(71) Applicant: EnClear Therapies, Inc., Newburyport, MA (US)

(72) Inventors: Manuel A. Navia, Lexington, MA (US); Kasper Roet, Somerville, MA (US); Jonathan Fleming, Newton Lower Falls, MA (US)

(73) Assignee: EnClear Therapies Inc., Newburyport, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/153,553

(22) Filed: Jan. 20, 2021

(65) Prior Publication Data

US 2021/0145944 A1    May 20, 2021

Related U.S. Application Data

(63) Continuation of application No. PCT/US2019/042879, filed on Jul. 22, 2019.

(60) Provisional application No. 62/815,123, filed on Mar. 7, 2019, provisional application No. 62/702,191, filed on Jul. 23, 2018, provisional application No. 62/702,188, filed on Jul. 23, 2018.

(51) Int. Cl.
*A61K 38/48* (2006.01)
*G01N 33/68* (2006.01)

(52) U.S. Cl.
CPC ........ *A61K 38/4853* (2013.01); *A61K 38/486* (2013.01); *A61K 38/4826* (2013.01); *G01N 33/6896* (2013.01)

(58) Field of Classification Search
None
See application file for complete search history.

(56) References Cited

U.S. PATENT DOCUMENTS

| | | | |
|---|---|---|---|
| 3,929,992 A | 12/1975 | Sehgal et al. | |
| 4,316,885 A | 2/1982 | Rakhit | |
| 4,366,241 A | 12/1982 | Tom et al. | |
| 4,376,110 A | 3/1983 | David et al. | |
| 4,382,445 A | 5/1983 | Sommers | |
| 4,517,288 A | 5/1985 | Giegel et al. | |
| 4,650,760 A * | 3/1987 | Chlebowski | C12N 9/16 435/68.1 |
| 4,650,803 A | 3/1987 | Stella et al. | |
| 4,655,745 A | 4/1987 | Corbett | |
| 4,830,849 A | 5/1989 | Osterholm | |
| 4,837,168 A | 6/1989 | de Jaeger et al. | |
| 4,950,232 A | 8/1990 | Ruzicka et al. | |
| 5,023,263 A | 6/1991 | Von Burg | |
| 5,023,264 A | 6/1991 | Caufield et al. | |
| 5,100,883 A | 3/1992 | Schiehser | |
| 5,118,677 A | 6/1992 | Caufield | |
| 5,118,678 A | 6/1992 | Kao et al. | |
| 5,120,842 A | 6/1992 | Failli et al. | |
| 5,130,307 A | 7/1992 | Failli et al. | |
| 5,162,333 A | 11/1992 | Failli et al. | |
| 5,177,203 A | 1/1993 | Failli et al. | |
| 5,221,670 A | 6/1993 | Caufield | |
| 5,233,036 A | 8/1993 | Hughes | |
| 5,256,790 A | 10/1993 | Nelson | |
| 5,258,389 A | 11/1993 | Goulet et al. | |
| 5,260,300 A | 11/1993 | Hu | |
| 5,262,423 A | 11/1993 | Kao | |
| 5,302,584 A | 4/1994 | Kao et al. | |
| 5,362,718 A | 11/1994 | Skotnicki et al. | |
| 5,373,014 A | 12/1994 | Failli et al. | |
| 5,378,836 A | 1/1995 | Kao et al. | |
| 5,385,908 A | 1/1995 | Nelson et al. | |
| 5,385,909 A | 1/1995 | Nelson et al. | |
| 5,385,910 A | 1/1995 | Ocain et al. | |
| 5,389,639 A | 2/1995 | Failli et al. | |
| 5,391,730 A | 2/1995 | Skotnicki et al. | |
| 5,405,316 A | 4/1995 | Magram | |
| 5,411,967 A | 5/1995 | Kao et al. | |
| 5,434,260 A | 7/1995 | Skotnicki et al. | |
| 5,463,048 A | 10/1995 | Skotnicki et al. | |
| 5,480,988 A | 1/1996 | Failli et al. | |
| 5,480,989 A | 1/1996 | Kao et al. | |
| 5,489,680 A | 2/1996 | Failli et al. | |
| 5,491,231 A | 2/1996 | Nelson et al. | |
| 5,504,091 A | 4/1996 | Molnar-Kimber et al. | |
| 5,531,673 A | 7/1996 | Helenowski | |

(Continued)

FOREIGN PATENT DOCUMENTS

| | | |
|---|---|---|
| WO | 98/02441 A2 | 1/1998 |
| WO | 99/15530 A1 | 4/1999 |

(Continued)

OTHER PUBLICATIONS

Paraskevas "The emerging TDP-43 proteinopathy" Neuroimmunol Neuroinflammation 5:17 (Year: 2018).*
Bioline "Proteinase K" accessed from bioline.com on Jun. 22, 2021 (Year: 2013).*
Thermo "immobilized trypsin, TPCK treated (agarose resin)" accessed from thermofisher.com on May 4, 2022 (Year: 2015).*
Arriagada, P., et al., "Neurofibrillary tangles but not senile plaques parallel duration and severity of Alzheimer's disease," Neurology 42, 1992, pp. 631-639.
Asai, D., et al., "Chapter 3 Making Monoclonal Antibodies," Methods in Cell Biology, vol. 37, 1993, pp. 57-74.

(Continued)

*Primary Examiner* — Adam Weidner
(74) *Attorney, Agent, or Firm* — Nutter McClennen & Fish LLP

(57) ABSTRACT

Disclosed is a method for treating a subject having a neurological disorder characterized by the presence of toxic proteins comprising contacting the cerebrospinal fluid (CSF) of the subject with an agent capable of removing or degrading the toxic protein.

8 Claims, 8 Drawing Sheets

Specification includes a Sequence Listing.

(56) References Cited

U.S. PATENT DOCUMENTS

| | | | |
|---|---|---|---|
| 5,563,145 A | 10/1996 | Failli et al. | |
| 5,665,772 A | 9/1997 | Cottens et al. | |
| 5,780,462 A | 7/1998 | Lee et al. | |
| 5,957,912 A | 9/1999 | Heitzmann | |
| 6,193,691 B1 | 2/2001 | Beardsley | |
| 6,210,346 B1 | 4/2001 | Hall et al. | |
| 6,273,913 B1 | 8/2001 | Wright et al. | |
| 6,277,983 B1 | 8/2001 | Shaw et al. | |
| 6,358,969 B1 | 3/2002 | Shelley et al. | |
| 6,471,960 B1 | 10/2002 | Anderson | |
| 6,585,764 B2 | 7/2003 | Wright et al. | |
| 6,599,275 B1 | 7/2003 | Fischer, Jr. | |
| 6,670,168 B1 | 12/2003 | Katz et al. | |
| 6,689,085 B1 | 2/2004 | Rubenstein et al. | |
| 6,696,488 B2 | 2/2004 | Wolfe et al. | |
| 6,808,536 B2 | 10/2004 | Wright et al. | |
| 7,025,739 B2 | 4/2006 | Saul | |
| 7,037,288 B2 | 5/2006 | Rosenberg et al. | |
| 7,717,871 B2 | 5/2010 | Odland | |
| 7,763,142 B2 | 7/2010 | Watson | |
| 7,887,503 B2 | 2/2011 | Geiger | |
| 8,206,334 B2 | 6/2012 | Kralick et al. | |
| 8,216,173 B2 | 7/2012 | Dacey, Jr. et al. | |
| 8,292,856 B2 | 10/2012 | Bertrand et al. | |
| 8,435,204 B2 | 5/2013 | Lad et al. | |
| 9,097,723 B2 * | 8/2015 | Fathollahi | G01N 33/6842 |
| 9,421,348 B2 | 8/2016 | Lenihan et al. | |
| 9,603,792 B2 | 3/2017 | John | |
| 9,629,987 B2 | 4/2017 | Anand et al. | |
| 9,687,670 B2 | 6/2017 | Dacey, Jr. et al. | |
| 9,744,338 B2 | 8/2017 | East et al. | |
| 9,770,180 B2 | 9/2017 | Radojicic | |
| 9,895,518 B2 | 2/2018 | Lad et al. | |
| 9,919,138 B2 | 3/2018 | Lenihan et al. | |
| 10,258,781 B2 | 4/2019 | Choi et al. | |
| 10,272,188 B1 | 4/2019 | Geiger et al. | |
| 2002/0025521 A1 | 2/2002 | Lu et al. | |
| 2003/0135148 A1 | 7/2003 | Dextradeur et al. | |
| 2004/0068241 A1 | 4/2004 | Fischer | |
| 2004/0110250 A1 | 6/2004 | Wischik et al. | |
| 2004/0138153 A1 | 7/2004 | Ramesh et al. | |
| 2004/0185042 A1 * | 9/2004 | Scheiflinger | C12Q 1/56 424/140.1 |
| 2004/0220510 A1 | 11/2004 | Koullick et al. | |
| 2004/0236309 A1 | 11/2004 | Yang | |
| 2006/0025726 A1 | 2/2006 | Fischer et al. | |
| 2006/0079740 A1 | 4/2006 | Silver et al. | |
| 2007/0167867 A1 | 7/2007 | Wolf | |
| 2007/0173787 A1 | 7/2007 | Huang et al. | |
| 2007/0243179 A1 | 10/2007 | Elia | |
| 2008/0082036 A1 | 4/2008 | Trescony et al. | |
| 2008/0242590 A1 | 10/2008 | Andersson et al. | |
| 2010/0030196 A1 | 2/2010 | Hildebrand et al. | |
| 2010/0234792 A1 | 9/2010 | Dacey, Jr. et al. | |
| 2011/0033463 A1 | 2/2011 | Thakker et al. | |
| 2012/0238835 A1 | 9/2012 | Hyde et al. | |
| 2012/0238936 A1 | 9/2012 | Hyde et al. | |
| 2013/0273203 A1 * | 10/2013 | Oestergaard | A23L 33/18 435/213 |
| 2014/0018257 A1 | 1/2014 | Suga et al. | |
| 2014/0206102 A1 | 7/2014 | Petrucelli et al. | |
| 2014/0303455 A1 | 10/2014 | Shachar et al. | |
| 2014/0377319 A1 | 12/2014 | Leuthardt et al. | |
| 2015/0374898 A1 | 12/2015 | Fujieda et al. | |
| 2016/0002627 A1 | 1/2016 | Bennett et al. | |
| 2016/0025747 A1 | 1/2016 | Ranum et al. | |
| 2016/0089521 A1 | 3/2016 | Dragoon et al. | |
| 2016/0361365 A1 | 12/2016 | Lee et al. | |
| 2017/0059586 A1 | 3/2017 | Petrucelli et al. | |
| 2017/0137492 A1 * | 5/2017 | Looby | A61P 3/04 |
| 2017/0157038 A1 | 6/2017 | Peyman | |
| 2017/0157374 A1 | 6/2017 | Hedstrom et al. | |
| 2017/0313687 A1 | 11/2017 | Hendrickson et al. | |
| 2018/0028746 A1 | 2/2018 | Abrams et al. | |
| 2018/0185058 A1 | 7/2018 | Anand et al. | |
| 2018/0371010 A1 * | 12/2018 | Vassylyev | C12N 15/62 |
| 2019/0009014 A1 | 1/2019 | Chen et al. | |
| 2019/0048371 A1 | 2/2019 | Basheer et al. | |
| 2019/0089521 A1 | 3/2019 | Coulthard et al. | |
| 2019/0317099 A1 | 10/2019 | Halbert et al. | |
| 2020/0046954 A1 | 2/2020 | Lad et al. | |
| 2020/0330497 A1 | 10/2020 | Marcotulli et al. | |
| 2021/0023293 A1 | 1/2021 | DePasqua et al. | |
| 2021/0033620 A1 * | 2/2021 | Porter | G01N 33/581 |
| 2021/0154276 A1 | 5/2021 | Navia et al. | |

FOREIGN PATENT DOCUMENTS

| | | |
|---|---|---|
| WO | 2000/056335 A1 | 9/2000 |
| WO | 01/14387 A1 | 3/2001 |
| WO | 03/057218 A1 | 7/2003 |
| WO | 2003/015710 A3 | 2/2004 |
| WO | 2004/058337 A1 | 7/2004 |
| WO | 2004/091444 A2 | 10/2004 |
| WO | 2008/105959 A2 | 9/2008 |
| WO | 2011114260 A1 | 9/2011 |
| WO | 2014/124365 A2 | 8/2014 |
| WO | 2014/159247 A1 | 10/2014 |
| WO | 2015/049588 A2 | 4/2015 |
| WO | 2017096228 A1 | 6/2017 |
| WO | 2018005621 A1 | 1/2018 |
| WO | 2020/023417 A1 | 1/2020 |
| WO | 2020/023418 A1 | 1/2020 |

OTHER PUBLICATIONS

Dejesus-Hernandez, M., et al., "Expanded GGGGCC Hexanucleotide Repeat in Noncoding Region of C9ORF72 Causes Chromosome 9p-Linked FTD and ALS," Neuron, vol. 72, 2011, pp. 245-256.

Giannakopoulos, P., et al., Tangle and neuron numbers, but not amyloid load, predict cognitive status in Alzheimer's disease, Neurology, vol. 60, 2003, pp. 1495-1500.

Gomez-Isla, T., et al., Neuronal loss correlates with but exceeds neurofibrillary tangles in Alzheimer's disease, Annals of Neurology, vol. 41, 1997, pp. 17-24.

Graff-Radford, N., et al., "Frontotemporal dementia," Seminars in Neurology vol. 27, 2007, pp. 48-57.

Hasegawa, M., et al., "Phosphorylated TDP-43 in frontotemporal lobar degeneration and amyotrophic lateral sclerosis," Annals of Neurology, vol. 62, Issue 1, 2008, pp. 60-70.

Lomen-Hoerth, C., et al., "The overlap of amyotrophic lateral sclerosis and frontotemporal dementia," Neurology, vol. 59, 2002, pp. 1077-1079.

Marx, S., et al., "Bench to Bedside: The Development of Rapamycin and Its Application to Stent Restenosis", Journal of the American Heart Association 104, 2001, pp. 852-855.

Paulson, H., et al., "Genetics of Dementia," Seminars in Neurology, vol. 31, 2011, pp. 449-460.

Poreba, M., et al., "Current Strategies for Probing Substrate Specificity of Proteases," Current Medicinal Chemistry, vol. 17, Issue 33, 2010, pp. 3968-3995.

Quinn, J., et al., "Tau Proteolysis in the Pathogenesis of Tauopathies: Neurotoxic Fragments and Novel Biomarkers," Journal of Alzheimer's Disease, vol. 63, No. 1, 2018, pp. 13-33.

Steele, J., et al., "Progressive Supranuclear Palsy A Heterogeneous Degeneration Involving the Brain Stem, Basal Ganglia and Cerebellum With Vertical Gaze and Pseudobulbar Palsy, Nuchal Dystonia and Dementia," Arch Neurol. vol. 10, No. 4, 1964, pp. 333-359.

Arai, T., et al., "TDP-43 is a component of ubiquitin-positive tau-negative inclusions in frontotemporal lobar degeneration and amyotrophic lateral sclerosis," Biochemical and Biophysical Research Communications, vol. 351, Issue 3, 2006, pp. 602-611.

Arai, T., et al., "Phosphorylated and cleaved TDP?43 in ALS, FTLD and other neurodegenerative disorders and in cellular models of TDP-43 proteinopathy," Neuropathology, vol. 30, 2010, pp. 170-181.

Andersen, P., et al., "Clinical genetics of amyotrophic lateral sclerosis: what do we really know?" Nature Reviews Neurology, vol. 7, 2011, pp. 603-615.

(56) References Cited

OTHER PUBLICATIONS

Brat, D., et al., "Tau-associated neuropathology in ganglion cell tumours increases with patient age but appears unrelated to ApoE genotype," Neuropathy and Applied Neurobiology, vol. 27, Issue 3, 2001, pp. 197-205.

Buee, L., et al., "Tau protein isoforms, phosphorylation and role in neurodegenerative disorders," Brain Research Reviews, vol. 33, Issue 1, 2000, pp. 95-130.

Chang, Y., et al., "The Glycine-Alanine Dipeptide Repeat from C9orf72 Hexanucleotide Expansions Forms Toxic Amyloids Possessing Cell-to-Cell Transmission Properties" Journal of Biological Chemistry, vol. 291, Issue 10, 2016, pp. 4903-4911.

Coatti, G., et al., "Pericytes Extended Survival of ALS SOD1 Mice and Induce the Expression of Antioxidant Enzymes in the Murine Model and in IPSCs Derived Neuronal Cells from an ALS Patient," Stem Cell Reviews and Reports, 2017, 13, pp. 686-698.

De Souza, P., et al., "A biotechnology perspective of fungal proteases," Brazilian Journal of Microbiology, vol. 46, 2, 2015, pp. 337-346.

Diamond, S., "Methods for mapping protease specificity," Current Opinion in Chemical Biology, vol. 11, Issue 1, 2007, pp. 46-51.

Evidente, V., et al., "Post-encephalitic parkinsonism,"Journal of Neurology, Neurosurgery & Psychiatry, vol. 63, Issue 1, 1998, pp. 5.

Grad, L., et al., "Prion-like activity of Cu/Zn superoxide dismutase: implications for amyotrophic lateral sclerosis," 8:1, 2014, pp. 33-41.

Giordana, M., et al., "Dementia and cognitive impairment in amyotrophic lateral sclerosis: a review," Neurological Sciences, vol. 32, 2011, pp. 9-16.

Hasegawa, M., et al., "Molecular Dissection of TDP-43 Proteinopathies," Journal of Molecular Neuroscience, vol. 45, 2011, pp. 480-485.

International Search Report and Written Opinion for International Application No. PCT/US2019/042880, dated Oct. 16, 2019 (10 pages).

International Search Report and Written Opinion for International Application No. PCT/US2019/042879, dated Oct. 8, 2019 (14 pages).

International Search Report and Written Opinion for International Application No. PCT/US2020/027683, dated Aug. 6, 2020 (19 pages).

International Preliminary Report on Patentability for International Application No. PCT/US2019/042880, dated Jan. 12, 2021 (8 pages).

Written Opinion of the International Preliminary Examining Authority for International Application No. PCT/US2019/042879, dated Feb. 25, 2021 (6 pages).

Written Opinion of the International Preliminary Examining Authority for International Application No. PCT/US2019/042880, dated Sep. 11, 2020 (8 pages).

Kaufman, S., et al., "Prion-Like Propagation of Protein Aggregation and Related Therapeutic Strategies," Neurotherapeutics, 10, 2013, pp. 371-382.

Kopeikina, K., et al., "Soluble forms of tau are toxic in Alzheimer's disease," Translational Neuroscience 3(3), 2012, pp. 223-233.

Kouzehgarani, G., et al., "Harnessing cerebrospinal fluid circulation for drug delivery to brain tissues," Advanced Drug Delivery Reviews, 2021, vol. 173, pp. 20-59.

Lee, V., et al., "Neurodegenerative tauopathies," Annual Review of Neuroscience, vol. 24, 2001, pp. 1121-1159.

Lei, P., et al., "Tau protein: relevance to Parkinson's disease," The International Journal of Biochemistry & Cell Biology, vol. 42, Issue 11, 2010, pp. 1775-1778.

Martin, L., et al., "Post-translational modifications of tau protein: Implications for Alzheimer's disease," Neurochemistry International, vol. 58, Issue 4, 2011, pp. 458-471.

May, S., et al., "C9orf72 FTLD/ALS—associated Gly-Ala dipeptide repeat proteins cause neuronal toxicity and Unc119 sequestration," Acta Neuropathologica, vol. 128, 2014, pp. 485-503.

McKee, A., et al., "The Neuropathology of Chronic Traumatic Encephalopathy," Brain Pathology 25, 2015, pp. 350-364.

McRae, B., et al., Mapping the active sites of bovine thrombin, factor IXa, factor Xa, factor XIa, factor XIIa, plasma kallikrein, and trypsin with amino acid and peptide thioesters: development of new sensitive substrates. Biochemistry 1981, 20, 25, pp. 7196-7206.

Narasimhan, S., et al., "Pathological Tau Strains from Human Brains Recapitulate the Diversity of Tauopathies in Nontransgenic Mouse Brain," The Jorunal of Neuroscience, vol. 37, Issue 47, 2017, pp. 11406-11423.

Neumann, M., et al., "Ubiquitinated TDP-43 in frontotemporal lobar degeneration and amyotrophic lateral sclerosis," Science, vol. 314, 2006, pp. 130-133.

Ohki, Y., et al., "Glycine-alanine dipeptide repeat protein contributes to toxicity in a zebrafish model of C9orf72 associated neurodegeneration," Molecular Neurodegeneration (2017) 12:6, pp. 1-11.

Phukan, J., et al., "Cognitive impairment in amyotrophic lateral sclerosis," The Lancet Neurology, 2007, vol. 6, Issue 11, pp. 994-1003.

Renton, A., et al., "A Hexanucleotide Repeat Expansion in C9ORF72 is the Cause of Chromosome 9p21-Linked ALS-FTD," Neuron vol. 72, Issue 2, 2011, pp. 257-268.

Westergard, T., et al., "Cell-to-Cell Transmission of Dipeptide Repeat Proteins Linked to C9orf72-ALS/FTD," Cell Reports, 2016, vol. 17, pp. 645-652.

Wray, S., et al., "Direct analysis of tau from PSP brain identifies new phosphorylation sites and a major fragment of N-terminally cleaved tau containing four microtubule-binding repeats," Journal of Neurochemistry, vol. 105, 2008, pp. 2343-2352.

Wszolek, Z., et al., "Frontotemporal dementia and parkinsonism linked to chromosome 17 (FTDP-17)" Orphanet Journal of Rare Diseases, 2006, 1:30, pp. 1-9.

Zhang, Y., et al., "Aggregation-prone c9FTD/ALS poly(GA) RAN—translated proteins cause neurotoxicity by inducing ER stress," Acta Neuropathologica, vol. 128, 2014, pp. 504-524.

Abbott, N., et al., "The role of brain barriers in fluid movement in the CNS: is there a 'glymphatic' system?" Acta Neuropathologica vol. 135, 2018, pp. 387-407.

Allen, J., et al., "Abstract 3483: Modeling circulating tumor cells in the peripheral blood and CSF of breast cancer patients," Cancer Research vol. 73, Issue 8, 2013, abstract only.

Allen, J., et al., "Abstract 5565: Circulating tumor cells in the peripheral blood and cerebrospinal fluid of patients with central nervous system metastases," Cancer Research vol. 72, Issue 8, 2012, abstract only.

Finsterer, J., et al., "Liquorpheresis (CSF filtration) in familial amyotrophic lateral sclerosis," Spinal Cord, vol. 39, 1999, pp. 592-593.

Hersh, D., et al., "MR-guided transcranial focused ultrasound safely enhances interstitial dispersion of large polymeric nanoparticles in the living brain," Plos One 13(2): e0192240, 2018, 19 pages.

Indivero, V., "Technique filters cancer where chemo can't reach: A new therapy may help cancer patients with malignant cells near the spinal cord and in the brain," dated Jul. 30, 2013. Retrieved from the internet under https://news.psu.edu/story/282970/2013/07/30/research/technique-filters-cancer-where-chemo-cant-reach, 4 pages.

International Search Report and Written Opinion for International Application No. PCT/US2021/013458, dated Jun. 9, 2021 (20 pages).

Jessen, N., et al., "The Glymphatic System—A Beginner's Guide," Neurochemical Research, 2015, 40(2), pp. 2583-2599.

Legon, W., et al., "Transcranial focused ultrasound modulates the activity of primary somatosensory cortex in humans," Nature Neuroscience vol. 17, No. 2, 2014, pp. 322-329.

Lipsman, N., et al., "Blood-brain barrier opening in Alzheimer's disease using MR-guided focused ultrasound," Nature Communications vol. 9, Article 2336, 2018, pp. 1-8.

Menendez-Gonzalez, M., et al., "Targeting Beta-Amyloid at the CSF: A New Therapeutic Strategy in Alzheimer's Disease," Frontiers in Aging Neuroscience, vol. 10, 2018, pp. 1-8.

Ozcelik, A., et al., "Acoustic tweezers for the life sciences," Nature Methods vol. 15, 2018, pp. 1021-1028.

Pardridge, W., et al., "CSF, blood-brain barrier, and brain drug delivery," Expert Opinion on Drug Delivery, vol. 13, 2016, pp. 1-13.

(56) References Cited

OTHER PUBLICATIONS

Patel, A., et al., "Identification and enumeration of circulating tumor cells in the cerebrospinal fluid of breast cancer patients with central nervous system metastases," Oncotarget, vol. 2, No. 10, 2011, pp. 752-760.

Reinhard, M., et al., "Blood-Brain Barrier Disruption by Low-Frequency Ultrasound," Stroke, vol. 37, 2006, pp. 1546-1548.

Sonabend, A., et al., "Overcoming the Blood-Brain Barrier with an Implantable Ultrasound Device," Clinical Cancer Research, vol. 25, Issue 13, 2019, pp. 3750-3752.

Song, J., et al., "Investigation of standing wave formation in a human skull for a clinical prototype of a large-aperture, transcranial MR-guided Focused Ultrasound (MRgFUS) phased array: An experimental and simulation study," IEEE Transactions on Biomedical Engineering, vol. 59, Issue 2, 2012, pp. 435-444.

Takalo, M., et al., "Protein aggregation and degradation mechanisms in neurodegenerative diseases," American Journal of Neurodegenerative Disease, 2013; 2(1), pp. 1-14.

Tarasoff-Conway, J., et al., "Clearance systems in the brain—implications for Alzheimer disease," Nature Reviews Neurology 11(8), 2015, pp. 457-470.

Tyler, W., et al., "Remote Excitation of Neuronal Circuits Using Low-Intensity, Low-Frequency Ultrasound," PLOS ONE vol. 3, Issue 10, 2008, e3511, 11 pages.

Xie, L., et al., "Sleep Drives Metabolite Clearance from the Adult Brain," Science vol. 342, Issue 6156, 2013, pp. 373-377.

International Preliminary Report on Patentability for International Application No. PCT/US2020/027683, dated Oct. 21, 2021 (11 pages).

Lin et al., Facile synthesis of enzyme—inorganic hybrid nanoflowers and their application as an immobilized trypsin reactor for highly efficient protein digestion (Communication) RSC Adv., 2014, 4, pp. 13888-13891.

Spencer, B., et al., "Lentivirus Mediated Delivery of Neurosin Promotes Clearance of Wild-type α-Synuclein and Reduces the Pathology in an α-Synuclein Model of LBD", Molecular Therapy, vol. 21, No. 1, Jan. 1, 2013, pp. 31-41.

Extended European Search Report for European Application No. 19839881.0 dated Jun. 21, 2022, 9 pages.

Extended European Search Report for European Application No. 19840444.4 dated Jun. 28, 2022, 7 pages.

Kim Kwang Soo, et al., "Proteolytic Cleavage of Extracellular α-Synuclein by Plasmin: Implications for Parkinson Disease" Journal of Biological Chemistry, vol. 287, No. 30, Mar. 22, 2012, pp. 24862-24872.

Miori, K., et al., "The C9orf72 GGGGCC repeat is translated into aggregating dipeptide-repeat proteins in FTLD/ALS," Science, vol. 339, No. 6125, Feb. 7, 2013, pp. 1335-1338.

Saido, T., et al., "Proteolytic Degradation of Amyloid β—Protein" Cold Spring Harbor Perspectives in Medicine, vol. 2, No. 6, Jun. 1, 2012, pp. a006379-a006379.

Tanji, K., et al., "Proteinase K-resistant α-synuclein is deposited in presynapses in human Lewy body disease and A53T α-synuclein transgenic mice," Acta Neuropathologica, Springer, Berlin, DE, vol. 120, No. 2, Mar. 26, 2010, pp. 145-154.

\* cited by examiner

SEQUENCE LISTING

<160> NUMBER OF SEQ ID NOS: 13

<210> SEQ ID NO 1
<211> LENGTH: 224
<212> TYPE: PRT
<213> ORGANISM: Bos taurus

<400> SEQUENCE: 1

```
Ile Val Gly Gly Tyr Thr Cys Ala Glu Asn Ser Val Pro Tyr Gln Val
1               5                   10                  15

Ser Leu Asn Ala Gly Tyr His Phe Cys Gly Gly Ser Leu Ile Asn Asp
            20                  25                  30

Gln Trp Val Val Ser Ala Ala His Cys Tyr Gln Tyr His Ile Gln Val
        35                  40                  45

Arg Leu Gly Glu Tyr Asn Ile Asp Val Leu Glu Gly Gly Glu Gln Phe
    50                  55                  60

Ile Asp Ala Ser Lys Ile Ile Arg His Pro Lys Tyr Ser Ser Trp Thr
65                  70                  75                  80

Leu Asp Asn Asp Ile Leu Leu Ile Lys Leu Ser Thr Pro Ala Val Ile
                85                  90                  95

Asn Ala Arg Val Ser Thr Leu Leu Leu Pro Ser Ala Cys Ala Ser Ala
            100                 105                 110

Gly Thr Glu Cys Leu Ile Ser Gly Trp Gly Asn Thr Leu Ser Ser Gly
        115                 120                 125

Val Asn Tyr Pro Asp Leu Leu Gln Cys Leu Val Ala Pro Leu Leu Ser
    130                 135                 140

His Ala Asp Cys Glu Ala Ser Tyr Pro Gly Gln Ile Thr Asn Asn Met
145                 150                 155                 160

Ile Cys Ala Gly Phe Leu Glu Gly Gly Lys Asp Ser Cys Gln Gly Asp
                165                 170                 175

Ser Gly Gly Pro Val Ala Cys Asn Gly Gln Leu Gln Gly Ile Val Ser
            180                 185                 190

Trp Gly Tyr Gly Cys Ala Gln Lys Gly Lys Pro Gly Val Tyr Thr Lys
        195                 200                 205
```

```
Val Cys Asn Tyr Val Asp Trp Ile Gln Glu Thr Ile Ala Ala Asn Ser
    210                 215                 220
```

<210> SEQ ID NO 2
<211> LENGTH: 224
<212> TYPE: PRT
<213> ORGANISM: Homo sapiens

<400> SEQUENCE: 2

```
Ile Val Gly Gly Tyr Thr Cys Glu Glu Asn Ser Val Pro Tyr Gln Val
1               5                   10                  15

Ser Leu Asn Ser Gly Ser His Phe Cys Gly Gly Ser Leu Ile Ser Glu
            20                  25                  30

Gln Trp Val Val Ser Ala Gly His Cys Tyr Lys Pro His Ile Gln Val
        35                  40                  45

Arg Leu Gly Glu His Asn Ile Glu Val Leu Gly Asn Glu Gln Phe
    50                  55                  60

Ile Asn Ala Ala Lys Ile Ile Arg His Pro Lys Tyr Asn Arg Ile Thr
65                  70                  75                  80

Leu Asn Asn Asp Ile Met Leu Ile Lys Leu Ser Thr Pro Ala Val Ile
                85                  90                  95

Asn Ala His Val Ser Thr Ile Ser Leu Pro Thr Ala Pro Pro Ala Ala
                100                 105                 110

Gly Thr Glu Cys Leu Ile Ser Gly Trp Gly Asn Thr Leu Ser Ser Gly
            115                 120                 125

Ala Asp Tyr Pro Asp Glu Leu Gln Cys Leu Asp Ala Pro Val Leu Thr
    130                 135                 140

Gln Ala Lys Cys Lys Ala Ser Tyr Pro Leu Lys Ile Thr Ser Lys Met
145                 150                 155                 160

Phe Cys Val Gly Phe Leu Glu Gly Gly Lys Asp Ser Cys Gln Gly Asp
                165                 170                 175

Ser Gly Gly Pro Val Val Cys Asn Gly Gln Leu Gln Gly Ile Val Ser
            180                 185                 190

Trp Gly Tyr Gly Cys Ala Gln Lys Arg Arg Pro Gly Val Tyr Thr Lys
        195                 200                 205

Val Tyr Asn Tyr Val Asp Trp Ile Lys Asp Thr Ile Ala Ala Asn Ser
    210                 215                 220
```

<210> SEQ ID NO 3
<211> LENGTH: 224
<212> TYPE: PRT
<213> ORGANISM: Homo sapiens

<400> SEQUENCE: 3

```
Ile Val Gly Gly Tyr Asn Cys Glu Glu Asn Ser Val Pro Tyr Gln Val
1               5                   10                  15

Ser Leu Asn Ser Gly Tyr His Phe Cys Gly Gly Ser Leu Ile Asn Glu
            20                  25                  30

Gln Trp Val Val Ser Ala Gly His Cys Tyr Lys Ser Arg Ile Gln Val
        35                  40                  45

Arg Leu Gly Glu His Asn Ile Glu Val Leu Gly Asn Glu Gln Phe
    50                  55                  60

Ile Asn Ala Ala Lys Ile Ile Arg His Pro Gln Tyr Asp Arg Lys Thr
65                  70                  75                  80

Leu Asp Asn Asp Ile Leu Leu Ile Lys Leu Ser Ser Pro Ala Val Ile
                85                  90                  95
```

```
Asn Ser Arg Val Ser Ala Ile Ser Leu Pro Thr Ala Pro Ala Ala
            100                 105                 110

Gly Thr Glu Ser Leu Ile Ser Gly Trp Gly Asn Thr Leu Ser Ser Gly
            115                 120                 125

Ala Asp Tyr Pro Asp Glu Leu Gln Cys Leu Asp Ala Pro Val Leu Ser
        130                 135                 140

Gln Ala Glu Cys Glu Ala Ser Tyr Pro Gly Lys Ile Thr Asn Asn Met
145                 150                 155                 160

Phe Cys Val Gly Phe Leu Glu Gly Gly Lys Asp Ser Cys Gln Gly Asp
                165                 170                 175

Ser Gly Gly Pro Val Val Ser Asn Gly Glu Leu Gln Gly Ile Val Ser
            180                 185                 190

Trp Gly Tyr Gly Cys Ala Gln Lys Asn Arg Pro Gly Val Tyr Thr Lys
            195                 200                 205

Val Tyr Asn Tyr Val Asp Trp Ile Lys Asp Thr Ile Ala Ala Asn Ser
        210                 215                 220
```

```
<210> SEQ ID NO 4
<211> LENGTH: 240
<212> TYPE: PRT
<213> ORGANISM: Sus scrofa

<400> SEQUENCE: 4

Val Val Gly Gly Thr Glu Ala Gln Arg Asn Ser Trp Pro Ser Gln Ile
1               5                   10                  15

Ser Leu Gln Tyr Arg Ser Gly Ser Ser Trp Ala His Thr Cys Gly Gly
            20                  25                  30

Thr Leu Ile Arg Gln Asn Trp Val Met Thr Ala Ala His Cys Val Asp
        35                  40                  45

Arg Glu Leu Thr Phe Arg Val Val Val Gly Glu His Asn Leu Asn Gln
    50                  55                  60

Asn Asn Gly Thr Glu Gln Tyr Val Gly Val Gln Lys Ile Val Val His
65                  70                  75                  80

Pro Tyr Trp Asn Thr Asp Asp Val Ala Ala Gly Tyr Asp Ile Ala Leu
                85                  90                  95

Leu Arg Leu Ala Gln Ser Val Thr Leu Asn Ser Tyr Val Gln Leu Gly
            100                 105                 110

Val Leu Pro Arg Ala Gly Thr Ile Leu Ala Asn Asn Ser Pro Cys Tyr
        115                 120                 125

Ile Thr Gly Trp Gly Leu Thr Arg Thr Asn Gly Gln Leu Ala Gln Thr
    130                 135                 140

Leu Gln Gln Ala Tyr Leu Pro Thr Val Asp Tyr Ala Ile Cys Ser Ser
145                 150                 155                 160

Ser Ser Tyr Trp Gly Ser Thr Val Lys Asn Ser Met Val Cys Ala Gly
                165                 170                 175

Gly Asp Gly Val Arg Ser Gly Cys Gln Gly Asp Ser Gly Gly Pro Leu
            180                 185                 190

His Cys Leu Val Asn Gly Gln Tyr Ala Val His Gly Val Thr Ser Phe
        195                 200                 205

Val Ser Arg Leu Gly Cys Asn Val Thr Arg Lys Pro Thr Val Phe Thr
    210                 215                 220

Arg Val Ser Ala Tyr Ile Ser Trp Ile Asn Asn Val Ile Ala Ser Asn
225                 230                 235                 240
```

```
<210> SEQ ID NO 5
```

```
<211> LENGTH: 240
<212> TYPE: PRT
<213> ORGANISM: Homo sapiens

<400> SEQUENCE: 5

Val Val Gly Gly Thr Glu Ala Gly Arg Asn Ser Trp Pro Ser Gln Ile
1               5                   10                  15

Ser Leu Gln Tyr Arg Ser Gly Ser Arg Tyr His Thr Cys Gly Gly
            20                  25                  30

Thr Leu Ile Arg Gln Asn Trp Val Met Thr Ala Ala His Cys Val Asp
            35                  40                  45

Tyr Gln Lys Thr Phe Arg Val Val Ala Gly Asp His Asn Leu Ser Gln
    50                  55                  60

Asn Asp Gly Thr Glu Gln Tyr Val Ser Val Gln Lys Ile Val Val His
65                  70                  75                  80

Pro Tyr Trp Asn Ser Asp Asn Val Ala Ala Gly Tyr Asp Ile Ala Leu
                85                  90                  95

Leu Arg Leu Ala Gln Ser Val Thr Leu Asn Ser Tyr Val Gln Leu Gly
            100                 105                 110

Val Leu Pro Gln Glu Gly Ala Ile Leu Ala Asn Asn Ser Pro Cys Tyr
        115                 120                 125

Ile Thr Gly Trp Gly Lys Thr Lys Thr Asn Gly Gln Leu Ala Gln Thr
130                 135                 140

Leu Gln Gln Ala Tyr Leu Pro Ser Val Asp Tyr Ala Ile Cys Ser Ser
145                 150                 155                 160

Ser Ser Tyr Trp Gly Ser Thr Val Lys Asn Thr Met Val Cys Ala Gly
                165                 170                 175

Gly Asp Gly Val Arg Ser Gly Cys Gln Gly Asp Ser Gly Gly Pro Leu
            180                 185                 190

His Cys Leu Val Asn Gly Lys Tyr Ser Val His Gly Val Thr Ser Phe
        195                 200                 205

Val Ser Ser Arg Gly Cys Asn Val Ser Arg Lys Pro Thr Val Phe Thr
    210                 215                 220

Gln Val Ser Ala Tyr Ile Ser Trp Ile Asn Asn Val Ile Ala Ser Asn
225                 230                 235                 240

<210> SEQ ID NO 6
<211> LENGTH: 241
<212> TYPE: PRT
<213> ORGANISM: Homo sapiens

<400> SEQUENCE: 6

Val Val Gly Gly Glu Glu Ala Arg Pro Asn Ser Trp Pro Trp Gln Val
1               5                   10                  15

Ser Leu Gln Tyr Ser Ser Asn Gly Lys Trp Tyr His Thr Cys Gly Gly
            20                  25                  30

Ser Leu Ile Ala Asn Ser Trp Val Leu Thr Ala Ala His Cys Ile Ser
            35                  40                  45

Ser Ser Arg Thr Tyr Arg Val Gly Leu Gly Arg His Asn Leu Tyr Val
    50                  55                  60

Ala Glu Ser Gly Ser Leu Ala Val Ser Val Ser Lys Ile Val Val His
65                  70                  75                  80

Lys Asp Trp Asn Ser Asn Gln Ile Ser Lys Gly Asn Asp Ile Ala Leu
                85                  90                  95

Leu Lys Leu Ala Asn Pro Val Ser Leu Thr Asp Lys Ile Gln Leu Ala
            100                 105                 110
```

Cys Leu Pro Pro Ala Gly Thr Ile Leu Pro Asn Asn Tyr Pro Cys Tyr
            115                 120                 125

Val Thr Gly Trp Gly Arg Leu Gln Thr Asn Gly Ala Val Pro Asp Val
        130                 135                 140

Leu Gln Gln Gly Arg Leu Leu Val Val Asp Tyr Ala Thr Cys Ser Ser
145                 150                 155                 160

Ser Ala Trp Trp Gly Ser Ser Val Lys Thr Ser Met Ile Cys Ala Gly
                165                 170                 175

Gly Asp Gly Val Ile Ser Ser Cys Asn Gly Asp Ser Gly Gly Pro Leu
                180                 185                 190

Asn Cys Gln Ala Ser Asp Gly Arg Trp Gln Val His Gly Ile Val Ser
            195                 200                 205

Phe Gly Ser Arg Leu Gly Cys Asn Tyr Tyr His Lys Pro Ser Val Phe
        210                 215                 220

Thr Arg Val Ser Asn Tyr Ile Asp Trp Ile Asn Ser Val Ile Ala Asn
225                 230                 235                 240

Asn

<210> SEQ ID NO 7
<211> LENGTH: 241
<212> TYPE: PRT
<213> ORGANISM: Homo sapiens

<400> SEQUENCE: 7

Met Leu Gly Gly Glu Glu Ala Arg Pro Asn Ser Trp Pro Trp Gln Val
1               5                   10                  15

Ser Leu Gln Tyr Ser Ser Asn Gly Gln Trp Tyr His Thr Cys Gly Gly
            20                  25                  30

Ser Leu Ile Ala Asn Ser Trp Val Leu Thr Ala Ala His Cys Ile Ser
        35                  40                  45

Ser Ser Gly Ile Tyr Arg Val Met Leu Gly Gln His Asn Leu Tyr Val
    50                  55                  60

Ala Glu Ser Gly Ser Leu Ala Val Ser Val Ser Lys Ile Val Val His
65                  70                  75                  80

Lys Asp Trp Asn Ser Asp Gln Val Ser Lys Gly Asn Asp Ile Ala Leu
                85                  90                  95

Leu Lys Leu Ala Asn Pro Val Ser Leu Thr Asp Lys Ile Gln Leu Ala
            100                 105                 110

Cys Leu Pro Pro Ala Gly Thr Ile Leu Pro Asn Asn Tyr Pro Cys Tyr
        115                 120                 125

Val Thr Gly Trp Gly Arg Leu Gln Thr Asn Gly Ala Leu Pro Asp Asp
    130                 135                 140

Leu Lys Gln Gly Gln Leu Leu Val Val Asp Tyr Ala Thr Cys Ser Ser
145                 150                 155                 160

Ser Gly Trp Trp Gly Ser Thr Val Lys Thr Asn Met Ile Cys Ala Gly
                165                 170                 175

Gly Asp Gly Val Ile Cys Thr Cys Asn Gly Asp Ser Gly Gly Pro Leu
                180                 185                 190

Asn Cys Gln Ala Ser Asp Gly Arg Trp Glu Val His Gly Ile Gly Ser
            195                 200                 205

Leu Thr Ser Val Leu Gly Cys Asn Tyr Tyr Lys Pro Ser Ile Phe
        210                 215                 220

Thr Arg Val Ser Asn Tyr Asn Asp Trp Ile Asn Ser Val Ile Ala Asn
225                 230                 235                 240

Asn

<210> SEQ ID NO 8
<211> LENGTH: 242
<212> TYPE: PRT
<213> ORGANISM: Homo sapiens

<400> SEQUENCE: 8

```
Val Val His Gly Glu Asp Ala Val Pro Tyr Ser Trp Pro Trp Gln Val
1               5                   10                  15

Ser Leu Gln Tyr Glu Lys Ser Gly Ser Phe Tyr His Thr Cys Gly Gly
            20                  25                  30

Ser Leu Ile Ala Pro Asp Trp Val Thr Ala Gly His Cys Ile Ser
        35                  40                  45

Arg Asp Leu Thr Tyr Gln Val Val Leu Gly Glu Tyr Asn Leu Ala Val
50                  55                  60

Lys Glu Gly Pro Glu Gln Val Ile Pro Ile Asn Ser Glu Glu Leu Phe
65                  70                  75                  80

Val His Pro Leu Trp Asn Arg Ser Cys Val Ala Cys Gly Asn Asp Ile
                85                  90                  95

Ala Leu Ile Lys Leu Ser Arg Ser Ala Gln Leu Gly Asp Ala Val Gln
                100                 105                 110

Leu Ala Ser Leu Pro Pro Ala Gly Asp Ile Leu Pro Asn Lys Thr Pro
            115                 120                 125

Cys Tyr Ile Thr Gly Trp Gly Arg Leu Tyr Thr Asn Gly Pro Leu Pro
        130                 135                 140

Asp Lys Leu Gln Gln Ala Arg Leu Pro Val Val Asp Tyr Lys His Cys
145                 150                 155                 160

Ser Arg Trp Asn Trp Trp Gly Ser Thr Val Lys Lys Thr Met Val Cys
                165                 170                 175

Ala Gly Gly Tyr Ile Arg Ser Gly Cys Asn Gly Asp Ser Gly Gly Pro
                180                 185                 190

Leu Asn Cys Pro Thr Glu Asp Gly Gly Trp Gln Val His Gly Val Thr
            195                 200                 205

Ser Phe Val Ser Ala Phe Gly Cys Asn Phe Ile Trp Lys Pro Thr Val
        210                 215                 220

Phe Thr Arg Val Ser Ala Phe Ile Asp Trp Ile Glu Glu Thr Ile Ala
225                 230                 235                 240

Ser His
```

<210> SEQ ID NO 9
<211> LENGTH: 242
<212> TYPE: PRT
<213> ORGANISM: Homo sapiens

<400> SEQUENCE: 9

```
Val Val Asn Gly Glu Asp Ala Val Pro Tyr Ser Trp Pro Trp Gln Val
1               5                   10                  15

Ser Leu Gln Tyr Glu Lys Ser Gly Ser Phe Tyr His Thr Cys Gly Gly
            20                  25                  30

Ser Leu Ile Ala Pro Asp Trp Val Thr Ala Gly His Cys Ile Ser
        35                  40                  45

Ser Ser Arg Thr Tyr Gln Val Val Leu Gly Glu Tyr Asp Arg Ala Val
50                  55                  60

Lys Glu Gly Pro Glu Gln Val Ile Pro Ile Asn Ser Gly Asp Leu Phe
```

```
                 65                  70                  75                  80
Val His Pro Leu Trp Asn Arg Ser Cys Val Ala Cys Gly Asn Asp Ile
                 85                  90                  95
Ala Leu Ile Lys Leu Ser Arg Ser Ala Gln Leu Gly Asp Ala Val Gln
                100                 105                 110
Leu Ala Ser Leu Pro Pro Ala Gly Asp Ile Leu Pro Asn Glu Thr Pro
                115                 120                 125
Cys Tyr Ile Thr Gly Trp Gly Arg Leu Tyr Thr Asn Gly Pro Leu Pro
                130                 135                 140
Asp Lys Leu Gln Glu Ala Leu Leu Pro Val Val Asp Tyr Glu His Cys
145                 150                 155                 160
Ser Arg Trp Asn Trp Trp Gly Ser Ser Val Lys Lys Thr Met Val Cys
                165                 170                 175
Ala Gly Gly Asp Ile Arg Ser Gly Cys Asn Gly Asp Ser Gly Gly Pro
                180                 185                 190
Leu Asn Cys Pro Thr Glu Asp Gly Gly Trp Gln Val His Gly Val Thr
                195                 200                 205
Ser Phe Val Ser Ala Phe Gly Cys Asn Thr Arg Arg Lys Pro Thr Val
                210                 215                 220
Phe Thr Arg Val Ser Ala Phe Ile Asp Trp Ile Glu Thr Ile Ala
225                 230                 235                 240
Ser His

<210> SEQ ID NO 10
<211> LENGTH: 98
<212> TYPE: PRT
<213> ORGANISM: Homo sapiens

<400> SEQUENCE: 10

Gly Pro Ile Pro Glu Val Leu Lys Asn Tyr Met Asp Ala Gln Tyr Tyr
1                   5                  10                  15
Gly Glu Ile Gly Ile Gly Thr Pro Pro Gln Cys Phe Thr Val Val Phe
                 20                  25                  30
Asp Thr Gly Ser Ser Asn Leu Trp Val Pro Ser Ile His Cys Lys Leu
                 35                  40                  45
Leu Asp Ile Ala Cys Trp Ile His His Lys Tyr Asn Ser Asp Lys Ser
                 50                  55                  60
Ser Thr Tyr Val Lys Asn Gly Thr Ser Phe Asp Ile His Tyr Gly Ser
65                  70                  75                  80
Gly Ser Leu Ser Gly Tyr Leu Ser Gln Asp Thr Val Ser Val Pro Cys
                 85                  90                  95
Gln Ser

<210> SEQ ID NO 11
<211> LENGTH: 244
<212> TYPE: PRT
<213> ORGANISM: Homo sapiens

<400> SEQUENCE: 11

Leu Gly Gly Val Lys Val Glu Arg Gln Val Phe Gly Glu Ala Thr Lys
1                   5                  10                  15
Gln Pro Gly Ile Thr Phe Ile Ala Ala Lys Phe Asp Gly Ile Leu Gly
                 20                  25                  30
Met Ala Tyr Pro Arg Ile Ser Val Asn Asn Val Leu Pro Val Phe Asp
                 35                  40                  45
```

```
Asn Leu Met Gln Gln Lys Leu Val Asp Gln Asn Ile Phe Ser Phe Tyr
    50                  55                  60

Leu Ser Arg Asp Pro Asp Ala Gln Pro Gly Gly Glu Leu Met Leu Gly
 65                  70                  75                  80

Gly Thr Asp Ser Lys Tyr Tyr Lys Gly Ser Leu Ser Tyr Leu Asn Val
                 85                  90                  95

Thr Arg Lys Ala Tyr Trp Gln Val His Leu Asp Gln Val Glu Val Ala
            100                 105                 110

Ser Gly Leu Thr Leu Cys Lys Glu Gly Cys Glu Ala Ile Val Asp Thr
        115                 120                 125

Gly Thr Ser Leu Met Val Gly Pro Val Asp Glu Val Arg Glu Leu Gln
130                 135                 140

Lys Ala Ile Gly Ala Val Pro Leu Ile Gln Gly Glu Tyr Met Ile Pro
145                 150                 155                 160

Cys Glu Lys Val Ser Thr Leu Pro Ala Ile Thr Leu Lys Leu Gly Gly
                165                 170                 175

Lys Gly Tyr Lys Leu Ser Pro Glu Asp Tyr Thr Leu Lys Val Ser Gln
            180                 185                 190

Ala Gly Lys Thr Leu Cys Leu Ser Gly Phe Met Gly Met Asp Ile Pro
        195                 200                 205

Pro Pro Ser Gly Pro Leu Trp Ile Leu Gly Asp Val Phe Ile Gly Arg
210                 215                 220

Tyr Tyr Thr Val Phe Asp Arg Asp Asn Asn Arg Val Gly Phe Ala Glu
225                 230                 235                 240

Ala Ala Arg Leu

<210> SEQ ID NO 12
<211> LENGTH: 271
<212> TYPE: PRT
<213> ORGANISM: Homo sapiens

<400> SEQUENCE: 12

Val Thr Glu His Val Leu Ala Asn Asn Asp Val Ser Cys Asp His Pro
 1               5                  10                  15

Ser Asn Thr Val Pro Ser Gly Ser Asn Gln Asp Leu Gly Ala Gly Ala
                 20                  25                  30

Gly Glu Asp Ala Arg Ser Asp Asp Ser Ser Arg Ile Ile Asn Gly
             35                  40                  45

Ser Asp Cys Asp Met His Thr Gln Pro Trp Gln Ala Ala Leu Leu Leu
 50                  55                  60

Arg Pro Asn Gln Leu Tyr Cys Gly Ala Val Leu Val His Pro Gln Trp
 65                  70                  75                  80

Leu Leu Thr Ala Ala His Cys Arg Lys Lys Val Phe Arg Val Arg Leu
                 85                  90                  95

Gly His Tyr Ser Leu Ser Pro Val Tyr Glu Ser Gly Gln Gln Met Phe
            100                 105                 110

Gln Gly Val Lys Ser Ile Pro His Pro Gly Tyr Ser His Pro Gly His
        115                 120                 125

Ser Asn Asp Leu Met Leu Ile Lys Leu Asn Arg Arg Ile Arg Pro Thr
130                 135                 140

Lys Asp Val Arg Pro Ile Asn Val Ser Ser His Cys Pro Ser Ala Gly
145                 150                 155                 160

Thr Lys Cys Leu Val Ser Gly Trp Gly Thr Thr Lys Ser Pro Gln Val
                165                 170                 175
```

```
His Phe Pro Lys Val Leu Gln Cys Leu Asn Ile Ser Val Leu Ser Gln
            180                 185                 190

Lys Arg Cys Glu Asp Ala Tyr Pro Arg Gln Ile Asp Asp Thr Met Phe
        195                 200                 205

Cys Ala Gly Asp Lys Ala Gly Arg Asp Ser Cys Gln Gly Asp Ser Gly
        210                 215                 220

Gly Pro Val Val Cys Asn Gly Ser Leu Gln Gly Leu Val Ser Trp Gly
225                 230                 235                 240

Asp Tyr Pro Cys Ala Arg Pro Asn Arg Pro Gly Val Tyr Thr Asn Leu
                245                 250                 255

Cys Lys Phe Thr Lys Trp Ile Gln Glu Thr Ile Gln Ala Asn Ser
                260                 265                 270

<210> SEQ ID NO 13
<211> LENGTH: 223
<212> TYPE: PRT
<213> ORGANISM: Homo sapiens

<400> SEQUENCE: 13

Leu Val His Gly Gly Pro Cys Asp Lys Thr Ser His Pro Tyr Gln Ala
1               5                   10                  15

Ala Leu Tyr Thr Ser Gly His Leu Leu Cys Gly Gly Val Leu Ile His
            20                  25                  30

Pro Leu Trp Val Leu Thr Ala Ala His Cys Lys Lys Pro Asn Leu Gln
        35                  40                  45

Val Phe Leu Gly Lys His Asn Leu Arg Gln Arg Glu Ser Ser Gln Glu
    50                  55                  60

Gln Ser Ser Val Val Arg Ala Val Ile His Pro Asp Tyr Asp Ala Ala
65                  70                  75                  80

Ser His Asp Gln Asp Ile Met Leu Leu Arg Leu Ala Arg Pro Ala Lys
                85                  90                  95

Leu Ser Glu Leu Ile Gln Pro Leu Pro Leu Glu Arg Asp Cys Ser Ala
            100                 105                 110

Asn Thr Thr Ser Cys His Ile Leu Gly Trp Gly Lys Thr Ala Asp Gly
            115                 120                 125

Asp Phe Pro Asp Thr Ile Gln Cys Ala Tyr Ile His Leu Val Ser Arg
        130                 135                 140

Glu Glu Cys Glu His Ala Tyr Pro Gly Gln Ile Thr Gln Asn Met Leu
145                 150                 155                 160

Cys Ala Gly Asp Glu Lys Tyr Gly Lys Asp Ser Cys Gln Gly Asp Ser
                165                 170                 175

Gly Gly Pro Leu Val Cys Gly Asp His Leu Arg Gly Leu Val Ser Trp
            180                 185                 190

Gly Asn Ile Pro Cys Gly Ser Lys Glu Lys Pro Gly Val Tyr Thr Asn
        195                 200                 205

Val Cys Arg Tyr Thr Asn Trp Ile Gln Lys Thr Ile Gln Ala Lys
    210                 215                 220
```

METHODS OF TREATING NEUROLOGICAL DISORDERS

CROSS-REFERENCE TO RELATED APPLICATIONS

This application is a continuation of International Patent Application No. PCT/US2019/042879, filed on Jul. 22, 2019, which claims the benefit of and priority to U.S. Provisional Application Nos. 62/702,188, filed Jul. 23, 2018; 62/702,191, filed Jul. 23, 2018; and 62/815,123, filed Mar. 7, 2019, the disclosure of each of which is hereby incorporated by reference in its entirety for all purposes.

SEQUENCE LISTING

The instant application contains a Sequence Listing which has been submitted electronically in ASCII format and is hereby incorporated by reference in its entirety. The ASCII copy, created on Jul. 22, 2019, is named 120902-10303_ST25.txt and is 26 kb in size.

FIELD OF THE INVENTION

The invention relates generally to a method for treating a subject diagnosed as having a neurological disorder characterized by the presence of toxic proteins comprising contacting the cerebrospinal fluid (CSF) of the subject with an agent capable of removing or degrading the toxic protein.

BACKGROUND

The deposition of aggregated proteins defines virtually all neurodegenerative disorders, including, for example, Alzheimer's disease (AD), Parkinson's disease (PD), Huntington's disease, and amyotrophic lateral sclerosis (ALS) (Kaufman et al., *Neurotherapeutics* 2013, 10, 371-382), frontotemporal dementia (FTD), progressive supranuclear palsy (PSP) (Wray et al., *Journal of Neurochemistry*, 2008, 105, 2343-2352) and corticobasal degeneration (CBD) (Narasimhan at al, *The Journal of Neuroscience*, 2017, 37 (47), 11406-11423).

Amyotrophic lateral sclerosis (ALS) and frontotemporal lobar degeneration (FTLD) (e.g., frontotemporal dementia (FTD)) are progressive, terminal neurological diseases. ALS affects 2 in 100,000 people and has historically been characterized by the degeneration of motor neurons in the brain and spinal cord, leading to progressive spasticity, muscle weakness and wasting and ultimately death due to respiratory failure, typically within three years from symptom onset. More recently, ALS has been increasingly recognized as a multisystem disorder with impairment of frontotemporal functions such as cognition and behavior in up to 50% of patients (Giordana et al., *Neurol. Sci.,* 2001 32, 9-16; Lomen-Hoerth et al., *Neurology,* 2003, 59, 1077-1079; and Phukan et al., *Lancet Neurol.,* 2007, 6, 994-1003).

Frontotemporal lobar degeneration (FTLD) (clinically also referred to as frontotemporal dementia (FTD), including behavioral variant frontotemporal dementia (bvFTD), semantic variant primary progressive aphasia (svPPA) and non-fluent/agrammatic variant primary progressive aphasia (nfvPPA)), is the second most common cause of presenile dementia, characterized by the degeneration of the frontal and temporal lobes of the brain, resulting in progressive changes in personality and behavior accompanied by language dysfunction, but with relative preservation of perception and memory (Graff-Radford and Woodruf, *Neurol.* 2007, 27, 48-57).

Both diseases are etiologically complex and environmental factors, in addition to genetic factors, are likely to contribute to their onset (Andersen and Al-Chalabi, *Nat. Rev. Neurol.* 2011, 7, 603-615; Paulson and Igo, *Semin Neurol.,* 2011, 31, 449-360).

Based on its pathobiology, ALS is considered a protein misfolding disorder, and as such is classified as a proteinopathy similar to other neurogenerative diseases (Grad and Cashman, *Prion,* 2014, 8, 33-41). These proteins accumulate in aggregates observed upon pathological examination of motor neurons and are being studied for potentially spreading through prion-like mechanisms.

All variants of FTLD/FTD show abnormal protein inclusions in neurons and glial cells, (e.g. tau positive inclusions in FTLD-tau (e.g. FTD-tau or Pick's disease), alpha-synuclein-negative inclusions which contain TAR DNA-Binding protein 43 (TDP-43) conjugated with ubiquitin in FTLD-TDP (e.g., FTD-TDP), and fused sarcoma protein inclusions in FTLD-FUS (e.g., FTD-FUS)).

TDP-43 was identified as the major component of inclusions found in the brains of patients with ALS and FTLD (Arai et al., *Biochem. Biophys. Res. Commun.* 2006, 351, 602; Neumann et al. *Science,* 2006314, 130-133). Patients with these diseases show autosomal-dominant missense mutations in the TARDBP gene, mostly located in the C-terminal glycine-rich region (Pesiridis et al., 2009). Pathological TDP-43 is hyperphosphorylated, ubiquitinated, and abnormally cleaved to generate aggregation-prone C-terminal fragments (Arai et al., *Neuropathology,* 2010, 30, 170-181; Hasegawa et al., *Ann. Neurol.,* 2008, 64, 60-7; Hasegawa et al., *J. Mol. Neurosci.,* 2011, 45, 480-485).

Other notable mutations identified in familial cases of ALS are predominantly associated with Mendelian-inherited mutations in genes encoding Cu/Zn superoxide dismutase (SOD1) and fused in sarcoma/translocated in liposarcoma FUS/TLS. Recent research has identified propagated protein misfolding properties in both mutant and wild-type SOD1.

Progressive supranuclear palsy (PSP) or Steele-Richardson-Olszewski disease is an adult onset movement disorder that is characterized clinically by parkinsonian symptoms together with other features, including postural instability, downward gaze supranuclear palsy, dysarthria and dysphagia (Steele et al. *Arch. Neurol.* 1964, 10, 333-359).

Pathologically, the brains of patients with PSP contain deposits of the microtubule-associated protein tau, which is hyperphosphorylated compared to soluble tau from control brain. Hyperphosphorylation and aggregation of tau is not specific to PSP, but is present in a whole range of disorders known as tauopathies, of which Alzheimer's disease is the most prevalent and well characterized (Buee et al. *Brain Res. Brain Res. Rev.,* 2000, 33, 95-130). Tau is normally a highly soluble protein, which in tauopathies becomes hyperphosphorylated and misfolded, forming larger aggregates as intracellular inclusions.

In AD, the burden of tau aggregates correlates closely with neuron death and cognitive decline, and tau aggregates cause neurodegeneration in other tauopathies (Arriagada et al., *Neurology,* 1992, 42, 631-639; Gomez-Isla et al., *Ann. Neurol.* 1997, 41, 17-24; Giannakopoulos et al., *Neurology,* 2003, 60, 1495-1500). AD is clinically characterized by early memory loss and eventual dementia (Lee et al., *Annu. Rev. Neurosci.,* 2001, 24, 1121-1159). In AD, tau aggregates deposit in a stereotypical manner along anatomically connected networks from the transentorhinal cortex to neocortical areas (Braak and Braak, 1991; Braak et al., 2011; Braak and Del Tredici, 2012; Cho et al., 2016b). In AD and several other tauopathies, tau aggregates are composed of all six isoforms of tau (both 3R and 4R tau) primarily in neuronal cell bodies (neurofibrillary tangles (NFTs) and in axons (neuropil threads) (Lee et al., 2001).

In contrast, corticobasal degeneration (CBD) and progressive supranuclear palsy (PSP) patients have an earlier onset and shorter duration of disease than AD patients, and primarily show motor dysfunction (Lee et al., 2001). In CBD, tau aggregates are found in the cerebral cortex, basal ganglia, deep cerebellar nuclei, and substantia nigra. They are composed primarily of 4R tau isoforms in both neurons and glia in CBD, including astrocytic plaques and oligodendroglial coiled bodies (Lee et al., 2001).

Classical PSP is characterized by tau aggregates in primarily subcortical regions, such as midbrain and basal ganglia (Williams and Lees, 2009). Similar to CBD, PSP tau aggregates are composed of 4R tau isoforms in both neurons and glia, including tufted astrocytes and oligodendroglial coiled bodies (Lee et al., 2001). Although PSP was initially described as a single syndrome, recent evidence suggests that PSP may constitute multiple clinical subtypes (Williams and Lees, 2009). There is also some overlap in the manifestations of CBD and PSP (Sha et al., 2006).

Parkinson's disease (PD) is a long-term degenerative disorder of the central nervous system that mainly affects the motor system. The symptoms generally come on slowly over time. Toxic interactions between tau and alpha synuclein may lead to hyperphosphorylation of tau and eventually to the deposition of both proteins in the disease (Lei et al. *Int. J. Biochem. Cell Biol.* 2010, 42 (11), pp. 1775-1778).

Primary age-related tauopathy (PART) is a recently described neuropathological designation used to describe the neurofibrillary tangles (NFT) that are commonly observed in the brains of normally aged individuals that can occur independently of the amyloid plaques of Alzheimer's disease (AD). Symptoms in persons with PART usually range from normal to amnestic cognitive changes, with only a minority exhibiting profound impairment.

Chronic traumatic encephalopathy (CTE) is a neurodegenerative disease found in people who have had multiple head injuries. Symptoms of CTE include behavioral and mood changes, memory loss, cognitive impairment and dementia. CTE is a tauopathy characterized by the deposition of hyperphosphorylated tau protein as NFT's, astrocytic tangles and neurites in striking clusters around small blood vessels of the cortex. Severely affected cases show tau pathology throughout the brain. Abnormalities in phosphorylated 43 kDa TAR DNA-binding protein are found in most cases of CTE; beta-amyloid is identified in 43%, associated with age (McKee et al., *Brain Pathol*, 2015, 25(3), pp. 350-364).

Frontotemporal dementia with Parkinsonism linked to chromosome 17 (FTDP-17) is an autosomal dominant neurodegenerative disorder characterized by a loss of nerve cells (neurons) in areas of the brain called the frontal and temporal lobes. Over time, a loss of these cells can affect personality, behavior, language, and movement. FTDP-17 is caused by mutations in the MAPT tau gene, which lead to disruptions in the normal structure and function of tau. The pathogenetic mechanisms underlying the disorder are thought to be related to the altered proportion of tau isoforms or to the ability of tau to bind microtubules and to promote microtubule assembly (Wszolek, Z. et al., *Orphanet J. Rare Dis.*, 2006, 1, pp 30).

Lytico-bodig disease (sometimes spelled Lytigo-bodig) or amyotrophic lateral sclerosis-parkinsonism-dementia complex (ALS-PDC) is an endemic neurodegenerative disorder of the Western Pacific islands, known to occur only in the islands of the Guam archipelago, the Kii peninsula of Japan, and West Papua, Indonesia. It is a slowly progressive degenerative disease with a spectrum of clinical presentation that can include features of amyotrophic lateral sclerosis, Parkinsonism, and dementia. It is characterized by distinct neuropathologic features of widely distributed neurofibrillary tangles comprised of tau in addition to pathologic findings of amyotrophic lateral sclerosis.

Ganglioglioma is a rare, slow-growing primary central nervous system (CNS) tumor which most frequently occurs in the temporal lobes of children and young adults. Ganglion cells within these lesions occasionally exhibit neurodegenerative changes including neurofibrillary tangles (NFT) similar to those in Alzheimer's disease (Brat D J et al., *Neuropathol. Appl. Neurobiol.*, 2001, 27 (3), pp 197-205).

Meningioangiomatosis is a rare disease of the brain. It is characterized by a benign lesion of the leptomeninges usually involving the cerebral cortex, and by leptomeningeal and meningovascular proliferation. Neurofibrillary tangles are often present in both the transcortical plaques that characterize the disease lesions and the surrounding cortex, but senile plaques and granulovacuolar degeneration are not common (Laws, *Journal of Neuropathology and Experimental Neurology*, 1986, 45 (4) pp 426-446).

Post-encephalitic Parkinsonism is a disease believed to be caused by a viral illness that triggers degeneration of the nerve cells in the substantia nigra. Overall, this degeneration leads to clinical Parkinsonism. The brain regions affected contain neurofibrillary tangles, similar to those seen in Alzheimer's disease. Nevertheless, the senile plaques common in Alzheimer's disease are not found (Evidente, V. et al. *J. Neurol. Neurosurg. Psychiatry*, 1998, 64 (1) pp 5).

Subacute sclerosing panencephalitis (SSPE) is a rare and chronic form of progressive brain inflammation caused by a persistent infection with measles virus (which can be a result of a mutation of the virus itself). The condition primarily affects children and young adults. It has been estimated that about 1 in 10,000 people infected with measles will eventually develop SSPE.

SUMMARY

One aspect of the invention provides a method for treating a neurological disorder characterized by the presence of tau protein in cerebrospinal fluid (CSF), the method comprising contacting the CSF of a subject in need thereof in situ with an effective amount of a protease capable of removing or degrading the tau protein.

In certain embodiments, the toxic protein is selected from the group consisting of tau, α-synuclein, TDP-43, and FUS. In certain embodiments, the toxic protein is tau. In certain embodiments, the tau protein is hyperphosphorylated. In certain embodiments, the tau protein is present in the form of protein dimer, protein oligomer, or protein aggregate. In certain embodiments, the tau protein is soluble.

In certain embodiments, the neurological disorder is a tauopathy selected from progressive supranuclear palsy (PSP), Alzheimer's disease (AD), Parkinson's disease (PD), frontotemporal lobar degeneration (FTLD), primary age-related tauopathy (PART), chronic traumatic encephalopathy (CTE), corticobasal degeneration (CBD), frontotemporal dementia with parkinsonism linked to chromosome 17 (FTDP-17), Lytico-bodig disease, ganglioglioma, meningioangiomatosis, post-encephalitic Parkinsonism, and sub-acute-sclerosing panenecephalitis (SSPE). In certain embodiments, the neurological disorder is PSP. In certain embodiments, the neurological disorder is FTLD. In certain embodiments, the neurological disorder is AD.

In certain embodiments, the protease is a serine protease. In certain embodiments, the protease is a trypsin, elastase, cathepsin G, kallikrein-5, or kallikrein-6.

In certain embodiments, the toxic protein is tau and the protease is trypsin, elastase, cathepsin G, kallikrein-5, or kallikrein-6. In certain embodiments, the toxic protein is α-synuclein and the protease is trypsin, elastase, or kallikrein-6. In certain embodiments, the toxic protein is TDP-43 and the protease is kallikrein-5 or kallikrein-6.

In certain embodiments, the protease is immobilized to a solid substrate. In certain embodiments, the solid substrate comprises a porous solid substrate. In certain embodiments, the solid substrate comprises a cross-linked resin. In certain embodiments, the cross-linked resin comprises an agarose resin. In certain embodiments, the protease is immobilized by covalent cross-linking to the solid substrate. In certain embodiments, the solid substrate is comprised in a system that is implanted into the subject. In certain embodiments, the system is implanted into the subarachnoid space of the subject. In certain embodiments, the system further comprises a size filter that removes large biomolecules.

In certain embodiments, the method disclosed herein further comprises the step of detecting tau protein from the CSF of the subject. In certain embodiments, the step of detection is conducted prior to the step of contacting, thereby identifying the subject as suitable for the treatment.

In certain embodiments, the method further comprises the step of detecting tau protein from the CSF of the subject. In certain embodiments, the step of detection is conducted prior to the step of contacting, thereby identifying the subject as suitable for the treatment. In certain embodiments, the subject identified as suitable for the treatment has an elevated level of tau protein in the CSF compared to a subject that does not have any neurological disorder. In certain embodiments, the subject identified as suitable for the treatment has an elevated level of hyperphosphorylated tau protein in the CSF compared to a subject that does not have any neurological disorder. In certain embodiments, the subject identified as suitable for the treatment has an elevated level of tau protein in the form of protein dimer, protein oligomer, or protein aggregate compared to a subject that does not have any neurological disorder.

In certain embodiments, the subject is a human.

Other objects and advantages will become apparent to those skilled in the art from a consideration of the ensuing Detailed Description, Examples, and Claims.

DETAILED DESCRIPTION

Definitions

Figure 1:
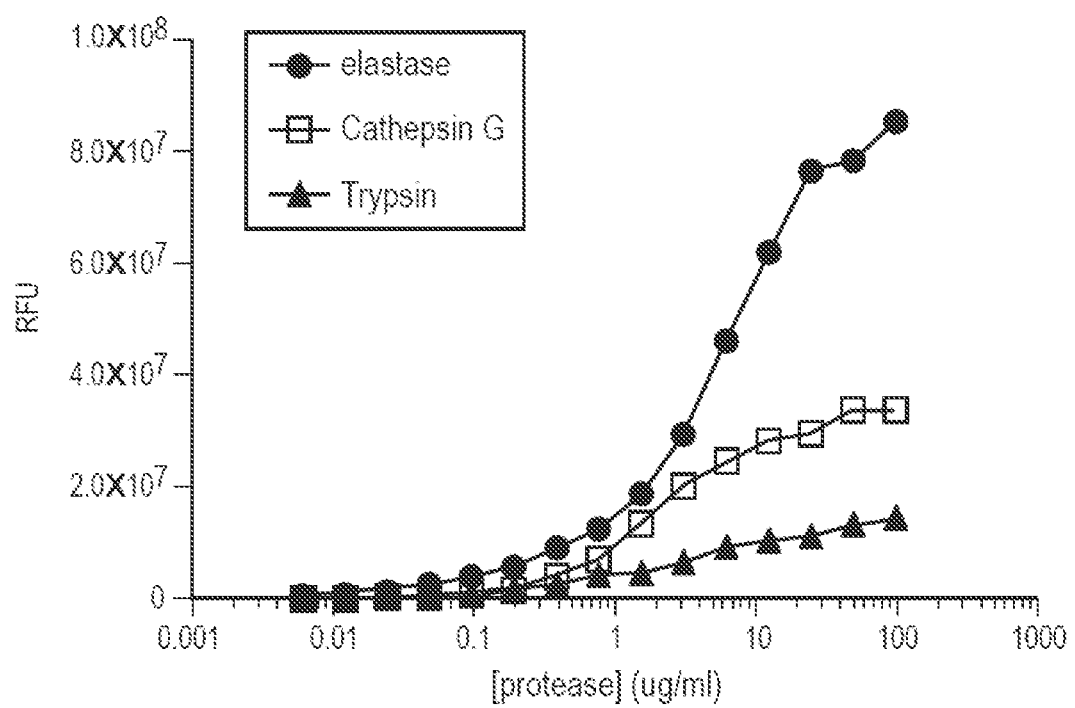
FIG. 1 is a line graph showing protease activity of elastase, cathepsin G, and trypsin with Bodipy®-labelled casein as substrate. RFU represents relative fluroscense unit.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgous monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating," and "treatment" contemplate an action that occurs while a subject is diagnosed as having the specified disease, disorder or condition, which reduces the severity of the disease, disorder or condition, reduces the severity of at least one symptom of the disease, disorder or condition or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of an agent refers to an amount sufficient to elicit the desired biological response. As will be appreciated by those of ordinary skill in this art, the effective amount of an agent of the invention may vary depending on such factors as the desired biological endpoint, the pharmacokinetics of the agent, the disease being treated, the mode of administration, and the age, health, and condition of the subject. An effective amount encompasses therapeutic and prophylactic treatment.

As used herein, and unless otherwise specified, a "therapeutically effective amount" of an agent is an amount sufficient to provide a therapeutic benefit in the treatment of a disease, disorder or condition, or to delay or minimize one or more symptoms associated with the disease, disorder or condition. A therapeutically effective amount of an agent means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, the term "toxic protein" refers to (a) an abnormal protein (e.g., an abnormal variant or mutant of a naturally occurring protein) or an abnormally high amount of a naturally occurring protein that has a negative effect on the health and survival of a target tissue (e.g., brain or neuronal tissue), i.e., in a toxic form; or (b) a protein that can be converted (e.g., by misfolding, aggregation, post-translational modification, or proteolytic cleavage) under pathophysiological conditions to a protein described in (a), i.e., in a pre-toxic form. For example, a tau protein in a toxic form can be any tau protein (e.g. tau protein species) that has a negative effect on the health and survival of a target tissue (e.g., tau protein aggregates, tau protein tangles, mislocalized tau, conformationally changed tau, tau oligomers, hyperphosphorylated tau proteins, soluble tau proteins or tau dimers).

As used herein, the term "significant effect" refers to an effect that is measurable, has a magnitude that is outside the margin of error of the measurement (i.e., is statistically significant) and is known or predicted to have a clinically meaningful impact in a subject (e.g., it is known or predicted to cause a clinically significant increase or decrease in the severity of a symptom or side effect or to cause or contribute to the development of a symptom or side effect not previously present in the subject).

As used herein, the term "immobilized" refers to that an agent (e.g., an antibody or an enzyme) is attached to an inert, insoluble material or is otherwise made insoluble as a precipitate (e.g., an amorphous precipitate, e.g., a crystalline precipitate), as a cross-linked precipitate (e.g., an amorphous cross-linked precipitate, e.g., a crystalline cross-linked precipitate) or by encapsulation (e.g., encapsulation in a porous container).

Methods of Treating Cerebrospinal Fluid (CSF)

The invention provides for methods of treating a neurological disorder characterized by the presence of a toxic protein in cerebrospinal fluid (CSF), the method comprising contacting the CSF of a subject in need thereof with an effective amount of a protease capable of removing or degrading the toxic protein.

The invention also provides for compositions comprising a) cerebrospinal fluid (CSF) of a subject having a neurological disorder characterized by the presence of a toxic protein in the CSF; and
b) a protease capable of degrading or removing the toxic protein.

In certain embodiments, the toxic protein is tau (e.g., tau protein aggregates, tau protein tangles, tau oligomers, hyperphosphorylated tau proteins, soluble tau proteins, tau dimers). In an embodiment, the toxic protein is α-synuclein, TDP-43, FUS/TLS, SOD1, β-amyloid, Huntingtin protein (HTT) (e.g., with glutamate repeats), or a prion protein. A neurological disease is designated as a toxic protein positive if it is characterized by the presence of the toxic protein or by a mutation in a gene that encodes the toxic protein. In certain embodiments, the toxic protein is present in a toxic form (e.g., protein aggregate, protein tangles, protein oligomer, protein fibril, hyperphosphorylated protein, or misfolded protein) in the CSF. In certain embodiments, the toxic protein is present in a pre-toxic form in the CSF.

In certain embodiments, the neurological disorder is frontotemporal lobar degeneration (FTLD). In certain embodiments, the FTLD is frontotemporal dementia (FTD). In certain embodiments, the neurological disorder is FTLD-tau (e.g., FTD-tau, e.g., Pick's disease).

In certain embodiments, the neurological disorder is a tauopathy. Exemplary tauopathies include but are not limited to progressive supranuclear palsy (PSP), Alzheimer's disease (AD), Parkinson's disease (PD), primary age-related tauopathy (PART), chronic traumatic encephalopathy (CTE), corticobasal degeneration (CBD) (also known as corticobasal ganglionic degeneration (CBGD)), frontotemporal dementia with parkinsonism linked to chromosome 17 (FTDP-17), lytico-bodig disease, ganglioglioma, meningioangiomatosis, post-encephalitic Parkinsonism and subacute sclerosing panencephalitis (SSPE).

In certain embodiments, the neurological disorder is selected from Progressive supranuclear palsy (PSP), Alzheimer's disease (AD), Parkinson's disease (PD), primary age-related tauopathy (PART), chronic traumatic encephalopathy (CTE), corticobasal degeneration (CBD) (also known as corticobasal ganglionic degeneration (CBGD)), frontotemporal dementia with parkinsonism linked to chromosome 17 (FTDP-17), lytico-bodig disease, ganglioglioma, meningioangiomatosis, post-encephalitic Parkinsonism subacute sclerosing panencephalitis (SSPE), Huntington's disease (HD), Creutzfeldt-Jakob disease (CJD), variant Creutzfeldt-Jakob disease (vCJD), and amyotrophic lateral sclerosis (ALS).

In certain embodiments, the neurological disorder is selected from the group consisting of TDP-43 positive ALS, SOD1 positive ALS, FUS positive ALS, TDP-43 positive frontotemporal dementia (FTD), SOD1 positive FTD, FUS positive FTD, TDP-43 positive frontotemporal lobar degeneration (FTLD), SOD1 positive FTLD), FUS positive FTLD, frontotemporal dementia (FTD) (e.g., FTD with tau aggregates) or progressive supranuclear palsy (PSP).

In certain embodiments, the subject is a human. In certain embodiments, the subject is a non-human animal (e.g., a dog, a cat, a horse, a cow, a pig, a sheep, a goat, a chicken, or a non-human primate).

Figure 4:
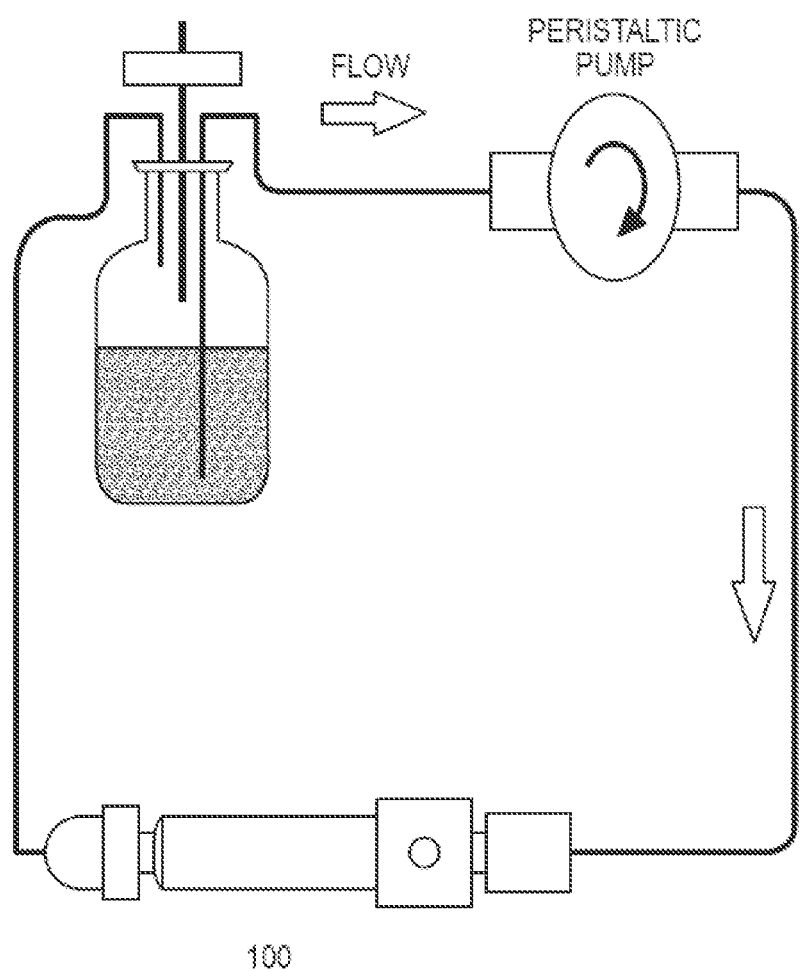
FIG. 4 is a representative diagram showing an exemplary device for removal of CSF containing toxic proteins and reintroduction of CSF following contact with a device 100 comprising protease immobilized on an agarose column.

In certain embodiments, the CSF is removed from the subject prior to contacting with the agent and is reintroduced into the subject after contacting with the agent for the necessary length of time to effect treatment. For example, CSF may be removed by a peristaltic pump according to the flow diagram in FIG. 4 and reintroduced into the subject after the CSF contacts a device comprising protease immobilized on an agarose column.

In certain embodiments, the present disclosure provides a method by which the CSF of a subject (e.g., human) is contacted with a protease immobilized or connected to a solid surface, e.g., the inner surface of a device (e.g., a cartridge 100 of FIG. 4), implanted into the body of the subject. In certain embodiments, during or after use of the agent, the agent or the solid surface to which the protease is immobilized is extracted and a new batch of the protease or solid support (e.g., resin) to which a new batch of the protease is immobilized is reintroduced by injection to the device implanted in the subject. In certain embodiments, the removal or degradation of the toxic protein by contacting the CSF with the protease creates a concentration gradient of the toxic protein (e.g., tau) within the device. In exemplary embodiments, the direction of the concentration gradient is from the input to the output ends of the device, with higher concentration on the input end.

In certain other embodiments, the present disclosure provides a method comprising a step of removing the CSF from the subject (e.g., a non-human mammal (e.g., a dog, a cat, a horse, a cow, a pig, a sheep, a goat, a chicken, or a non-human primate)) prior to contacting the CSF with the protease and a step of reintroducing the CSF back into the subject after contacting it with the protease. For example, in some embodiments, the method comprises a step of removing the CSF from the subject prior to contacting the CSF with a device comprising an agent immobilized on an agarose column, and a step of reintroducing the CSF back into the subject after contacting the CSF with the device.

In certain embodiments, the protease used to perform the method is immobilized (e.g., immobilized on a solid substrate). In a further embodiment, the agent is immobilized by cross-linking to porous beads or porous membranes. In certain embodiments, the toxic protein is removed or degraded by contacting the CSF with a concentration gradient of the protease.

In some embodiments, the protease is immobilized on a solid support. In further embodiments, the solid support is a porous solid support. In some embodiments of the invention, the protease is attached to the support by covalent binding. In certain embodiments, the support is a cross-linked resin. In a further embodiment, the cross-linked resin is an agarose resin. In certain embodiments, the protease is immobilized on the solid support at a concentration of about 1 mg/ml to about 10 mg/ml.

In a further embodiment, before or after contacting with the protease, the CSF is filtered to remove the treatment agent prior to being reintroduced into the subject.

In certain embodiments, the CSF is continually circulated between the patient and an ex-vivo compartment containing the treatment agent.

In other embodiments of the invention, the protease is contacted with the CSF in situ. An in situ method can be implemented by implanting a system comprising an agent disclosed herein into the subject, for example, into the subarachnoid space of the subject. Such implantation allows continual degradation and removal of a toxic protein from the CSF, and may have a lower risk of CNS infection than repeated ex corporial methods. Accordingly, in certain embodiments, the method comprises contacting the CSF with a device implanted in the subject, wherein the device comprises the agent immobilized on a substrate. In certain embodiments, the agent can be delivered into or extracted from the device implanted in the subject by injection (e.g., through a subcutaneous injection port).

In a further embodiment, the method comprises administering the agent capable of removing or degrading the toxic protein directly to the CSF of the patient.

In certain embodiments, the toxic protein is removed or degraded by contacting the CSF with a concentration gradient of the protease (e.g., contacting the CSF with a concentration gradient of protease immobilized on a substrate). In certain embodiments, the protein is removed or degraded by contacting the CSF with immobilized proteases (e.g., contacting the CSF with a protease immobilized on a substrate).

Removal and/or Degradation of Toxic Proteins

The invention provides for methods of treating a neurological disorder characterized by the presence of a toxic protein in CSF, the method comprising contacting the CSF of a subject in need thereof in situ with an effective amount of a protease capable of removing or degrading the toxic protein.

In certain embodiments the toxic protein is a tau protein (e.g., tau protein aggregates, tau protein tangles, tau oligomers, hyperphosphorylated tau proteins, soluble tau proteins, tau dimers). In certain embodiments the toxic protein is a TDP-43 protein (e.g., a misfolded TDP-43 protein, e.g., a mutant TDP-43 protein). In certain embodiments, the toxic protein is a mutant or misfolded wild-type SOD1 protein. In certain embodiments the toxic protein is a mutant FUS/TLS protein. In certain embodiments, the toxic protein is in a toxic form.

The microtubule associating protein tau is a major component of the neurofibrillary tangles (NFT's) associated with AD and tauopathies that are characterized by hyperphosphorylation and aggregation of tau. Tau is an intrinsically unstructured protein due to its very low hydrophobic content containing a projection domain, a basic proline-rich region, and an assembly domain. Tau is known to carry various post-translational modifications, such as acetylation, deamidation, glycation, glycosylation, isomerisation, methylation, nitration, phosphorylation, proteolysis, sumoylation and ubiquitylation (see Martin et al. (2011) Neurochem. Int. 58, 458-71). Hyperphosphorylation of tau, particularly in the assembly domain, decreases the affinity of tau to the microtubules and impairs its ability to regulate microtubule dynamics and axonal transport. In addition, parts of the basic proline-rich domain and the pseudo-repeat also stabilize microtubules by interacting with its negatively charged surface. Alternative splicing of two N-terminal insert regions and of the second, third and tenth exons of tau results in six tau isoforms of varying length in the CNS (see Quinn et al. (2018) J. Alzheimers Dis. 63(1):13-33). The assembly domain in the carboxyl-terminal portion of the protein contains either three or four repeats (3R or 4R) of a conserved tubulin-binding motif depending on alternative splicing of exon 10. Tau 4R isoforms have greater microtubule binding and stabilizing ability than the 3R isoforms. Human adult brains have similar levels of 3R and 4R isoforms, whereas only 3R tau is expressed at the fetal stage. In tauopathies, mutations altering the splicing of tau transcript and the ratio of 3R to 4R tau isoforms are sufficient to cause neurodegenerative disease. In addition to the isoforms of full-length tau proteins, certain tau fragments (e.g., fragments resulting from endogenous protease cleavage) may also exhibit propensity to polymerize or aggregate, ability to facilitate polymerization or aggregation of another tau isoform or fragment, and/or ability to propagate tau polymerization or aggregation to other cells, thereby resulting in neurotoxicity. Such tau fragments include but are not limited to fragments 14-441, 26-230, 1-314, 26-44, 1-44, 1-156, 45-230, 243-441, 256-441, 256-368, 1-368, 1-421, 151-421, 1-391, and X-441 wherein X is any integer from 182 to 194 (amino acid positions numbered according to the sequence of the 2N4R isoform). In addition to these tau fragments, certain other fragments, such as fragments 124-441 and 1-402 (amino acid positions numbered according to the sequence of the 2N4R isoform), may be useful as biomarkers for diagnosing neurological disorders or monitoring patients' progression or response to treatment. More tau fragments are reviewed by Quinn et al. (2018) J. Alzheimers Dis. 63(1):13-33. In view of the above, tau in human brain tissue can exist in a variety of different lengths and morphologies and with multiple post-translational modifications. As used herein, the term "tau" includes various isoforms and fragments of tau protein with one or more post-translational modifications, and in any folding status. As tau progresses from normal to NFT it passes through a 'soluble' state in which the protein may be hyperphosphorylated, mislocalized, conformationally changed and/or oligomeric but not yet fibrillar.

Tau plays a critical role in the pathogenesis of AD and studies show that reduction of tau levels in AD animal models reverses disease phenotypes and that tau is necessary for the development of cognitive deficits in AD models caused by over-expression of Aβ. While neurofibrillary tangles (NFTs) have been implicated in mediating neurodegeneration in AD and tauopathies, animal models of tauopathy have shown that memory impairment and neuron loss do not associate well with accumulation of NFT. The pathological structures of tau most closely associated with AD progression are tau oligomers and it has been suggested that that tau tangles are not acutely neurotoxic, but rather that pretangle oligomeric tau species are responsible for the neurodegenerative phenotype, similar to toxic role of oligomeric Aβ species (Kopeikina et al., *Transl. Neurosci.* 2012 September; 3(3): 223-233).

Numerous studies suggest that extracellular tau species contribute to neurotoxicity through an "infectious" model of disease progression (Narasimhan et al., The Journal of Neuroscience, 2017, 37(47), 11406-11423). For example, tau pathology spreads contiguously throughout the brain from early to late stage disease, extracellular tau aggregates can propagate tau misfolding from the outside to the inside of a cell, brain extract from a transgenic mouse with aggregated mutant human tau transmits tau pathology throughout the brain in mice expressing normal human tau, induction of pro-aggregation human tau induces formation of tau aggregates and tangles composed of both human and normal murine tau (co-aggregation), and levels of tau rise in CSF in AD, whereas Aβ levels decrease (Kaufman at al, Neurotherapeutics, 2013, 10, 371-382).

Proteases

The invention provides for methods of treating a neurological disorder characterized by the presence of a toxic protein in CSF, the method comprising contacting the CSF of a subject in need thereof with an effective amount of a protease capable of removing or degrading the toxic protein.

The invention also provides for compositions comprising a) cerebrospinal fluid (CSF) of a subject having a neurological disorder characterized by the presence of a toxic protein in a toxic or pre-toxic form in CSF; and
b) a protease capable of degrading or removing the toxic protein in the toxic or pre-toxic form.

The selective degradation of a toxic protein in a toxic or pre-toxic form by the protease of the present invention is accomplished by a combination of substrate selectivity (proteases that preferentially recognize the toxic protein in the toxic or pre-toxic form of the protein), cleavage-site specificity (proteases that have specificity for cleaving the peptide bonds of the residue motifs encountered in the toxic protein in the toxic or pre-toxic form, substrate affinity (based on binding kinetics) and cleavage efficiency (rate of cleavage reaction). In certain embodiments of the invention, the protease is a mammalian, microbial (e.g., fungal, bacterial, or viral), or plant protease.

In certain embodiments, the protease is a serine protease. Exemplary mammalian serine proteases include trypsin, thrombin, elastase, kallikreins (KLK1-KLK15), tryptase a/b 1, chymotrypsin, cathepsin G, granzyme A, granzyme B, granzyme G, granzyme N, granzyme O, granzyme D, granzyme E, granzyme F, high temperature requirement serine protease A1 (HTRA1), matriptase 1, matriptase 2, matriptase 3, and hepsin. Exemplary bacterial serine proteases include subtilisin novo, subtilisin Carlsberg, Alcalase, Glutamyl endopeptidase, Endoproteinase Glu-C, Savirase, and Endoproteinase Lys-C. Exemplary fungal serine proteases include Proteinase K, and any one of the fungal proteases described in de Souza et al., *Brazilian J. of Microbiol.*, 46(2): 337-346 (2015), which can digest a dipeptide repeat protein of the present disclosure. Exemplary plant serine proteases include Benghalensin, HbSPA, HbSPB, and HbSPC. Exemplary viral serine proteases include HRV3C. For example, the serine protease can be chymotrypsin A, glutamyl endopeptidase I, DegP peptidase, lysyl endopeptidase, streptogrisin A, astrovirus serine peptidase. togavirin, IgA1-specific serine peptidase, flavivirin, subtilisin Carlsberg, kexin, prolyl oligopeptidase, dipeptidyl-peptidase IV, acylaminoacyl-peptidase, glutamyl endopeptidase C, carboxypeptidase Y, D-Ala-D-Ala carboxypeptidase A, D-Ala-D-Ala carboxypeptidase B, D-Ala-D-Ala peptidase C, peptidase Clp, Xaa-Pro dipeptidyl-peptidase, Lon-A peptidase, cytomegalovirus assembling, repressor LexA, signal peptidase I, signalase 21 kDa component, TraF peptidase, lysosomal Pro-Xaa carboxypeptidase, hepacivirin, potyvirus P1 peptidase, pestivirus NS3 polyprotein peptidase, equine arteritis virus serine peptidase, prolyl aminopeptidase, PS-10 peptidase, sobemovirus peptidase, luteovirus peptidase, C-terminal processing peptidase-1, tricorn core peptidase, penicillin G acylase precursor, dipeptidyl-peptidase 7, HetR putative peptidase, signal peptide peptidase A, protein C, archaean signal peptide peptidase 1, infectious pancreatic necrosis birnavirus Vp4 peptidase, dipeptidase E, sedolisin, rhomboid-1, SpoIVB peptidase, nucleoporin 145, influenza A PA peptidase, Ssy5 peptidase, picornain-like serine peptidase, murein tetrapeptidase LD-carboxypeptidase, PIDD auto-processing protein unit 1, Tellina virus 1 VP4, MUC1 self-cleaving, dystroglycan, gpO peptidase, *Escherichia coli* phage K1F endosialidase CIMCD self-cleaving protein, White bream virus serine peptidase, prohead peptidase gp21, prohead peptidase, CARD8 self-cleaving protein prohead peptidase gp175, destabilase, or autocrine proliferation repressor protein A. For example, in certain embodiments, the serine protease is trypsin, elastase or thrombin.

In certain embodiments, the protease is a threonine protease. Exemplary mammalian threonine proteases include proteasome catalytic subunits (1, 2, 3, 1i, 2i, 3i), proteasome beta (1, 2, 3, 4, 3-like) subunits, proteasome alpha (1-8, 3-like) subunits, taspase, and glycosylasparaginase.

In certain embodiments, the protease is an aspartic protease. Exemplary mammalian aspartic proteases include pepsin A, pepsin C, chymosin, cathepsin D, cathepsin E, napsin A, napsin B, b-secretase 1, b-secretase 2, presinilin 1, and presinilin 2. Exemplary bacterial aspartic proteases include signal peptidase II and prepilin. Exemplary fungal aspartic proteases include pepsin (A1), retropepsin (A2), and saccharopepsin. Exemplary plant aspartic proteases include nepenthisen. Exemplary viral aspartic proteases include retropepsin. For example, the aspartic protease can be pepsin, endothiapepsin, cathepsin D, cathepsin E, BACE1, BACE2, renin, napsin-A, nepenthesin, signal peptidase II, presinilin, GPR endopeptidase, Omptin, HIV-1 retropepsin, Ty3 transposon peptidase, Gypsy transposon peptidase, Osvaldo retrotransposon peptidase, cauliflower mosaic virus-type peptidase, bacilliform virus peptidase, thermopsin, spumapepsin, Copia transposon peptidase, Ty1 transposon peptidase, impas 1 peptidase, type 4 prepilin peptidase 1, FlaK peptidase, DNA-damage inducible protein 1, skin SASPase, HybD peptidase, PerP peptidase, sporulation factor SpoIIGA, or sso1175 g.p. For example in certain embodiments, the aspartic protease is pepsin or endothiapepsin.

In certain embodiments, the protease is a cysteine protease. Exemplary mammalian cysteine proteases include cathepsin B, cathepsin C, cathepsin F, cathepsin H, cathepsin K, cathepsin L, cathepsin L2, cathepsin O, cathepsin S, cathepsin W, cathepsin Z, cathepsin M, cathepsin Q, calpain 1, calpain 2, calpain 3, calpain 5, calpain 6, calpain 7, calpain 8, calpain 9, calpain 10, calpain 11, calpain 12, calpain 13, calpain 14, caspase 1, caspase 2, caspase 3, caspase 4, caspase 5, caspase 6, caspase 7, caspase 8, caspase 9, caspase 10, caspase 11, caspase 12, caspase 13, caspase 14, and asparagine endopeptidase AEP. Exemplary bacterial cysteine proteases include clostripain (Endoproteinase Arg-C) and gingapain. Exemplary fungal cysteine proteases include macrocypins. Exemplary plant cysteine proteases include papain and Bromelain. Exemplary viral cysteine proteases include adenovirus proteinase. The catalytic activity of certain cysteine proteases may be dependent upon the redox state. In certain embodiments, the cysteine protease is in an oxidized state (e.g., by placing in proximity to an oxidative agent). In certain embodiments, the cysteine protease is in a reduced state (e.g., by placing in proximity to an reducing agent). The oxidized enzyme may retain enough residual activity to be useful given, in particular, the very long treatment time (hours or days, for example) that could be employed in practice, compared to the very short timelines of chemical/enzymatic reactions (micro-seconds to even seconds), as well as the large amount of enzyme relative to substrate (approaching stoichiometric levels vs. substrate) that can be achieved. In certain embodiments, the oxidation time might be slow enough to retain significant levels of reduced enzyme.

In certain embodiments, the protease is a glutamic acid protease. Exemplary bacterial glutamic acid proteases include pepG1. Exemplary fungal glutamic acid proteases include proteases in the Eqolosins family (e.g., Scytalidoglutamic peptidase B).

In certain embodiments, the protease is a metalloprotease. Exemplary mammalian metalloproteases include aminopeptidase A, aminopeptidase B, aminopeptidase N, aminopeptidase PILS, aminopeptidase O, aminopeptidase Q, aminopeptidase B-like 1, stromelysin 1, matrilysin, meprin, ADAM (1-33), and neprilysin. Exemplary bacterial metalloproteases include thermolysin, neutrase, and endopeptidase Asp-N. Exemplary fungal metalloproteases include fungalysin and Mpr1. Exemplary plant metalloproteases include metzincins. The catalytic activity of a metalloprotease is dependent upon the presence of a metal ion in the protease, and leaching of the metal ion may result in a loss of the activity in an in situ method. Accordingly, in certain embodiments, the metalloprotease binds the metal ion with a dissociation constant ($K_D$) lower than (i.e., affinity greater than) $1 \times 10^{-11}$ M, $1 \times 10^{12}$ M, or $1 \times 10^{-13}$ M.

In certain embodiments, the protease is not a metalloprotease. For example, in certain embodiments, the protease is not thermolysin, carboxypeptidase A1, angiotensin-converting enzyme, aminopeptidase N, matrix metalloproteinase-1, cytosolic carboxypeptidase 6, eutrilysin, aminopeptidase P, glutamate carbodypeptidase II, pappalysin-1, site 2 peptidase, Atp23 peptidase, chloride channel accessory protein 1, Tiki 1 peptidase, or Spartan peptidase.

In certain embodiments the protease is not a cysteine protease. For example, in certain embodiments, the protease is not papain, bromelain, clostripain, cathepsin B, cathepsin C, cathepsin F, cathepsin H, cathepsin K, cathepsin L1, cathepsin L2, cathepsin O, cathepsin S, cathepsin W, cathepsin Z, catepcalpain 2, ubiquitinyl hydrolase-L1, streptopain, ubiquitinyl hydrolase-L1, ubiquitin-specific peptidase 14, aminophosphoribosyltransferase precursor, autophagin-1, Cezanne peptidase, otubain, CyID peptidase, caspase-1, OTLD1 deubiquitinylating enzyme, ataxin-3, acid ceramidase precursor, USPL1 peptidase, OTULIN peptidase, coagulation factor XIIIa, or MINDY-1 protein.

In certain embodiments, the protease is not an enzyme that is dependent on a non-covalently bound co-factor for proteolytic activity. For example, in certain embodiments, the protease is not serine protease factor VIIa.

Table 1 lists exemplary proteases that can be used in the method disclosed herein.

TABLE 1

Exemplary Proteases

| Protease | Amino Acid Sequence |
| --- | --- |
| Bovine trypsin | IVGGYTCAENSVPYQVSLNAGYHFCGGSLINDQWVVSAAHCYQY HIQVRLGEYNIDVLEGGEQFIDASKIIRHPKYSSWTLDNDILLIKLS TPAVINARVSTLLLPSACASAGTECLISGWGNTLSSGVNYPDLLQC LVAPLLSHADCEASYPGQITNNMICAGFLEGGKDSCQGDSGGPVA CNGQLQGIVSWGYGCAQKGKPGVYTKVCNYVDWIQETIAANS (SEQ ID NO: 1) |
| Human trypsin (mature form of Trypsinogen C) | IVGGYTCEENSVPYQVSLNSGSHFCGGSLISEQWVVSAGHCYKPH IQVRLGEHNIEVLEGNEQFINAAKIIRHPKYNRITLNNDIMLIKLST PAVINAHVSTISLPTAPPAAGTECLISGWGNTLSSGADYPDELQCL DAPVLTQAKCKASYPLKITSKMFCVGFLEGGKDSCQGDSGGPVV CNGQLQGIVSWGYGCAQKRRPGVYTKVYNYVDWIKDTIAANS (SEQ ID NO: 2) |
| Human trypsin (mature form of PRSS1) | IVGGYNCEENSVPYQVSLNSGYHFCGGSLINEQWVVSAGHCYKS RIQVRLGEHNIEVLEGNEQFINAAKIIRHPQYDRKTLDNDILLIKLS SPAVINSRVSAISLPTAPPAAGTESLISGWGNTLSSGADYPDELQCL DAPVLSQAECEASYPGKITNNMFCVGFLEGGKDSCQGDSGGPVV SNGELQGIVSWGYGCAQKNRPGVYTKVYNYVDWIKDTIAANS (SEQ ID NO: 3) |

TABLE 1-continued

Exemplary Proteases

| Protease | Amino Acid Sequence |
|---|---|
| Porcine pancreatic elastase | VVGGTEAQRNSWPSQISLQYRSGSSWAHTCGGTLIRQNWVMTA<br>AHCVDRELTFRVVVGEHNLNQNNGTEQYVGVQKIVVHPYWNTD<br>DVAAGYDIALLRLAQSVTLNSYVQLGVLPRAGTILANNSPCYITG<br>WGLTRTNGQLAQTLQQAYLPTVDYAICSSSSYWGSTVKNSMVC<br>AGGDGVRSGCQGDSGGPLHCLVNGQYAVHGVTSFVSRLGCNVT<br>RKPTVFTRVSAYISWINNVIASN<br>(SEQ ID NO: 4) |
| Mature human chymotrypsin-like elastase 1 (CELA1) | VVGGTEAGRNSWPSQISLQYRSGGSRYHTCGGTLIRQNWVMTAA<br>HCVDYQKTFRVVAGDHNLSQNDGTEQYVSVQKIVVHPYWNSDN<br>VAAGYDIALLRLAQSVTLNSYVQLGVLPQEGAILANNSPCYITGW<br>GKTKTNGQLAQTLQQAYLPSVDYAICSSSSYWGSTVKNTMVCAG<br>GDGVRSGCQGDSGGPLHCLVNGKYSVHGVTSFVSSRGCNVSRKP<br>TVFTQVSAYISWINNVIASN<br>(SEQ ID NO: 5) |
| Mature human chymotrypsin-like elastase 2A (CELA2A) | VVGGEEARPNSWPWQVSLQYSSNGKWYHTCGGSLIANSWVLTA<br>AHCISSSRTYRVGLGRHNLYVAESGSLAVSVSKIVVHKDWNSNQI<br>SKGNDIALLKLANPVSLTDKIQLACLPPAGTILPNNYPCYVTGWG<br>RLQTNGAVPDVLQQGRLLVVDYATCSSSAWWGSSVKTSMICAG<br>GDGVISSCNGDSGGPLNCQASDGRWQVHGIVSFGSRLGCNYYHK<br>PSVFTRVSNYIDWINSVIANN<br>(SEQ ID NO: 6) |
| Mature human chymotrypsin-like elastase 2B (CELA2B) | MLGGEEARPNSWPWQVSLQYSSNGQWYHTCGGSLIANSWVLTA<br>AHCISSSGIYRVMLGQHNLYVAESGSLAVSVSKIVVHKDWNSDQ<br>VSKGNDIALLKLANPVSLTDKIQLACLPPAGTILPNNYPCYVTGW<br>GRLQTNGALPDDLKQGQLLVVDYATCSSSGWWGSTVKTNMICA<br>GGDGVICTCNGDSGGPLNCQASDGRWEVHGIGSLTSVLGCNYYY<br>KPSIFTRVSNYNDWINSVIANN<br>(SEQ ID NO: 7) |
| Mature human chymotrypsin-like elastase 3A (CELA3A) | VVHGEDAVPYSWPWQVSLQYEKSGSFYHTCGGSLIAPDWVVTA<br>GHCISRDLTYQVVLGEYNLAVKEGPEQVIPINSEELFVHPLWNRS<br>CVACGNDIALIKLSRSAQLGDAVQLASLPPAGDILPNKTPCYITGW<br>GRLYTNGPLPDKLQQARLPVVDYKHCSRWNWWGSTVKKTMVC<br>AGGYIRSGCNGDSGGPLNCPTEDGGWQVHGVTSFVSAFGCNFIW<br>KPTVFTRVSAFIDWIEETIASH<br>(SEQ ID NO: 8) |
| Mature human chymotrypsin-like elastase 3B (CELA3B) | VVNGEDAVPYSWPWQVSLQYEKSGSFYHTCGGSLIAPDWVVTA<br>GHCISSSRTYQVVLGEYDRAVKEGPEQVIPINSGDLFVHPLWNRS<br>CVACGNDIALIKLSRSAQLGDAVQLASLPPAGDILPNETPCYITGW<br>GRLYTNGPLPDKLQEALLPVVDYEHCSRWNWWGSSVKKTMVC<br>AGGDIRSGCNGDSGGPLNCPTEDGGWQVHGVTSFVSAFGCNTRR<br>KPTVFTRVSAFIDWIEETIASH<br>(SEQ ID NO: 9) |
| Mature human cathepsin D light chain | GPIPEVLKNYMDAQYYGEIGIGTPPQCFTVVFDTGSSNLWVPSIHC<br>KLLDIACWIHHKYNSDKSSTYVKNGTSFDIHYGSGSLSGYLSQDT<br>VSVPCQS<br>(SEQ ID NO: 10) |
| Mature human cathepsin D heavy chain | LGGVKVERQVFGEATKQPGITFIAAKFDGILGMAYPRISVNNVLP<br>VFDNLMQQKLVDQNIFSFYLSRDPDAQPGGELMLGGTDSKYYKG<br>SLSYLNVTRKAYWQVHLDQVEVASGLTLCKEGCEAIVDTGTSLM<br>VGPVDEVRELQKAIGAVPLIQGEYMIPCEKVSTLPAITLKLGGKG<br>YKLSPEDYTLKVSQAGKTLCLSGFMGMDIPPPSGPLWILGDVFIG<br>RYYTVFDRDNNRVGFAEAARL<br>(SEQ ID NO: 11) |
| Human kallikrein-5 | VTEHVLANNDVSCDHPSNTVPSGSNQDLGAGAGEDARSDDSSSRI<br>INGSDCDMHTQPWQAALLLRPNQLYCGAVLVHPQWLLTAAHCR<br>KKVFRVRLGHYSLSPVYESGQQMFQGVKSIPHPGYSHPGHSNDL<br>MLIKLNRRIRPTKDVRPINVSSHCPSAGTKCLVSGWGTTKSPQVH<br>FPKVLQCLNISVLSQKRCEDAYPRQIDDTMFCAGDKAGRDSCQG<br>DSGGPVVCNGSLQGLVSWGDYPCARPNRPGVYTNLCKFTKWIQE<br>TIQANS<br>(SEQ ID NO: 12) |

TABLE 1-continued

Exemplary Proteases

| Protease | Amino Acid Sequence |
|---|---|
| Human kallikrein-6 | LVHGGPCDKTSHPYQAALYTSGHLLCGGVLIHPLWVLTAAHCKK PNLQVFLGKHNLRQRESSQEQSSVVRAVIHPDYDAASHDQDIMLL RLARPAKLSELIQPLPLERDCSANTTSCHILGWGKTADGDFPDTIQ CAYIHLVSREECEHAYPGQITQNMLCAGDEKYGKDSCQGDSGGP LVCGDHLRGLVSWGNIPCGSKEKPGVYTNVCRYTNWIQKTIQAK (SEQ ID NO: 13) |

In certain embodiments, the protease comprises an amino acid sequence at least 80% (e.g., at least 85%, at least 90%, at least 91%, at least 92%, at least 93%, at least 94%, at least 95%, at least 96%, at least 97%, at least 98%, or at least 99%) identical to any one of SEQ ID NOs: 1-13. In certain embodiments, the protease comprises an amino acid sequence selected from the group consisting of SEQ ID NOs: 1-13. In certain embodiments, the amino acid sequence of the protease consists of a sequence selected from the group consisting of SEQ ID NOs: 1-13.

In certain embodiments, the protease is a trypsin. In certain embodiments, the protease comprises an amino acid sequence at least 80% (e.g., at least 85%, at least 90%, at least 91%, at least 92%, at least 93%, at least 94%, at least 95%, at least 96%, at least 97%, at least 98%, or at least 99%) identical to SEQ ID NO:1, SEQ ID NO:2, or SEQ ID NO:3. In certain embodiments, the protease comprises the amino acid sequence set forth in SEQ ID NO:1, SEQ ID NO:2, or SEQ ID NO:3. In certain embodiments, the amino acid sequence of the protease consists of the sequence set forth in SEQ ID NO:1, SEQ ID NO:2, or SEQ ID NO:3.

In certain embodiments, the protease is an elastase. In certain embodiments, the protease comprises an amino acid sequence at least 80% (e.g., at least 85%, at least 90%, at least 91%, at least 92%, at least 93%, at least 94%, at least 95%, at least 96%, at least 97%, at least 98%, or at least 99%) identical to SEQ ID NO:4, SEQ ID NO:5, SEQ ID NO:6, SEQ ID NO:7, SEQ ID NO:8, or SEQ ID NO:9. In certain embodiments, the protease comprises the amino acid sequence set forth in SEQ ID NO:4, SEQ ID NO:5, SEQ ID NO:6, SEQ ID NO:7, SEQ ID NO:8, or SEQ ID NO:9. In certain embodiments, the amino acid sequence of the protease consists of the sequence set forth in SEQ ID NO:4, SEQ ID NO:5, SEQ ID NO:6, SEQ ID NO:7, SEQ ID NO:8, or SEQ ID NO:9.

In certain embodiments, the protease is a cathepsin D. In certain embodiments, the protease comprises a first polypeptide chain comprising an amino acid sequence at least 80% (e.g., at least 85%, at least 90%, at least 91%, at least 92%, at least 93%, at least 94%, at least 95%, at least 96%, at least 97%, at least 98%, or at least 99%) identical to SEQ ID NO:10 and a second polypeptide chain comprising an amino acid sequence at least 80% (e.g., at least 85%, at least 90%, at least 91%, at least 92%, at least 93%, at least 94%, at least 95%, at least 96%, at least 97%, at least 98%, or at least 99%) identical to SEQ ID NO:11. In certain embodiments, the protease comprises a first polypeptide chain comprising the amino acid sequence set forth in SEQ ID NO:10 and a second polypeptide chain comprising the amino acid sequence set forth in SEQ ID NO:11. In certain embodiments, the amino acid sequence of the first polypeptide chain consists of the sequence set forth in SEQ ID NO:10 and the amino acid sequence of the second polypeptide chain consists of the sequence set forth in SEQ ID NO:11.

In certain embodiments, the protease is a kallikrein. In certain embodiments, the protease comprises an amino acid sequence at least 80% (e.g., at least 85%, at least 90%, at least 91%, at least 92%, at least 93%, at least 94%, at least 95%, at least 96%, at least 97%, at least 98%, or at least 99%) identical to SEQ ID NO:12 or SEQ ID NO:13. In certain embodiments, the protease comprises the amino acid sequence set forth in SEQ ID NO:12 or SEQ ID NO:13. In certain embodiments, the amino acid sequence of the protease consists of the sequence set forth in SEQ ID NO:12, or SEQ ID NO:13.

In certain embodiments, the protease is immobilized on the solid support at a concentration of about 1 mg/ml to about 10 mg/ml (e.g., 1-9 mg/ml, 1-8 mg/ml, 1-7 mg/ml, 1-6 mg/ml, 1-5 mg/ml, 1-4 mg/ml, 1-3 mg/ml, 1-2 mg/ml, 2-10 mg/ml, 3-10 mg/ml, 4-10 mg/ml, 5-10 mg/ml, 6-10 mg/ml, 7-10 mg/ml, 8-10 mg/ml, 9-10 mg/ml, about 2 mg/ml, about 3 mg/ml, about 4 mg/ml, about 5 mg/ml, about 6 mg/ml, about 7 mg/ml, about 8 mg/ml, about 9 mg/ml, or about 10 mg/ml).

In certain embodiments, the protease is able to reduce the concentration of a toxic protein in a toxic or pre-toxic form (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein) in the CSF by 20% or more (e.g., by 30% or more, by 40% or more, by 50% or more, by 60% or more, by 70% or more, by 80% or more, by 90% or more, by 95% or more, by 99% or more) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

In certain embodiments, the protease can reduce the concentration of a toxic or pre-toxic form of the toxic protein (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein) below 1000 ng/mL (e.g., below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

In certain embodiments, the protease is capable of effecting the degradation of a toxic or pre-toxic form of the toxic protein (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein) without significant effects on the concentration of proteins naturally occurring in the CSF. The selective degradation of a toxic or pre-toxic form of the toxic protein by the protease of the present invention is accomplished by a combination of substrate selectivity (proteases that preferentially recognize the toxic protein in a toxic or pre-toxic form), cleavage-site specificity (proteases that have specificity for cleaving the peptide bonds of the residue motifs encountered in a toxic or pre-toxic form of the toxic protein, substrate affinity (based on binding kinetics) and cleavage efficiency (rate of cleavage reaction).

In certain embodiments, the proteases used for performing the method are characterized by an active site capable of selectively recognizing the peptide sequence of a toxic or pre-toxic form of the toxic protein (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein) over other proteins normally occurring in the CSF.

In certain embodiments the proteases of the present invention are further capable of higher specificity for the cleavage of at least one peptide bond of a toxic or pre-toxic form of the toxic protein (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein) over cleavage of peptide bonds of proteins normally occurring in the CSF.

There are numerous methods available in the art for assessing the specificity of a protease toward different peptide substrates, including Forster/fluorescence resonance energy transfer (FRET), immunocapture, combinations of FRET and enzyme-linked immunosorbent assay (ELISA) based assays, chromatography, combinatorial substrate libraries, use of fluorogenic substrates and labeling techniques. For a review on techniques available for assessing the specificity of proteases see, for example Poreba and Drag, *Curr. Med. Chem.* 2010, 17 (33), 3968-3995 and Diamond, *Curr. Opin. Chem. Biol.* 2007, 11 (1), 46-51.

In certain embodiments of the invention the protease has higher specificity and lower affinity for a toxic or pre-toxic form of the toxic protein (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein) compared to proteins normally occurring in the CSF.

In another embodiment, the protease has higher specificity and higher affinity for a toxic or pre-toxic form of the toxic protein (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein) compared to proteins normally occurring in the CSF.

The affinity of the protease for the substrate can be measured by methods well known in the art, for example by determining the $K_{on}$ and $K_{off}$ rates using surface plasmon resonance.

In certain embodiments of the invention, the protease has higher efficiency cleaving at least one peptide bond of a toxic or pre-toxic form of the toxic protein (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein) compared to the peptide bonds of proteins normally occurring in the CSF.

The efficiency of the protease ($k_{cat}/K_m$) can be determined through enzyme kinetics assays well known in the art, for example spectrophotometric assays, radiometric assays, fluorometric assays, calorimetric assays, light scattering assays, microscale thermophoresis and chromatographic assays. For an overview of enzyme assays that can be used to determine enzyme (e.g., protease) kinetics see, for example Bisswanger, *Practical Enzymology* ($2^{nd}$ edition), Wiley-Blackwell, Weinheim, 2001.

In certain embodiments, the protease is not more selective in cleaving a toxic or pre-toxic form of the toxic protein (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein) over other proteins (e.g., proteins normally present in the CSF).

In certain embodiments, the protease is selected from the group consisting of endopeptidases (e.g., endopeptidase K), matrix metallopeptidases (MMP) MMP-2, MMP-3, MMP-9, MMP-10), matrix glutamyl endopeptidases (e.g., matrix glutamyl endopeptidase I), trypsin, thrombin, proteinase K, elastase, Factor Xa, kallikreins (e.g., kallikrein-6, kallikrein-5), clostripains, calpains (e.g., calpain-1, calpain-2), cathepsins (e.g., cathepsin-B, cathepsin-D, cathepsin G, cathepsin L, cathepsin S), caspases (e.g., caspase-1, caspase-2, caspase-3, caspase-6, caspase-7, caspase-8, caspase-12), granzymes (e.g. granzyme A, granzyme M), meprin alpha, meprin beta, astacin, RC1339, peptidyl-LYS metallopeptidase, LAST peptidase (e.g., Limulus-type), LAST MAM peptidase (e.g., Limulus type), chymotrypsin (e.g., cattle-type), HIV-1 retropepsin and thermolysin. In one embodiment (e.g., if the toxic protein, in a toxic form or a pre-toxic form, is alpha-synuclein), the protease is selected from endopeptidases (e.g., endopeptidase K), matrix metallopeptidases (MMP) (e.g., MMP-1, MMP-3, MMP-9), calpains (e.g., calpain-1, calpain-2), trypsin, cathepsins (e.g., cathepsin-D). In one embodiment (e.g. if the toxic protein, in a toxic form or a pre-toxic form, is huntingtin), the protease is selected from matrix metallopeptidases (MMP) (e.g., MMP-10), calpains (e.g., calpain-1, calpain-2), caspases (e.g., caspase-2, caspase-3, caspase-6). In one embodiment (e.g., if the protein is toxic FUS), the protease is selected from the group consisting of cathepsins (e.g., cathepsin B, cathepsin L), granzymes (e.g., granzyme M), astacin, RC1339 (Rickettsia conorii), peptidyl-LYS metallopeptidase, trypsin and meprin beta). In one embodiment (e.g., if the toxic protein, in a toxic form or a pre-toxic form, is a TDP-43 protein) the protease is selected from the group consisting of cathepsins (e.g., cathepsin L, cathepsin S), matrix metallopeptidases (MMP) (e.g., MMP-2), caspases (e.g., caspase-3, caspase-7, caspase 12), granzymes (e.g., granzyme M) and trypsin. In one embodiment (e.g., if the toxic protein, in a toxic form or a pre-toxic form, is a SOD protein), the protease is selected from the group consisting of matrix metalloproteases (MMP) (e.g., MMP-2), cathepsins (e.g., cathepsin B, cathepsin G, cathepsin L, cathepsin S), LAST peptidase (e.g., Limulus-type), LAST MAM peptidase (e.g., Limulus-type), glutamyl endopeptidases (e.g., glutamyl endopeptidase I), peptidyl-Lys metallopeptidase, HIV-1 retropepsin, caspases (e.g., caspase-1, caspase-2), trypsin, chymotrypsin (e.g., cattle-type), elastase and meprin alpha. In one embodiment (e.g. if the toxic protein, in a toxic or a pre-toxic form, is a tau protein), the protease is selected from the group consisting of calpains (e.g., calpain-2), caspases (e.g., caspase-1, caspase-3, caspase-6, caspase-7, caspase-8), granzymes (e.g., granzyme A), trypsin, and meprin alpha.

In certain embodiments of the invention, the toxic protein (in a toxic form or a pre-toxic form) is tau and the protease is selected from the group consisting of trypsin, thrombin, proteinase K, elastase, Factor Xa, kallikreins (e.g., kallikrein-6, kallikrein-5), clostripains, calpains, cathepsins (e.g., cathepsin-B) and thermolysin. In certain embodiments, the toxic protein (in a toxic form or a pre-toxic form) is tau and the protease is selected from the group consisting of calpains (e.g., calpain-2), caspases (e.g., caspase-1, caspase-3, caspase-6, caspase-7, caspase-8), granzymes (e.g., granzyme A), trypsin, and meprin alpha.

In certain embodiments of the invention, the toxic protein (in a toxic form or a pre-toxic form) is α-synuclein and the protease is selected from the group consisting of trypsin, thrombin, proteinase K, elastase, Factor Xa, kallikreins (e.g., kallikrein-6, kallikrein-5), clostripains, calpains, cathepsins (e.g., cathepsin-B) and thermolysin. In certain embodiments, the toxic protein (in a toxic form or a pre-toxic form) is α-synuclein and the protease is selected from the group consisting of calpains (e.g., calpain-2), caspases (e.g., caspase-1, caspase-3, caspase-6, caspase-7, caspase-8), granzymes (e.g., granzyme A), trypsin, and meprin alpha.

In certain embodiments, the protease is a cysteine protease (e.g., clostripains, cathepsins and calpains) activated with a reducing agent (e.g., DTT). In certain embodiments, the protease is a cysteine protease (e.g., clostripains, cathepsins and calpains) in the absence of reducing agents.

In certain embodiments of the invention, the protease of the treatment method is a protease naturally occurring in CSF. In a further embodiment, the protease is kallikrein (e.g., kallikrein-6 (neurosin) or kallikrein-5). In certain embodiments kallikrein-6 is in a proform and activated by lysyl endopeptidase before or during use in the methods of treatment of the present disclosure.

Solid Supports

Some embodiments of the present invention provide for the use of immobilized agents (e.g., immobilized enzymes, e.g., immobilized proteases). Advantages of using immobilized agents would be readily apparent to those skilled in the art and comprise ease of manipulation, increased thermal and operational stability, decreased sensitivity to reaction conditions (e.g., pH and temperature), resistance to aggregation, resistance to autodigestion and digestion by other proteases and ease of separation from reaction mixtures.

A variety of modalities for immobilizing biological agents (e.g., enzymes, e.g., proteases) are known in the art and include, without being limited to, affinity-binding to porous materials such as beads and membranes using protein tags, adsorption on porous beads (e.g., glass or alginate beads), adsorption onto membranes, adsorption into matrices and covalent bonding to insoluble supports (e.g., silica gel, e.g., resins), porous support (e.g., porous beads) or membranes. In certain embodiments the biological agents (e.g., enzymes, e.g., proteases) are immobilized on (e.g., by covalent binding to) cross-linked resins. In certain embodiments the biological agents (e.g., enzymes, e.g., proteases) are immobilized on (e.g., by covalent binding to) porous beads (e.g. porous resin beads). In further embodiments, the biological agents (e.g., enzymes, e.g., proteases) are immobilized on (e.g., by covalent binding to) cross-linked agarose resins (e.g. 4% or 6% cross-linked agarose resins). For example, the biological agents (e.g., enzymes, e.g., proteases) can be immobilized on porous cross-linked agarose resin beads. In certain embodiments, the agarose resin is an NHS-activated agarose that can be covalently attached to a primary amine. In another embodiment, the agarose resin comprises aldehyde-activated agarose beads for covalent coupling of via primary amines (e.g., AminoLink™ Plus Coupling Resin). In another embodiment the agarose resin is a CDI-activated agarose resin (e.g., Pierce™ resin) that can immobilize proteins that contain N-nucleophiles; pH9-11 O/N reaction. In another embodiment the agarose resin is a resin that can react with sulfhydryl groups to form irreversible thioether bonds (e.g., SulfoLink™ Coupling Resin). In certain embodiments, the biological agents (e.g., enzymes (e.g., proteases)) are immobilized on beads made with a reactive epoxide functionality to react with amines or activated amines to bind enzymes (e.g., proteases) covalently. Beads can be functionalized with reactive entities such as, amongst others, epoxides or succinimides, which can react with enzymes containing free amine groups to form active stable covalently linked immobilized enzyme products.

In certain embodiments, a protease can be immobilized on a solid support (e.g., beads) at a concentration of about 1 mg/ml to about 10 mg/ml (e.g., 1-9 mg/ml, 1-8 mg/ml, 1-7 mg/ml, 1-6 mg/ml, 1-5 mg/ml, 1-4 mg/ml, 1-3 mg/ml, 1-2 mg/ml, 2-10 mg/ml, 3-10 mg/ml, 4-10 mg/ml, 5-10 mg/ml, 6-10 mg/ml, 7-10 mg/ml, 8-10 mg/ml, 9-10 mg/ml, about 2 mg/ml, about 3 mg/ml, about 4 mg/ml, about 5 mg/ml, about 6 mg/ml, about 7 mg/ml, about 8 mg/ml, about 9 mg/ml, or about 10 mg/ml). For example, In certain embodiments, the protease can be immobilized on the solid support at a concentration of about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, or about 10 mg/ml. In certain embodiments, the biological agents (e.g., enzymes (e.g., proteases)) are immobilized (at a concentration of about 1 mg/ml to about 10 mg/ml (e.g., 1-9 mg/ml, 1-8 mg/ml, 1-7 mg/ml, 1-6 mg/ml, 1-5 mg/ml, 1-4 mg/ml, 1-3 mg/ml, 1-2 mg/ml, 2-10 mg/ml, 3-10 mg/ml, 4-10 mg/ml, 5-10 mg/ml, 6-10 mg/ml, 7-10 mg/ml, 8-10 mg/ml, 9-10 mg/ml, about 2 mg/ml, about 3 mg/ml, about 4 mg/ml, about 5 mg/ml, about 6 mg/ml, about 7 mg/ml, about 8 mg/ml, about 9 mg/ml, or about 10 mg/ml) on beads made with a reactive epoxide functionality to react with amines or activated amines to bind enzymes (e.g., proteases) covalently.

In certain embodiments, the biological agents (e.g., enzymes, e.g., proteases) can be immobilized by precipitation either as amorphous or as crystalline precipitates. Furthermore, the precipitates can be cross-linked to form, for example, cross-linked enzyme (e.g., protease) crystals or cross-liked amorphous precipitates.

In certain embodiments, the precipitates (e.g., amorphous precipitates, e.g., crystalline precipitate) and cross-linked precipitates (e.g., cross-linked amorphous precipitates, e.g., cross-linked crystalline precipitates) can form porous matrices with a controlled pore size, wherein the pores can function as size exclusion filters to further enhance the selectivity of the agent (e.g., protease) for a toxic form or a pre-toxic form of the toxic protein (e.g., a tau protein (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein) over other proteins naturally occurring in the CNS.

In certain embodiments the lyophilized agent (e.g., the lyophilized enzyme, e.g., the lyophilized protease) is encapsulated in a porous coating designed to be permeable to the substrate, generating agent-containing "beads." In certain embodiments, the size of the pores in the porous coating is designed to function as size exclusion filters to further enhance the selectivity of the agent (e.g., protease) for a toxic form or a pre-toxic form of the toxic protein (e.g., a tau protein (e.g., tau protein aggregates, tau protein tangles, tau oligomers, hyperphosphorylated tau proteins, soluble tau proteins, tau dimers)) over other proteins naturally occurring in the CNS.

Patient Diagnosing and Monitoring

The present invention provides a method for diagnosing a neurological disorder in a subject that is susceptible to a treatment, wherein the treatment comprises contacting the CSF of the subject with an agent (e.g., an enzyme, e.g., an antibody) capable of removing or degrading a toxic protein in a toxic or pre-toxic form, said method comprising:

a). determining, having determined, or receiving information regarding the presence, amount, and/or form of a toxic protein (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein) in the CSF of the subject;

b). upon determining, having determined, or receiving information of the presence, amount, and/or form of the toxic protein in the CSF of the subject (e.g., present in a higher amount or concentration compared to a healthy subject), diagnosing the subject as susceptible to the treatment.

The presence and/or amount of a toxic protein (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein) in the CSF of the subject can be evaluated by methods known in the art (e.g., antibody based detection methods (e.g., immunoassays (e.g., ELISA)), immunoaffinity coupled with LC/MS methods, targeted mass spectrometry (e.g., mass spectrometry detection of proteotypic peptides (e.g., tau proteotypic peptides)). The form of a toxic protein (e.g., amino acid sequence of the isoform, post-translational modifications, soluble protein, insoluble protein, protein monomer, protein aggregate, protein tangles, protein oligomer, protein fibril, hyperphosphorylated protein, or misfolded protein) in the CSF of the subject can also be evaluated by methods known in the art (e.g., size-exclusion chromatography, western blotting (to detect certain post-translational modifications such as hyperphosphorylation), and immunoassays). In certain embodiments, the toxic protein is detected in a toxic form (e.g., protein aggregate, protein tangles, protein oligomer, protein fibril, hyperphosphorylated protein, or misfolded protein). In certain embodiments, the toxic protein is detected in a pre-toxic form.

The present invention also provides a method for predicting the efficacy of a treatment of a neurological disorder in a subject, the treatment comprising contacting the CSF of the subject with an agent (e.g., an enzyme, e.g., an antibody) capable of removing or degrading a toxic or pre-toxic form of a toxic protein (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein) said method comprising:

determining, having determined or receiving information regarding the presence, amount, and/or form of a toxic protein (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein) in the CSF of the subject wherein the said determining, having determined or receiving information of the presence, amount, and/or form of a toxic protein in the subject's CSF is predictive of efficacy of the treatment.

The present invention further provides a method for diagnosing and treating a neurological disorder in a subject, wherein the method comprises:

a) determining, having determined or receiving information regarding the presence of a toxic protein, in a toxic or pre-toxic form, in the CSF of the subject; and if the subject has been determined to have a toxic protein at a certain amount or in a certain form in the CSF, diagnosing the subject as susceptible to the treatment of step b;

b) treating the subject diagnosed as susceptible in step a) by contacting the cerebrospinal fluid (CSF) of the subject with a protease capable of removing or degrading the toxic or pre-toxic form of the toxic protein.

In certain embodiments, the presence, amount, and/or form of a toxic protein (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein) is determined by analyzing a biological sample from the subject (e.g., a CSF sample). In a further embodiment, the presence and/or amount of protein in the biological sample is determined by methods such as antibody based detection methods (e.g., immunoassays (e.g., ELISA), immunoaffinity coupled with LC/MS methods, targeted mass spectrometry (e.g., mass spectrometry detection of proteotypic peptides (e.g., tau proteotypic peptides)). The form of a toxic protein (e.g., amino acid sequence of the isoform, post-translational modifications, soluble protein, insoluble protein, protein monomer, protein aggregate, protein tangles, protein oligomer, protein fibril, hyperphosphorylated protein, or misfolded protein) in the CSF of the subject can also be evaluated by methods known in the art (e.g., size-exclusion chromatography, western blotting (to detect certain post-translational modifications such as hyperphosphorylation), and immunoassays).

Patient Sample

The terms "patient sample," "subject sample," "biological sample," and "sample" are used interchangeably herein. The subject sample can be a tissue, or bodily fluid, or bodily product. Tissue samples can include fixed, paraffin embedded, fresh, or frozen samples. For example, the tissue sample can include a biopsy or a cheek swab. Exemplary tissues include nervous tissue, brain, skin and hair follicles. Exemplary samples include blood samples and cerebrospinal fluid samples.

Exemplary bodily fluids include blood, plasma, urine, lymph, tears, sweat, saliva, semen, and cerebrospinal fluid. Exemplary bodily products include exhaled breath.

The tissue, fluid or product can be removed from the patient and analyzed. The evaluation can include one or more of: performing the analysis of the tissue, fluid or product; requesting analysis of the tissue fluid or product; requesting results from analysis of the tissue, fluid or product; or receiving the results from analysis of the tissue, fluid or product.

The sample, tissue, fluid or product can be analyzed for the presence, amount, and/or form of a toxic protein (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein).

Methods of Evaluating Samples

Evaluating Samples for Genetic Mutations

The presence of a mutation in a gene associated with a neurological disorder can be assessed using any of a wide variety of well-known methods for detecting expression of a transcribed molecule, gene, protein, mRNA, genomic DNA, or cDNA. Non-limiting examples of such methods include nucleic acid hybridization-based methods, amplification-based methods, microarray analysis, flow cytometry analysis, DNA sequencing, next generation sequencing, repeat-primed PCR, fluorescent fragment length assays, capillary sequencing, primer extension, PCR, in situ hybridization, dot blot, and Southern blot.

Evaluating Samples for the Presence of Toxic Proteins

The methods described herein can pertain to the evaluation of a patient sample for the presence of a toxic protein in a toxic or pre-toxic form (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein). The presence and amount of a toxic or pre-toxic form of a toxic protein associated with a neurological disorder (e.g., ALS, FTLD, FTD) can be assessed using any of a variety of methods available in the art for detecting and quantifying proteins and/or protein fragments including, but not restricted to antibody based detection methods (e.g., immunoassays (e.g., ELISA), immunoaffinity coupled with LC/MS methods, targeted mass spectrometry (e.g., mass spectrometry detection of proteotypic peptides (e.g., tau proteotypic peptides)).

In certain embodiments, the sample to be analyzed is cerebrospinal fluid (CSF).

In certain embodiments, a toxic or pre-toxic form of the toxic protein can be detected using an immunoassay. As used herein, immunoassays include assays that utilize an antibody to specifically bind to a protein or polypeptide. The polypeptide can be detected and/or quantified using any of a number of well recognized immunological binding assays (see, e.g., U.S. Pat. Nos. 4,366,241; 4,376,110; 4,517,288; and 4,837,168). For a review of the general immunoassays, see also Asai (1993) *Methods in Cell Biology* Volume 37: *Antibodies in Cell Biology*, Academic Press, Inc. New York; Stites & Terr (1991) *Basic and Clinical Immunology* 7th Edition. Immunoassays for the detection and/or quantification of a protein or polypeptide can take a wide variety of formats well known to those of skill in the art.

An antibody capable of binding to a protein or polypeptide, e.g., an antibody with a detectable label (either directly or indirectly labeled), can be used to detect a toxic protein in a toxic or pre-toxic form.

In certain embodiments, a toxic or pre-toxic form of the toxic protein (e.g., tau (e.g., tau protein aggregates, tau protein tangles, tau oligomers, hyperphosphorylated tau proteins, soluble tau proteins, tau dimers) can be detected and quantified by mass-spectrometry coupled with liquid chromatography either as the full-length protein or as protein digestion products (e.g., proteotypic peptides (e.g., tau proteotypic peptides)).

Kits

Described herein are kits comprising a means to treat the CSF of a subject diagnose as having a neurological disease characterized by the presence of a toxic protein in a toxic or pre-toxic form (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein). For example, the kit can include a suitably formulated protease capable to degrade or remove a toxic or pre-toxic form of the toxic protein from the CSF of a subject. The kit can also include means to remove the CSF from the subject for the purpose of contacting it with the agent, means to separate the agent from the CSF after completion of the treatment and means to reintroduce the treated CSF back into the subject. The kit can also include instructions for performing the treatment of the CSF with the provided agent.

Also described herein are kits comprising a means to assay the presence of a toxic protein, in a toxic or pre-toxic form (e.g., tau (e.g., tau protein aggregates, tau protein tangles, tau oligomers, hyperphosphorylated tau proteins, soluble tau proteins, tau dimers), α-synuclein, TDP-43, FUS/TLS, SOD1, β-amyloid, Huntingtin protein (HTT) (e.g., with glutamate repeats), or a prion protein), in the CSF of a subject. For example, the kit can include an agent or a plurality of agents (e.g., a monoclonal or polyclonal antibody or a plurality of monoclonal or polyclonal antibodies with a detectable label) capable of interacting specifically with one or more of the toxic proteins (in toxic or pre-toxic forms) and means to detect the presence of the labeled antibody-protein conjugate.

EXAMPLES

Example 1—Titration of Protease Activity

This example shows a titration of protease activity for elastase, cathepsin G, and trypsin using casein as the reaction substrate.

1.0 mg/ml stock solution of Bodipy®-labelled casein was prepared in phosphate buffered saline (PBS) then diluted to 10 µg/ml in digestion buffer (10 mM Tris-HCl, pH 7.8, 0.1 mM NaN$_3$). Elastase, cathepsin G, or trypsin were diluted in digestion buffer at various concentrations and 100 µl of diluted protease was added to each well of a 96-well microplate. 100 µl of 10 µg/ml Bodipy®-labelled casein was added to each sample well and incubated for 1 hour, protected from light. Following incubation, the microplate was read using a fluorescence microplate reader.

As shown in FIG. 1, elastase, cathepsin G, and trypsin enzyme preparations exhibited casein-digestion activity having linear reaction kinetics up to approximately 6 µg/ml of each protease.

Example 2—Digestion Activity of Proteases Immobilized on Agarose Resin Columns

This example shows the protease activity for elastase, cathepsin G, and trypsin immobilized on NETS-activated agarose resin, using casein as the reaction substrate.

NETS-activated agarose resin columns were prepared according to the manufacturer's instructions. The columns included 100 μl of pre-washed agarose resin with 200 μl of control buffer, or 2 mg/ml of elastase, cathepsin G, trypsin, kallikrein-5 (KLK5), or kallikrein-6 (KLK6) activated by lysyl endopeptidase. Columns were spun and flow-through was collected to determine the efficiency of protease immobilization. No protein was detected in flow through as determined by Bradford assay (data not shown). Low protease activity was detected in the flow-through (determined by a protease activity assay as described in Example 1) indicating a coupling efficiency of >99.9%. The remaining free NGS sites were blocked by adding 1 M ethanolamine in PBS.

Figure 2A:
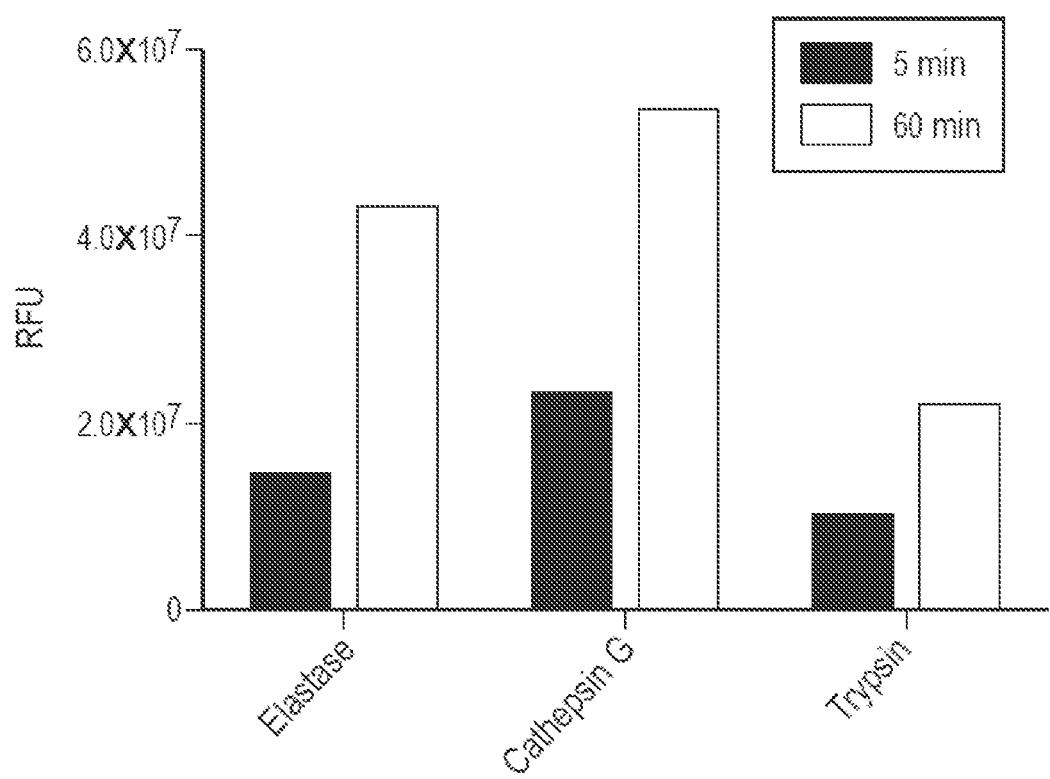
FIG. 2A is a bar graph showing the casein-digestion activity of elastase, cathepin G, and trypsin immobilized on agarose resin columns. RFU represents relative fluroscense unit.
Figure 2B:
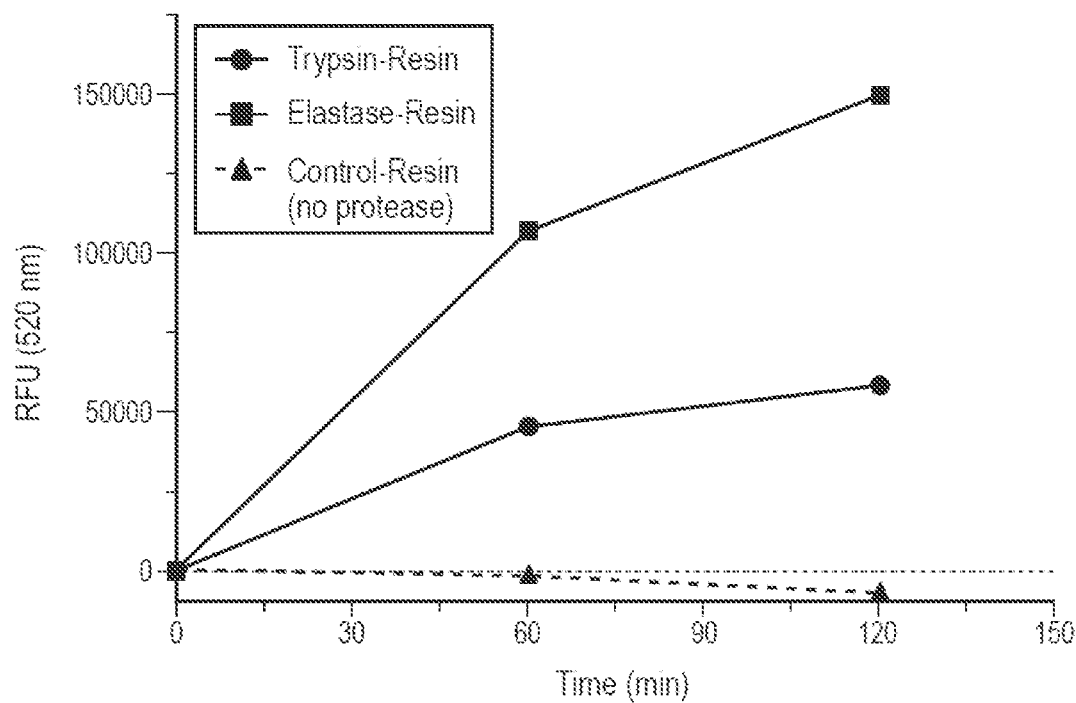
FIG. 2B is a line graph showing the casein-digestion activity of elastase and trypsin immobilized on agarose resin columns. The results are corrected from the control (no protease) resin group. RFU represents relative fluroscense unit.
Figure 2C:
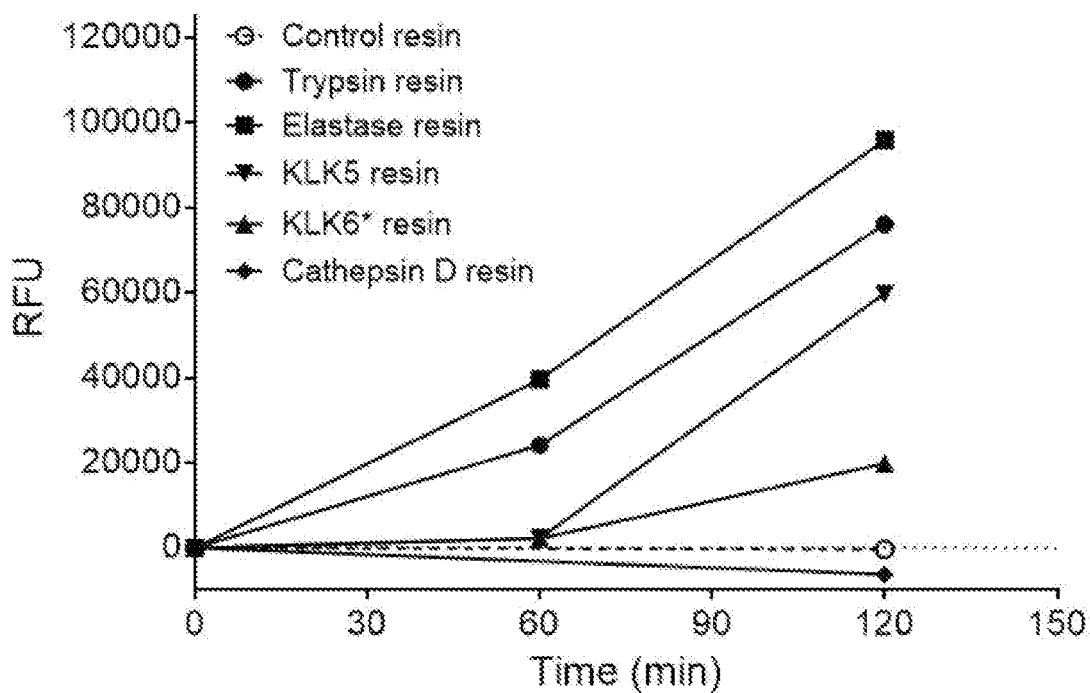
FIG. 2C is a line graph showing the casein-digestion activity of trypsin, elastase, kallikrein-5 (KLK5), or kallikrein-6 (KLK6) activated by lysyl endopeptidase (as shown in the figure, KLK6*) immobilized on agarose resin columns. The results are corrected from the control (no protease) resin group. RFU represents relative fluroscense unit.

To determine the activity of proteases immobilized on the agarose resin, 100 μl of 10 μg/ml of Bodipy®-labelled casein was added to each column and incubated at room temperature for 5, 60, or 120 minutes with inversion. Following incubation, columns were centrifuged and samples removed for fluorescence measurement. As shown in FIG. 2A, immobilized elastase, cathepsin G, and trypsin exhibited casein-digestion activity at 5 minute and 60 minute incubation times. As shown in FIG. 2B, elastase and trypsin exhibited casein-digestion activity at 60 minute and 120 minute incubation times. As shown in FIG. 2C, KLK5 and KLK6 also exhibited casein-digestion activity at 120 minute incubation time.

Figure 2D:
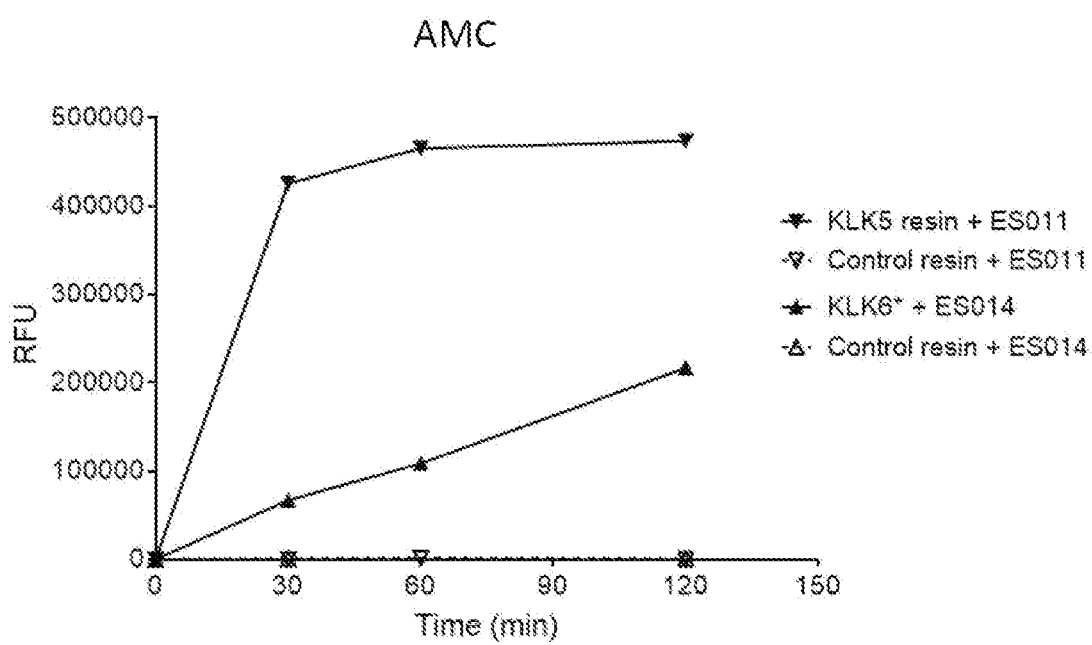
FIG. 2D is a line graph showing the activity of KLK5 and KLK6 activated by lysyl endopeptidase (as shown in the figure, KLK6*) immobilized on agarose resin columns to digest peptide substrates Boc-VPR-AMC (ES011) and Boc-QAR-AMC (ES014), respectively. RFU represents relative fluroscense unit.

To further confirm the activity of KLK5 and KLK6, fluorogenic peptide substrates Boc-VPR-AMC (ES011) and Boc-QAR-AMC (ES014) were used. These peptide substrates include cleavage sites for KLK5 and KLK6, respectively. After incubation of the protease with its respective substrate for 30, 60, or 120 minutes in HBSS buffer, columns were centrifuged and samples removed for fluorescence measurement. As shown in FIG. 2D, KLK5 and KLK6 exhibited protease activity at all time points tested.

Example 3—Digestion of Tau, α-Synuclein, and TDP-43 by Proteases Immobilized on Agarose Resin Columns This example shows the protease activity of resin-immobilized elastase, cathepsin G, and trypsin, using Tau and α-synuclein as the reaction substrate. The forms of Tau protein tested included a 2N4R isoform with P301L substitution ("Tau-441 (P301L)"), a 2N3R isoform ("Tau-410"), and a 2N4R isoform phosphorylated by GSK3β ("p-Tau-441").

To assess the protease activity against Tau-441 (P301L), 100 μl of 50 μg/ml Tau (P301L) solution was added to blank columns or columns having immobilized elastase, cathepsin G, or trypsin (prepared as described in Example 2). Columns were incubated at room temperature on a rotating support or at 37° C. in a temperature-controlled mixer. At 2, 10 and 20 minute incubation times, columns were centrifuged for 10 seconds and 20 μl of sample transferred for SDS-PAGE analysis. 16 μl/0.8 μg of protein were loaded onto 10% polyacrylamide gels and following electrophoresis, protein bands were visualized by silver staining.

To assess the protease activity against Tau-410, p-Tau-441, and α-synuclein, 0.5 mL of 10 μM substrate solution was added to blank columns or columns having immobilized elastase or trypsin (prepared as described in Example 2). After end-to-end rotation of the column for the indicated incubation time at room temperature, 10 μl of sample solution was collected and the reaction stopped by inactivation of the protease. The samples were analyzed by electrophoresis on a 10% sodium dodecyl sulfate (SDS) polyacrylamide gel and protein bands were visualized by silver staining. The band intensity was quantified using ChemiDoc quantification tool. For Tau-410 and α-synuclein, the intensity of the main dominant band was quantified. For p-Tau-441, the two dominant bands (top bands), which correspond to distinct phosphorylated Tau patterns, were quantified together. The results are normalized against the amounts of substrate proteins incubated for the same duration in blank columns and are shown in Table 2 and depicted in FIGS. 3D, 3E, and 3F.

TABLE 2

Quantification of Tau and α-synuclein protein digestion by immobilized elastase and trypsin

| Time (min) | Trypsin column (% digestion) | | | Elastase column (% digestion) | | |
|---|---|---|---|---|---|---|
| | Tau-410 | p-Tau-441 | α-synuclein | Tau-410 | p-Tau-441 | α-synuclein |
| 0 | 0 | 0 | 0 | 0 | 0 | 0 |
| 1 | 59 | 70 | 90 | 28 | 33 | 71 |
| 5 | 65 | 100 | 100 | 50 | 93 | N/A |
| 60 | 93 | 100 | 100 | 81 | 100 | N/A |

The protease activity of kallikrein-5 (KLK5) and kallikrein-6 (KLK6) was assessed by a similar method. The substrate solutions tested included 10 μM Tau-441 (P301L) in PBS, 10 μM p-Tau-441 in PBS, 10 μM α-synuclein in PBS, and 9 μM TDP-43 in 50 mM HEPES pH 8.0, 500 mM NaCl, 5 mM DTT, 20% (v/v) glycerol, and 0.4 M urea. The substrate solutions were added to blank columns or columns having immobilized KLK5 or KLK6 (prepared as described in Example 2). The substrate proteins were analyzed by electrophoresis on a 10% SDS polyacrylamide gel and protein bands were visualized by silver staining. The band intensity was quantified using ChemiDoc quantification tool. For Tau-410, Tau-441 (P301L), TDP, and α-synuclein, the intensity of the main dominant band was quantified. For p-Tau-441, the two dominant bands (top bands B1 and B2), which correspond to distinct phosphorylated Tau patterns, were quantified separately. The percentage of substrate proteins digested by the proteases, relative to the amounts of substrate proteins incubated for the same duration in blank columns, are shown in Tables 3 and 4.

TABLE 3

Quantification of Tau and TDP-43 protein digestion by immobilized kallikrein-5

| Time (min) | Tau-441 (P301L) | p-Tau-441 (B1) | p-Tau-441 (B2) | TDP-43 |
|---|---|---|---|---|
| 0 | 0 | 0 | 0 | 0 |
| 1 | 0 | 15 | 52 | 0 |
| 5 | 9 | 37 | 64 | 0 |
| 60 | 54 | 77 | 80 | 20 |

TABLE 4

Quantification of Tau and TDP-43 protein digestion by immobilized kallikrein-6

| Time (min) | Tau-410 | Tau-441 (P301L) | p-Tau-441 (B1) | p-Tau-441 (B2) | TDP-43 | α-synuclein |
|---|---|---|---|---|---|---|
| 0 | 0 | 0 | 0 | 0 | 0 | 0 |
| 1 | 31 | 68 | 74 | 63 | 1 | 77 |

TABLE 4-continued

Quantification of Tau and TDP-43 protein digestion by immobilized kallikrein-6

| Time (min) | Tau-410 | Tau-441 (P301L) | p-Tau-441 (B1) | p-Tau-441 (B2) | TDP-43 | α-synuclein |
|---|---|---|---|---|---|---|
| 5 | 56 | 91 | 98 | 95 | 18 | 80 |
| 60 | 74 | 79 | 97 | 92 | 29 | 72 |

Figure 3A:
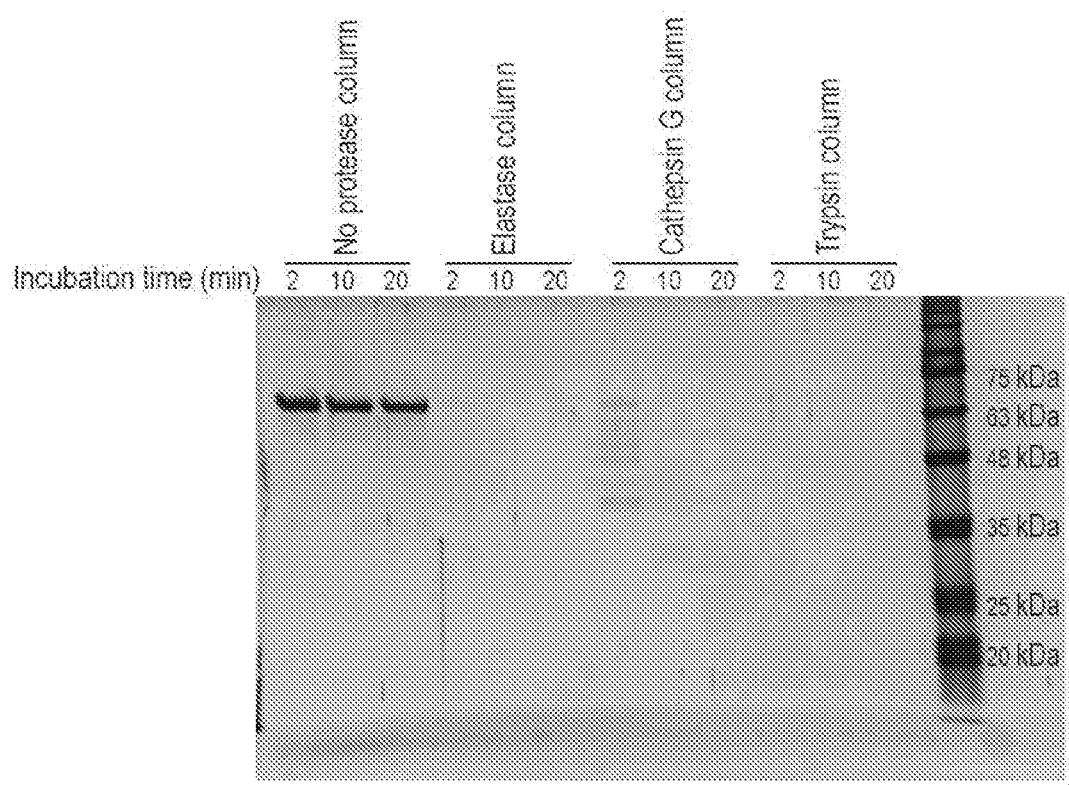
FIG. 3A is a silver-stained SDS-PAGE gel showing the digestion of Tau-441 (P301L) by elastase, cathepsin G, and trypsin immobilized on agarose resin columns.
Figure 3B:
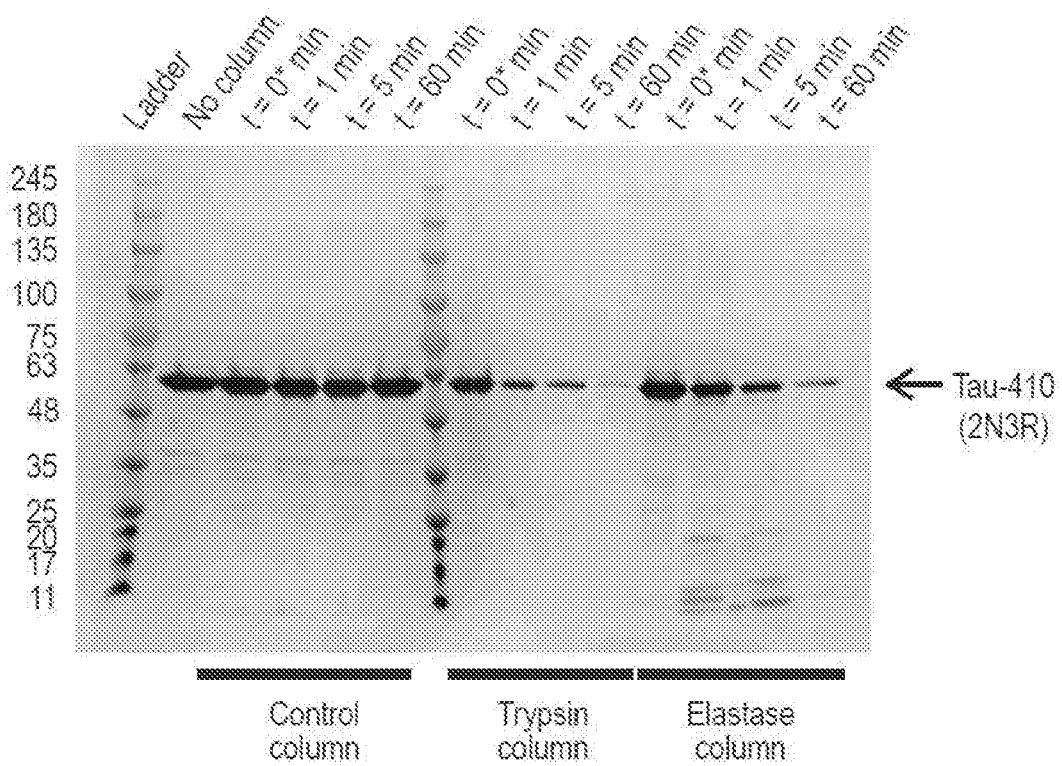
FIGS. 3B, 3C, and 3D are photographs of silver stained SDS-PAGE gels showing digestion of Tau-410, p-Tau-441, and α-synuclein, respectively, by elastase and trypsin immobilized on agarose resin columns. "No column" means the substrate protein sample was not added in any column. "T=0 min*" means the substrate protein sample was applied to the column and instantly collected by spinning the column. The last two lanes of the gel shown in FIG. 3D was broken on the bottom, so the digestion data of α-synuclein by elastase at time points 5 minutes and 60 minutes are missing.
Figure 3C:
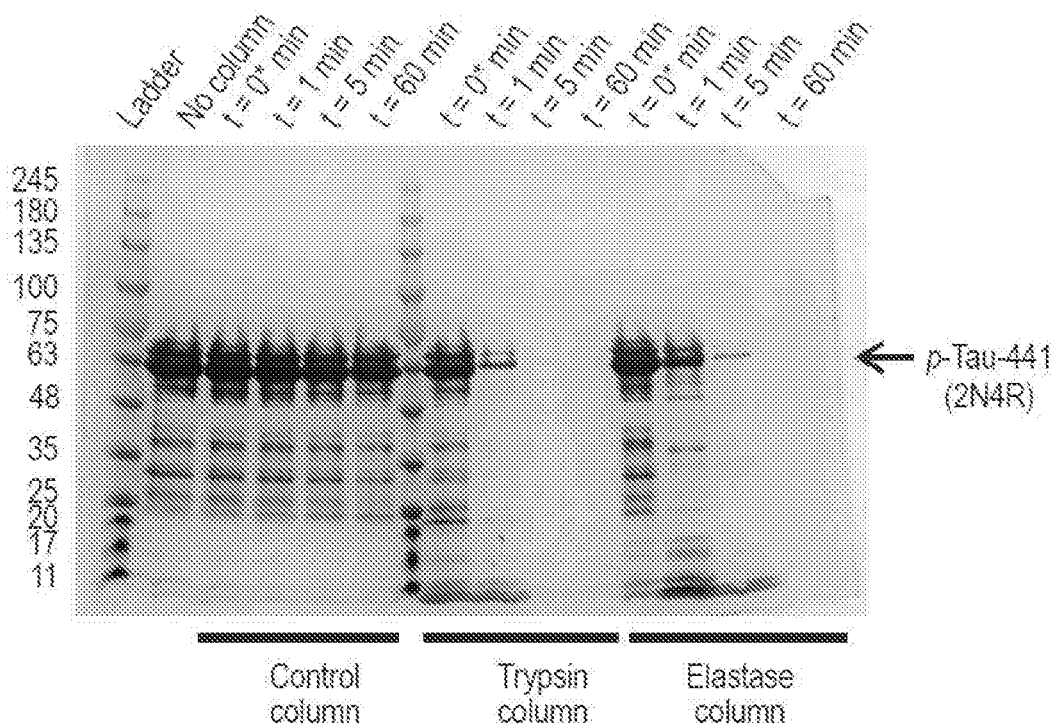
Figure 3D:
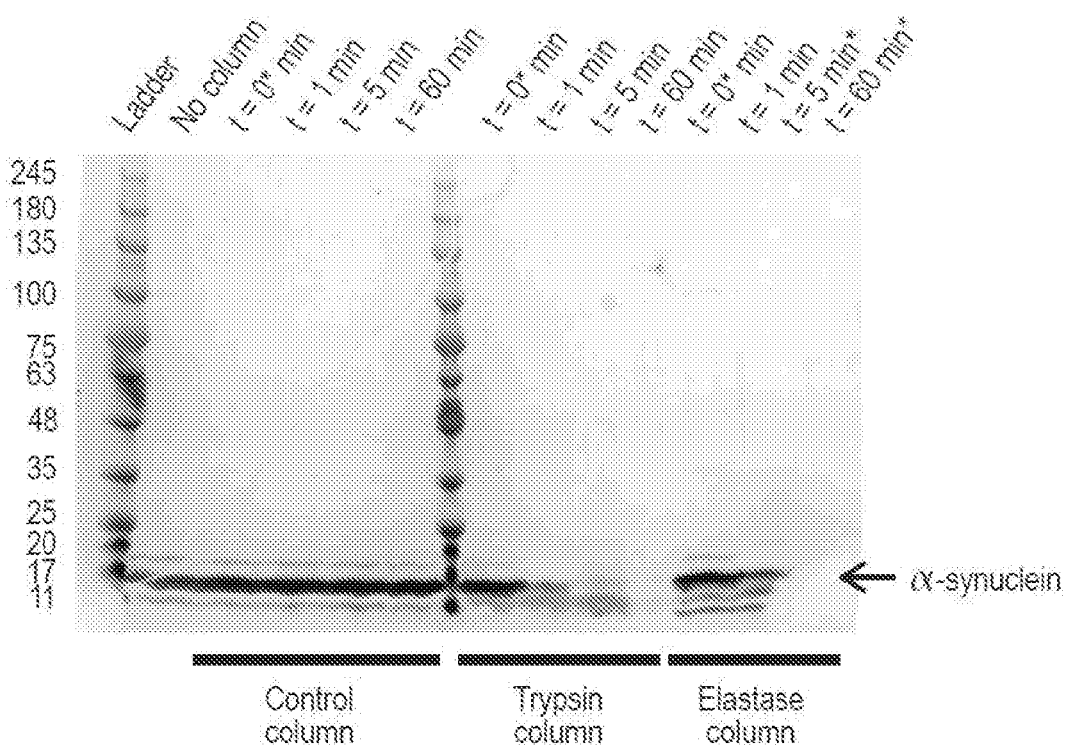
Figure 3E:
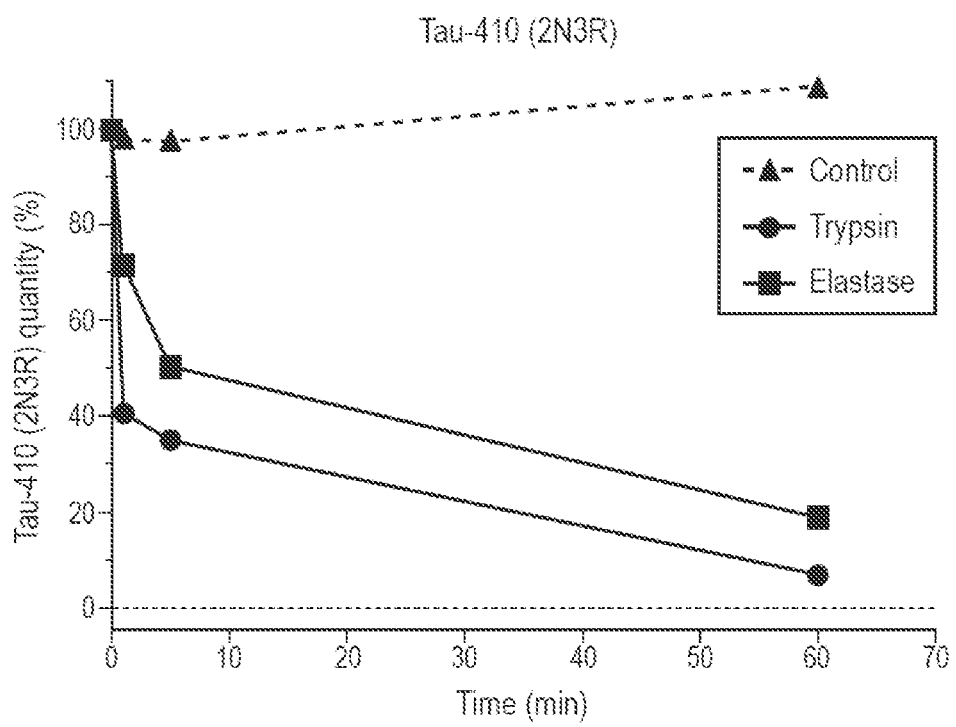
FIGS. 3E, 3F, and 3G are line graphs showing quantification of band intensity of the SDS-PAGE gels shown in FIGS. 3B, 3C, and 3D, respectively. RFU represents relative fluroscense unit.
Figure 3F:
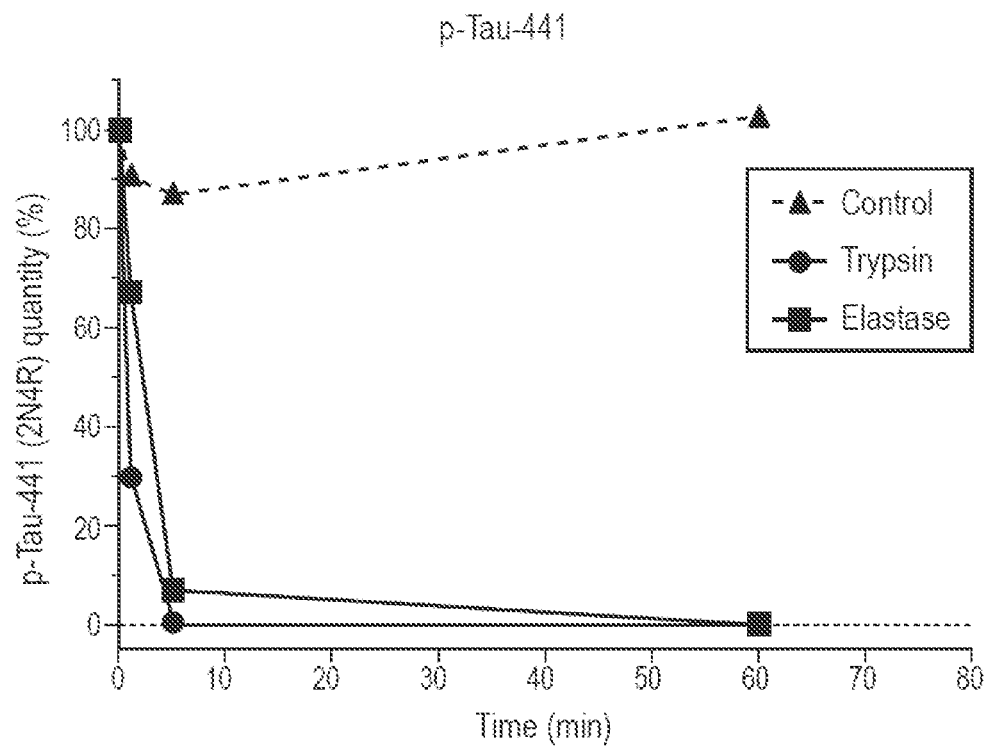
Figure 3G:
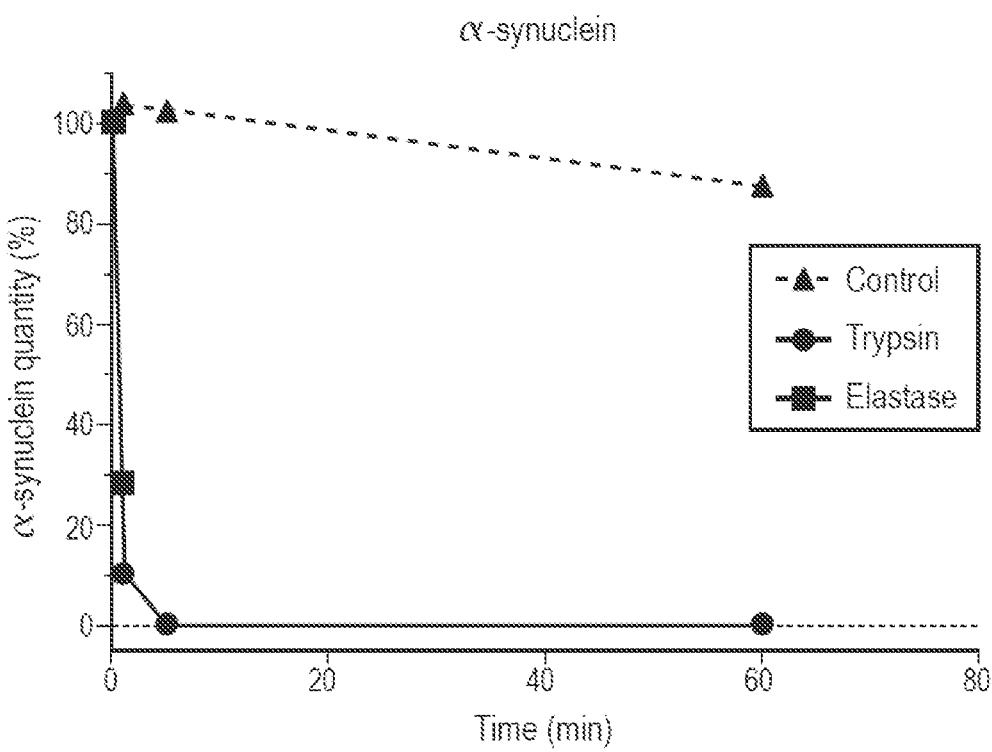

As shown in FIG. 3A, Tau-441 (P301L) was rapidly degraded by elastase, cathepsin G, and trypsin at room temperature. As shown in FIGS. 3B, 3C, 3E, and 3F and Table 2, Tau-410 and p-Tau-441 were rapidly degraded by elastase and trypsin. Similarly, as shown in FIGS. 3D and 3G and Table 2, α-synuclein was rapidly degraded by elastase and trypsin. Furthermore, as shown in Table 3, Tau-441 (P301L), p-Tau-441, and TDP-43 were degraded by KLK5. As shown in Table 4, Tau-410, Tau-441 (P301L), p-Tau-441, TDP-43, and α-synuclein were degraded by KLK6.

Example 4—Reduced Toxicity of Tau by Treatment with Proteases

This example describes a method for determining the toxicity of protease-treated Tau on in vitro neuronal cells Samples of Tau (P301L) treated with agarose resin alone or resin coupled with elastase, cathepsin G, or trypsin (prepared as described in Example 3) can be added to iCell® motor neurons (FUJIFILM Cellular Dynamics, Inc., Madison, Wis.). Following pre-determined incubation times, motor neuron viability can be assessed by any standard cell viability assay (e.g., flow cytometric analysis of propidium iodide-stained cells).

NUMBERED EMBODIMENTS

Embodiments disclosed herein include embodiments P1 to P107 and Q1 to Q108, as provided in the numbered embodiments of the disclosure:

Embodiment P1: A method for treating a subject suffering from a neurological disorder characterized by the presence of toxic proteins comprising contacting the cerebrospinal fluid (CSF) of the subject with an agent capable of removing or degrading the toxic protein.

Embodiment P2: The method of embodiment P1, wherein the neurological disorder is characterized by the presence of tau proteins (e.g., tau protein aggregates, tau protein tangles, tau oligomers, hyperphosphorylated tau proteins, soluble tau proteins, tau dimers).

Embodiment P3: The method of embodiment P2, wherein the neurological disorder is a tauopathy selected from Progressive supranuclear palsy (PSP), Alzheimer's disease (AD), Parkinson's disease (PD), Primary age-related tauopathy (PART), chronic traumatic encephalopathy (CTE), corticobasal degeneration (CBD) or corticobasal ganglionic degeneration (CBGD), frontotemporal dementia with parkinsonism linked to chromosome 17 (FTDP-17), Lytico-bodig disease, ganglioglioma, meningioangiomatosis, post-encephalitic Parkinsonism and subacute-sclerosing panenecephalitis (SSPE).

Embodiment P4: The method of embodiment P2, wherein the neurological disorder is progressive supranuclear palsy (PSP).

Embodiment P5: The method of embodiment P2, wherein the neurological disorder is frontotemporal lobar degeneration (FTLD) (e.g., frontotemporal dementia (FTD)).

Embodiment P6: The method of embodiment P2, wherein the neurological disorder is Alzheimer's disease.

Embodiment P7: The method of any one of embodiments P1 to P6, wherein the agent is an enzyme.

Embodiment P8: The method of embodiment P7, wherein the enzyme is a protease.

Embodiment P9: The method of embodiment P8, wherein the protease is able to reduce the concentration of toxic protein (e.g., a toxic tau protein (e.g., tau protein aggregates, tau protein tangles, tau oligomers, hyperphosphorylated tau proteins, soluble tau proteins, tau dimers) in the CSF by 20% or more (e.g., by 30% or more, by 40% or more, by 50% or more, by 60% or more, by 70% or more, by 80% or more, by 90% or more, by 95% or more, by 99% or more) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment P10: The method of embodiment P8 or P9, wherein the protease can reduce the concentration of toxic proteins (e.g., a toxic tau protein (e.g., tau protein aggregates, tau protein tangles, tau oligomers, hyperphosphorylated tau proteins, soluble tau proteins, tau dimers) below 1000 ng/mL (e.g., below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment P11: The method of any one of embodiments P8 to P10, wherein the protease is characterized by an active site capable of selectively recognizing the peptide sequence of the toxic protein (e.g., a toxic tau protein (e.g., tau protein aggregates, tau protein tangles, tau oligomers, hyperphosphorylated tau proteins, soluble tau proteins, tau dimers) over other proteins normally occurring in the CSF and is further capable of specific cleavage of at least one peptide bond of the toxic protein over cleavage of peptide bonds of proteins normally occurring in the CSF.

Embodiment P12: The method of any one of embodiments P8 to P11, wherein the protease is capable of effecting the degradation of the toxic proteins (e.g., a toxic tau protein (e.g., tau protein aggregates, tau protein tangles, tau oligomers, hyperphosphorylated tau proteins, soluble tau proteins, tau dimers) without significant effects on the concentration of proteins naturally occurring in the CSF.

Embodiment P13: The method of any one of embodiments P8 to P12, wherein the protease has higher specificity and lower affinity for the toxic proteins (e.g., a toxic tau protein (e.g., tau protein aggregates, tau protein tangles, tau oligomers, hyperphosphorylated tau proteins, soluble tau proteins, tau dimers) compared to proteins normally occurring in the CSF.

Embodiment P14: The method of any one of embodiments P8 to P12, wherein the protease has higher specificity and higher affinity for the toxic proteins (e.g., a toxic tau protein (e.g., tau protein aggregates, tau protein tangles, tau oligomers, hyperphosphorylated tau proteins, soluble tau proteins, tau dimers) compared to proteins normally occurring in the CSF.

Embodiment P15: The method of any one of embodiments P8 to P14, wherein the protease has higher efficiency cleaving at least one peptide bond of the toxic proteins (e.g., a toxic tau protein (e.g., tau protein aggregates, tau protein tangles, tau oligomers, hyperphosphorylated tau proteins, soluble tau proteins, tau dimers) compared to the peptide bonds of proteins normally occurring in the CSF.

Embodiment P16: The method of any one of embodiments P8 to P15, wherein the protease is selected from the group consisting of calpains (e.g., calpain-2), caspases (e.g., caspase-1, caspase-3, caspase-6, caspase-7, caspase-8), granzymes (e.g., granzyme A), trypsin, and meprin alpha.

Embodiment P17: The method of any one of embodiments P8 to P16, wherein the protease is a protease naturally occurring in CSF.

Embodiment P18: The method of any one of embodiments P1 to P17, comprising a step of removing the CSF from the subject prior to contacting it with the agent and a step of reintroducing the CSF back into the subject after contacting it with the agent; or the method comprising contacting the CSF of the subject to an agent immobilized to a solid surface or support in a device implanted into the body of the subject, optionally wherein the agent or the agent immobilized to the solid surface or support is extracted and reintroduced to the implanted device during treating the subject for over an extended period of time, optionally wherein the extended period is an intermittent period of 2-12 months.

Embodiment P19: The method of any one of embodiments P1 to P18, wherein the agent is immobilized (e.g., the agent is a protease immobilized on a solid substrate).

Embodiment P20: The method of embodiment P19, wherein the agent is immobilized by cross-linking to porous beads or membranes (e.g., the agent is a protease cross-linked to porous beads or membranes).

Embodiment P21: The method of embodiment P20, wherein the agent (e.g., the protease) is immobilized on a solid support.

Embodiment P22: The method of embodiment P21, wherein the solid support is a porous solid support.

Embodiment P23: The method of embodiment P21 or P22, wherein the agent (e.g., the protease) is attached to the support by covalent binding.

Embodiment P24: The method of any one of embodiments P21 to P23, wherein the support is a cross-linked resin.

Embodiment P25: The method of embodiment P24, wherein the cross-linked resin is an agarose resin.

Embodiment P26: The method of embodiment P20, wherein the agent is immobilized by precipitation (e.g., as an amorphous or crystalline precipitate).

Embodiment P27: The method of embodiment P26, wherein the precipitated agent is cross-linked (e.g., to form a cross-linked amorphous or crystalline precipitate, e.g., cross-linked protease crystals, e.g., cross-linked amorphous protease precipitate).

Embodiment P28: The method of embodiment P27, wherein the agent is lyophilized to form a dry powder and the powder is placed inside a porous coating to form beads.

Embodiment P29: The method of any one of embodiments P18 to P28, further comprising a step of filtering the CSF prior to reintroducing the CSF back into the subject.

Embodiment P30: The method of any one of embodiments P1 to P17, wherein the agent is directly introduced into the CSF of the subject.

Embodiment P31: The method of any one of embodiments P8 to P10 and P15 to P30, wherein the protease is not selective for the degradation of toxic proteins (e.g., a toxic tau protein (e.g., tau protein aggregates, tau protein tangles, tau oligomers, hyperphosphorylated tau proteins, soluble tau proteins, tau dimers) over other proteins normally occurring in the CSF.

Embodiment P32: A composition comprising: (a) cerebrospinal fluid (CSF) of a subject suffering from a neurological disorder characterized by the production of toxic proteins; and (b) an agent capable of degrading or removing the toxic proteins.

Embodiment P33: The composition of embodiment P32, wherein the neurological disorder is characterized by the presence of toxic tau proteins (e.g., tau protein aggregates, tau protein tangles, tau oligomers, hyperphosphorylated tau proteins, soluble tau proteins, tau dimers).

Embodiment P34: The composition of embodiment P33, wherein the neurological disorder is a tauopathy selected from Progressive supranuclear palsy (PSP), Alzheimer's disease (AD), Parkinson's disease (PD), Primary age-related tauopathy (PART), chronic traumatic encephalopathy (CTE), corticobasal degeneration (CBD) or corticobasal ganglionic degeneration (CBGD), frontotemporal dementia with parkinsonism linked to chromosome 17 (FTDP-17), Lytico-bodig disease, ganglioglioma, meningioangiomatosis, post-encephalitic Parkinsonism and subacute-sclerosing panenecephalitis (SSPE).

Embodiment P35: The composition of embodiment P33, wherein the neurological disorder is progressive supranuclear palsy (PSP).

Embodiment P36: The composition of embodiment P33, wherein the neurological disorder is frontotemporal lobar degeneration (FTLD) (e.g., frontotemporal dementia (FTD)).

Embodiment P37: The composition of embodiment P33, wherein the neurological disorder is Alzheimer's disease (AD).

Embodiment P38: The composition of any one of embodiments P30 to P37, wherein the agent is an enzyme.

Embodiment P39: The composition of embodiment P38, wherein the enzyme is a protease.

Embodiment P40: The composition of embodiment P39, wherein the protease is able to reduce the concentration of toxic protein (e.g., a toxic tau protein (e.g., tau protein aggregates, tau protein tangles, tau oligomers, hyperphosphorylated tau proteins, soluble tau proteins, tau dimers) in the CSF by 20% or more (e.g., by 30% or more, by 40% or more, by 50% or more, by 60% or more, by 70% or more, by 80% or more, by 90% or more, by 95% or more, by 99% or more) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment P41: The composition of embodiment P39 or P40, wherein the protease can reduce the concentration of toxic proteins (e.g., a toxic tau protein (e.g., tau protein aggregates, tau protein tangles, tau oligomers, hyperphosphorylated tau proteins, soluble tau proteins, tau dimers) below 1000 ng/mL (e.g., below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment P42: The composition of any one of embodiments P39 to P41, wherein the protease is characterized by an active site capable of selectively recognizing the peptide sequence of the toxic protein (e.g., a toxic tau protein (e.g., tau protein aggregates, tau protein tangles, tau oligomers, hyperphosphorylated tau proteins, soluble tau proteins, tau dimers) over other proteins normally occurring in the CSF and is further capable of specific cleavage of at least one peptide bond of the toxic protein over cleavage of peptide bonds of proteins normally occurring in the CSF.

Embodiment P43: The composition of any one of embodiments P39 to P42, wherein the protease is capable of effecting the degradation of the toxic proteins (e.g., a toxic tau protein (e.g., tau protein aggregates, tau protein tangles, tau oligomers, hyperphosphorylated tau proteins, soluble tau proteins, tau dimers) without significant effects on the concentration of proteins naturally occurring in the CSF.

Embodiment P44: The composition of any one of embodiments P39 to P43, wherein the protease has higher specificity and lower affinity for the toxic proteins (e.g., a toxic tau protein (e.g., tau protein aggregates, tau protein tangles, tau oligomers, hyperphosphorylated tau proteins, soluble tau proteins, tau dimers) compared to proteins normally occurring in the CSF.

Embodiment P45: The composition of any one of embodiments P39 to P43, wherein the protease has higher specificity and higher affinity for the toxic proteins (e.g., a toxic tau protein (e.g., tau protein aggregates, tau protein tangles, tau oligomers, hyperphosphorylated tau proteins, soluble tau proteins, tau dimers) compared to proteins normally occurring in the CSF.

Embodiment P46: The composition of any one of embodiments P39 to P45, wherein the protease has higher efficiency cleaving at least one peptide bond of the toxic proteins (e.g., a toxic tau protein (e.g., tau protein aggregates, tau protein tangles, tau oligomers, hyperphosphorylated tau proteins, soluble tau proteins, tau dimers) compared to the peptide bonds of proteins normally occurring in the CSF.

Embodiment P47: The composition of any one of embodiments P39 to P46, wherein the protease is selected from the group consisting of calpains (e.g., calpain-2), caspases (e.g., caspase-1, caspase-3, caspase-6, caspase-7, and caspase-8), granzymes (e.g., granzyme A), trypsin, and meprin alpha.

Embodiment P48: The composition of any one of embodiments P39 to P47, wherein the protease is a protease naturally occurring in CSF.

Embodiment P49: The composition of any one of embodiments P39 to P48, wherein the agent is immobilized (e.g., the agent is a protease immobilized on a solid substrate).

Embodiment P50: The composition of embodiment P49, wherein the agent (e.g., the protease) is immobilized on a solid support.

Embodiment P51: The method of embodiment P50, wherein the solid support is a porous solid support.

Embodiment P52: The composition of embodiment P50 or P51, wherein the agent (e.g., the protease) is attached to the solid support by covalent binding.

Embodiment P53: The composition of any one of embodiments P50 to P52, wherein the solid support is a cross-linked resin.

Embodiment P54: The composition of embodiment P53, wherein the cross-linked resin is an agarose resin.

Embodiment P55: The composition of embodiment P49, wherein the agent is immobilized by cross-linking to porous beads or membranes (e.g., the agent is a protease cross-linked to porous beads or membranes).

Embodiment P56: The composition of embodiment P49, wherein the agent is immobilized by precipitation (e.g., as an amorphous or crystalline precipitate).

Embodiment P57: The composition of embodiment P56, wherein the precipitated agent is cross-linked (e.g., to form a cross-linked amorphous or crystalline precipitate, e.g., cross-linked protease crystals, e.g., cross-linked amorphous protease precipitate).

Embodiment P58: The composition of embodiment P49, wherein the agent is lyophilized to form a dry powder and the powder is placed inside a porous coating to form beads.

Embodiment P59: The composition of any one of embodiments P39 to P41 and P46 to P58, wherein the protease is not selective for the degradation of toxic proteins (e.g., a toxic tau protein (e.g., tau protein aggregates, tau protein tangles, tau oligomers, hyperphosphorylated tau proteins, soluble tau proteins, tau dimers) over other proteins normally occurring in the CSF.

Embodiment P60: A method of diagnosing and treating a subject suffering from a neurological disorder characterized by the production of toxic proteins, the method comprising: (a) receiving information regarding the presence of toxic proteins in the cerebrospinal fluid of the subject and if the subject has been determined to have toxic proteins in the CSF, diagnosing the subject as susceptible to the treatment of step (b); and (b) treating the subject diagnosed as susceptible in step (a) by contacting the cerebrospinal fluid (CSF) of the subject with an agent (e.g., an enzyme, e.g., a protease) capable of removing or degrading the toxic proteins.

Embodiment P61: The method of embodiment P60, wherein the neurological disorder is a tauopathy selected from Progressive supranuclear palsy (PSP), Alzheimer's disease (AD), Parkinson's disease (PD), Primary age-related tauopathy (PART), chronic traumatic encephalopathy (CTE), corticobasal degeneration (CBD) or corticobasal ganglionic degeneration (CBGD), frontotemporal dementia with parkinsonism linked to chromosome 17 (FTDP-17), Lytico-bodig disease, ganglioglioma, meningioangiomatosis, post-encephalitic Parkinsonism and subacute-sclerosing panencephalitis (SSPE).

Embodiment P62: The method of embodiment P60, wherein the neurological disorder is progressive supranuclear palsy (PSP).

Embodiment P63: The method of embodiment P60, wherein the neurological disorder is frontotemporal lobar degeneration (FTLD) (e.g., frontotemporal dementia (FTD)).

Embodiment P64: The method of embodiment P60 wherein the neurological disorder is Alzheimer's disease.

Embodiment P65: The method of any one of embodiments P60 to P64, wherein the toxic proteins are a toxic tau proteins (e.g., tau protein aggregates, tau protein tangles, tau oligomers, hyperphosphorylated tau proteins, soluble tau proteins, tau dimers).

Embodiment P66: The method of any one of embodiments P60 to P65, wherein the agent is an enzyme.

Embodiment P67: The method of embodiment P66, wherein the enzyme is a protease.

Embodiment P68: The method of embodiment P67, wherein the protease is able to reduce the concentration of toxic protein (e.g., a toxic tau protein (e.g., tau protein aggregates, tau protein tangles, tau oligomers, hyperphosphorylated tau proteins, soluble tau proteins, tau dimers) in the CSF by 20% or more (e.g., by 30% or more, by 40% or more, by 50% or more, by 60% or more, by 70% or more, by 80% or more, by 90% or more, by 95% or more, by 99% or more) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment P69: The method of embodiment P67 or P68, wherein the protease can reduce the concentration of toxic proteins (e.g., a toxic tau protein (e.g., tau protein aggregates, tau protein tangles, tau oligomers, hyperphosphorylated tau proteins, soluble tau proteins, tau dimers) below 1000 ng/mL (e.g., below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment P70: The method any one of embodiments P67 to P69, wherein the protease is characterized by an active site capable of selectively recognizing the peptide sequence of the toxic protein (e.g., a toxic tau protein (e.g., tau protein aggregates, tau protein tangles, tau oligomers, hyperphosphorylated tau proteins, soluble tau proteins, tau dimers) over other proteins normally occurring in the CSF and is further capable of specific cleavage of at least one peptide bond of the toxic protein over cleavage of peptide bonds of proteins normally occurring in the CSF.

Embodiment P71: The method of any one of embodiments P67 to P70, wherein the protease is capable of effecting the degradation of the toxic proteins (e.g., a toxic tau protein (e.g., tau protein aggregates, tau protein tangles, tau oligomers, hyperphosphorylated tau proteins, soluble tau proteins, tau dimers) without significant effects on the concentration of proteins naturally occurring in the CSF.

Embodiment P72: The method of any one of embodiments P67 to P71, wherein the protease has higher specificity and lower affinity for the toxic proteins (e.g., a toxic tau protein (e.g., tau protein aggregates, tau protein tangles, tau oligomers, hyperphosphorylated tau proteins, soluble tau proteins, tau dimers) compared to proteins normally occurring in the CSF.

Embodiment P73: The method of any one of embodiments P67 to P71, wherein the protease has higher specificity and higher affinity for the toxic (e.g., a toxic tau protein (e.g., tau protein aggregates, tau protein tangles, tau oligomers, hyperphosphorylated tau proteins, soluble tau proteins, tau dimers) compared to proteins normally occurring in the CSF.

Embodiment P74: The method of any one of embodiments P67 to P73, wherein the protease has higher efficiency cleaving at least one peptide bond of the toxic proteins (e.g., a toxic tau protein (e.g., tau protein aggregates, tau protein tangles, tau oligomers, hyperphosphorylated tau proteins, soluble tau proteins, tau dimers) compared to the peptide bonds of proteins normally occurring in the CSF.

Embodiment P75: The method of any one of embodiments P67 to P74, wherein the protease is selected from the group consisting of calpains (e.g., calpain-2), caspases (e.g., caspase-1, caspase-3, caspase-6, caspase-7, caspase-8), granzymes (e.g., granzyme A), trypsin, and meprin alpha.

Embodiment P76: The method of any one of embodiments P67 to P75, wherein the protease is a protease naturally occurring in CSF.

Embodiment P77: The method of any one of embodiments P60 to P76 comprising a step of removing the CSF from the subject prior to contacting it with the agent and a step of reintroducing the CSF back into the subject after contacting it with the agent; or the method comprising contacting the CSF of the subject to the protease immobilized to a solid surface or support in a device implanted into the body of the subject, optionally wherein the protease or the protease immobilized to the solid surface or support is extracted and reintroduced to the implanted device during treating the subject for over an extended period of time, optionally wherein the extended period is an intermittent period of 2-12 months.

Embodiment P78: The method of embodiment P77, wherein the agent is immobilized (e.g., the agent is a protease immobilized on a solid substrate).

Embodiment P79: The method of embodiment P78, wherein the agent (e.g., the protease) is immobilized on a solid support.

Embodiment P80: The method of embodiment P79, wherein the solid support is a porous solid support.

Embodiment P81: The method of embodiment P79 or P80, wherein the agent (e.g., the protease) is attached to the solid support by covalent binding.

Embodiment P82: The method of any one of embodiments P78 to P81, wherein the solid support is a cross-linked resin.

Embodiment P83: The method of embodiment P82, wherein the cross-linked resin is an agarose resin.

Embodiment P84: The method of embodiment P78, wherein the agent is immobilized by cross-linking to porous beads or membranes (e.g., the agent is a protease cross-linked to porous beads or membranes).

Embodiment P85: The method of embodiment P78, wherein the agent is immobilized by precipitation (e.g., as an amorphous or crystalline precipitate).

Embodiment P86: The method of embodiment P85, wherein the precipitated agent is cross-linked (e.g., to form a cross-linked amorphous or crystalline precipitate, e.g., cross-linked protease crystals, e.g., cross-linked amorphous protease precipitate).

Embodiment P87: The method of embodiment P78, wherein the agent is lyophilized to form a dry powder and the powder is placed inside a porous coating to form beads.

Embodiment P88: The method of any one of embodiments P77 to P87, further comprising a step of filtering the CSF prior to reintroducing the CSF back into the subject.

Embodiment P89: The method of any one of embodiments P60 to P76, wherein the agent is directly introduced into the CSF of the subject.

Embodiment P90: The method of any one of embodiments P66 to P69 and P74 to P89, wherein the protease is not selective for the degradation of toxic proteins (e.g., a toxic tau protein (e.g., tau protein aggregates, tau protein tangles, tau oligomers, hyperphosphorylated tau proteins, soluble tau proteins, tau dimers) over other proteins normally occurring in the CSF.

Embodiment P91: The method of any one of embodiments P1 to P17, or P60 to P76 further comprising a step of sterilly removing the CSF from the subject prior to sterilly contacting the CSF with a device (100) comprising protease immobilized on an agarose column, and a step of sterilly reintroducing the CSF back into the subject after contacting the CSF with the device (100).

Embodiment P92: The method of embodiment P91, wherein the subject is a non-human animal.

Embodiment P93: The method of any one of embodiments P1 to P17, or P60 to P76, wherein the CSF contacts a device implanted in the subject, wherein the device comprises the agent immobilized on a substrate.

Embodiment P94: The method of embodiment P93, wherein the agent is introduced into or extracted from the device by injection.

Embodiment P95: The method of embodiment P93 or P94, wherein the subject is human.

Embodiment P96: The method of any one of embodiments P19 to P27, or P78 to P86, or the composition of any one of embodiments P49 to P57, wherein the agent is a protease and wherein the protease is immobilized at a concentration of about 1 mg/ml to about 10 mg/ml.

Embodiment P97: The method of embodiment P8 or P67, or the composition of embodiment P39, wherein the protease is a serine protease.

Embodiment P98: The method or composition of embodiment P94, wherein the serine protease is selected from the group consisting of trypsin, elastase and thrombin.

Embodiment P99: The method of embodiment P8 or P67, or the composition of embodiment P39, wherein the protease is an aspartic protease.

Embodiment P100: The method or composition of embodiment P99, wherein the aspartic protease is pepsin or endothiapepsin.

Embodiment P101: The method of embodiment P8 or P67, or the composition of embodiment P39, wherein the protease is not a metalloprotease.

Embodiment P102: The method of embodiment P8 or P67, or the composition of embodiment P39, wherein the protease is not a cysteine protease.

Embodiment P103: The method of embodiment P8 or P67, or the composition of embodiment P39, wherein the protease is not dependent on a non-covalently bound cofactor for its proteolytic activity.

Embodiment P104: The method of embodiment P8 or P67, or the composition of embodiment P39, wherein the protease is a microbial protease, and wherein the microbial protease is optionally endothiapepsin.

Embodiment P105: A kit comprising a suitably formulated agent capable of degrading or removing a toxic protein from the cerebrospinal fluid (CSF) of a subject.

Embodiment P106: A kit comprising a system for contacting cerebrospinal fluid (CSF) of a subject with an agent suitably formulated for degrading or removing a toxic protein from the CSF, wherein the kit optionally comprises the agent.

Embodiment P107: The kit of embodiment P105 or P106, wherein the kit further comprises instructions for treating the CSF with the agent.

Embodiment Q1: A method for treating a subject suffering from a neurological disorder characterized by the presence of toxic proteins comprising contacting the cerebrospinal fluid (CSF) of the subject with an agent capable of removing or degrading the toxic protein.

Embodiment Q2: The method of embodiment Q1 wherein the neurological disorder is characterized by a mutation on a gene selected from the group of TAR-DNA-binding protein 43 kDa (TDP-43), superoxide dismutase (SOD1) or fused in sarcoma (FUS) mutation (i.e., a TDP-43, SOD1, FUS positive neurological disease).

Embodiment Q3: The method of embodiment Q2 wherein the neurological disorder is selected from the group consisting of TDP-43 positive amyotrophic lateral sclerosis (ALS), SOD1 positive ALS, FUS positive ALS, TDP-43 positive frontotemporal dementia (FTD), SOD1 positive FTD, FUS positive FTD, TDP-43 positive frontotemporal lobar degeneration (FTLD), SOD1 positive FTLD) and FUS positive FTLD.

Embodiment Q4: The method of any one of embodiments Q1 to Q3 wherein the toxic protein is selected from the group consisting of toxic TDP-43, toxic SOD1 and toxic FUS/TLS.

Embodiment Q5: The method of embodiment Q1 wherein the neurological disorder is selected from the group consisting of Parkinson's disease (PD), Alzheimer's Disease (AD), Huntington's disease (HD), Creutzfeldt-Jakob disease (CJD), variant Creutzfeldt-Jakob disease (vCJD) and Amyotrophic Lateral Sclerosis (ALS).

Embodiment Q6: The method of embodiment Q1 wherein the neurological disorder is characterized by the presence of α-synuclein (e.g., Parkinson's Disease), β-amyloid (e.g., Alzheimer's Disease), Huntingtin protein (HTT) (e.g., Huntington's Disease), Glutamate (e.g., Amyotrophic Lateral Sclerosis), prion proteins (e.g., Creutzfeldt-Jakob Disease (CJD), variant Creutzfeldt-Jakob Disease (vCJD)), e.g., inflammatory proteins such as cytokines, interleukines, tumor necrosis factors, other potentially harmful proteins and bacteria, viruses and other pathogens.

Embodiment Q7: The method of embodiment Q1 wherein the neurological disorder is characterized by the presence of tau proteins (e.g., tau protein aggregates, tau protein tangles, tau oligomers, hyperphosphorylated tau proteins, soluble tau proteins, tau dimers).

Embodiment Q8: The method of embodiment Q7 wherein the neurological disorder is a tauopathy selected from Progressive supranuclear palsy (PSP), Alzheimer's disease (AD), Parkinson's disease (PD), Primary age-related tauopathy (PART), chronic traumatic encephalopathy (CTE), corticobasal degeneration (CBD) or corticobasal ganglionic degeneration (CBGD), frontotemporal dementia with parkinsonism linked to chromosome 17 (FTDP-17), Lytico-bodig disease, ganglioglioma, meningioangiomatosis, post-encephalitic Parkinsonism and subacute-sclerosing panenecephalitis (SSPE).

Embodiment Q9: The method of embodiment Q7 wherein the neurological disorder is progressive supranuclear palsy (PSP).

Embodiment Q10: The method of embodiment Q7 wherein the neurological disorder is frontotemporal lobar degeneration (FTLD) (e.g., frontotemporal dementia (FTD)).

Embodiment Q11: The method of embodiment Q7 wherein the neurological disorder is Alzheimer's disease.

Embodiment Q12: The method of any one of embodiments Q1 to Q11 wherein the agent is an enzyme.

Embodiment Q13: The method of embodiment Q12 wherein the enzyme is a protease.

Embodiment Q14: The method of embodiment Q13 wherein the protease is able to reduce the concentration of toxic protein (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) in the CSF by 20% or more (e.g., by 30% or more, by 40% or more, by 50% or more, by 60% or more, by 70% or more, by 80% or more, by 90% or more, by 95% or more, by 99% or more) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment Q15: The method of embodiment Q13 or Q14 wherein the protease can reduce the concentration of toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) below 1000 ng/mL (e.g., below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment Q16: The method of any one of embodiments Q13 to Q15 wherein the protease is characterized by an active site capable of selectively recognizing the peptide sequence of the toxic protein (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) over other proteins normally occurring in the CSF and is further capable of specific cleavage of at least one peptide bond of the toxic protein over cleavage of peptide bonds of proteins normally occurring in the CSF.

Embodiment Q17: The method of any one of embodiments Q13 to Q16 wherein the protease is capable of effecting the degradation of the toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) without significant effects on the concentration of proteins naturally occurring in the CSF.

Embodiment Q18: The method of any one of embodiments Q13 to Q17 wherein the protease has higher specificity and lower affinity for the toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) compared to proteins normally occurring in the CSF.

Embodiment Q19: The method of any one of embodiments Q13 to Q17 wherein the protease has higher specificity and higher affinity for the toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) compared to proteins normally occurring in the CSF.

Embodiment Q20: The method of any one of embodiments Q13 to Q19 wherein the protease has higher efficiency cleaving at least one peptide bond of the toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) compared to the peptide bonds of proteins normally occurring in the CSF.

Embodiment Q21: The method of any one of embodiments Q13 to Q20 wherein the protease is selected from the group consisting of calpains (e.g., calpain-2), caspases (e.g., caspase-1, caspase-3, caspase-6, caspase-7, caspase-8), granzymes (e.g., granzyme A), trypsin, and meprin alpha.

Embodiment Q22: The method of any one of embodiments Q13 to Q20 wherein the protease is a protease naturally occurring in CSF.

Embodiment Q23: The method of any one of embodiments Q1 to Q22 further comprising a step of removing the CSF from the subject prior to contacting it with the agent and a step of reintroducing the CSF back into the subject after contacting it with the agent.

Embodiment Q24: The method of any one of embodiments Q1 to Q23 wherein the agent is immobilized (e.g., the agent is a protease immobilized on a solid substrate).

Embodiment Q25: The method of embodiment Q24 wherein the agent (e.g., the protease) is immobilized on a solid support.

Embodiment Q26: The method of embodiment Q25 wherein the solid support is a porous solid support.

Embodiment Q27: The method of embodiment Q25 or Q26 wherein the agent (e.g., the protease) is attached to the support by covalent binding.

Embodiment Q28: The method of any one of embodiments Q25 to Q27 wherein the support is a cross-linked resin.

Embodiment Q29: The method of embodiment Q28 wherein the cross-linked resin is an agarose resin.

Embodiment Q30: The method of embodiment Q24 wherein the agent is immobilized by cross-linking to porous beads or membranes (e.g., the agent is a protease cross-linked to porous beads or membranes).

Embodiment Q31: The method of any one of embodiments Q24 to Q26 wherein the agent is immobilized by precipitation (e.g., as an amorphous or crystalline precipitate).

Embodiment Q32: The method of embodiment Q31 wherein the precipitated agent is cross-linked (e.g., to form a cross-linked amorphous or crystalline precipitate, e.g., cross-linked protease crystals, e.g., cross-linked amorphous protease precipitate).

Embodiment Q33: The method of embodiment Q32 wherein the agent is lyophilized to form a dry powder and the powder is placed inside a porous coating to form beads.

Embodiment Q34: The method of any one of embodiments Q23 to Q33 further comprising a step of filtering the CSF prior to reintroducing the CSF back into the subject.

Embodiment Q35: The method of any one of embodiments Q1 to Q22 wherein the agent is directly introduced into the CSF of the subject.

Embodiment Q36: The method of any one of embodiments Q13 to Q15 and Q21 to Q35 wherein the protease is not selective for the degradation of toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) over other proteins normally occurring in the CSF.

Embodiment Q37: A composition comprising: (a) cerebrospinal fluid (CSF) of a subject suffering from a neurological disorder characterized by the production of toxic proteins; and (b) an agent capable of degrading or removing the toxic proteins.

Embodiment Q38: The composition of embodiment Q37 wherein the neurological disorder is characterized by a mutation on a gene selected from the group of TAR-DNA-binding protein 43 kDa (TDP-43), superoxide dismutase (SOD1) or fused in sarcoma (FUS) mutation (i.e., a TDP-43, SOD1, FUS positive neurological disease).

Embodiment Q39: The composition of embodiment Q38 wherein the neurological disorder is selected from the group consisting of TDP-43 positive amyotrophic lateral sclerosis (ALS), SOD1 positive ALS, FUS positive ALS, TDP-43 positive frontotemporal dementia (FTD), SOD1 positive FTD, FUS positive FTD, TDP-43 positive frontotemporal lobar degeneration (FTLD), SOD1 positive FTLD) and FUS positive FTLD.

Embodiment Q40. The composition of embodiments Q37 to Q39 wherein the toxic protein is selected from the group consisting of toxic TDP-43, toxic SOD1 and toxic FUS/TLS.

Embodiment Q41: The method of embodiment Q37 wherein the neurological disorder is selected from the group consisting of Parkinson's disease (PD), Alzheimer's Disease (AD), Huntington's disease (HD), Creutzfeldt-Jakob disease (CJD), variant Creutzfeldt-Jakob disease (vCJD) and Amyotrophic Lateral Sclerosis (ALS).

Embodiment Q42: The method of embodiment Q37 wherein the neurological disorder is characterized by the presence of α-synuclein (e.g., Parkinson's Disease), β-amyloid (e.g., Alzheimer's Disease), Huntingtin protein (HTT) (e.g., Huntington's Disease), Glutamate (e.g., Amyotrophic Lateral Sclerosis), prion proteins (e.g., Creutzfeldt-Jacob Disease (CJD), variant Creutzfeldt-Jacob Disease (vCJD)), e.g., inflammatory proteins such as cytokines, interleukines, tumor necrosis factors, other potentially harmful proteins and bacteria, viruses and other pathogens.

Embodiment Q43: The composition of embodiment Q37 wherein the neurological disorder is characterized by the presence of toxic tau proteins (e.g., tau protein aggregates, tau protein tangles, tau oligomers, hyperphosphorylated tau proteins, soluble tau proteins, tau dimers).

Embodiment Q44: The composition of embodiment Q43 wherein the neurological disorder is a tauopathy selected from Progressive supranuclear palsy (PSP), Alzheimer's disease (AD), Parkinson's disease (PD), Primary age-related tauopathy (PART), chronic traumatic encephalopathy (CTE), corticobasal degeneration (CBD) or corticobasal ganglionic degeneration (CBGD), frontotemporal dementia with parkinsonism linked to chromosome 17 (FTDP-17), Lytico-bodig disease, ganglioglioma, meningioangiomatosis, post-encephalitic Parkinsonism and subacute-sclerosing panenecephalitis (SSPE).

Embodiment Q45: The composition of embodiment Q43 wherein the neurological disorder is progressive supranuclear palsy (PSP).

Embodiment Q46: The composition of embodiment Q43 wherein the neurological disorder is frontotemporal lobar degeneration (FTLD)(e.g., frontotemporal dementia (FTD)).

Embodiment Q47: The composition of embodiment Q43 wherein the neurological disorder is Alzheimer's disease (AD).

Embodiment Q48: The composition of any one of embodiments Q37 to Q47 wherein the agent is an enzyme.

Embodiment Q49: The composition of embodiment Q48 wherein the enzyme is a protease.

Embodiment Q50: The composition of embodiment Q49 wherein the protease is able to reduce the concentration of toxic protein (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) in the CSF by 20% or more (e.g., by 30% or more, by 40% or more, by 50% or more, by 60% or more, by 70% or more, by 80% or more, by 90% or more, by 95% or more, by 99% or more) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment Q51: The composition of embodiment Q49 or Q50 wherein the protease can reduce the concentration of toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) below 1000 ng/mL (e.g., below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment Q52: The composition of any one of embodiments Q49 to Q51 wherein the protease is characterized by an active site capable of selectively recognizing the peptide sequence of the toxic protein (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) over other proteins normally occurring in the CSF and is further capable of specific cleavage of at least one peptide bond of the toxic protein over cleavage of peptide bonds of proteins normally occurring in the CSF.

Embodiment Q53: The composition of any one of embodiments Q49 to Q52 wherein the protease is capable of effecting the degradation of the toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) without significant effects on the concentration of proteins naturally occurring in the CSF.

Embodiment Q54: The composition of any one of embodiments Q49 to Q53 wherein the protease has higher specificity and lower affinity for the toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) compared to proteins normally occurring in the CSF.

Embodiment Q55: The composition of any one of embodiments Q49 to Q53 wherein the protease has higher specificity and higher affinity for the toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) compared to proteins normally occurring in the CSF.

Embodiment Q56: The composition of any one of embodiments Q49 to Q55 wherein the protease has higher efficiency cleaving at least one peptide bond of the toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) compared to the peptide bonds of proteins normally occurring in the CSF.

Embodiment Q57: The composition of any one of embodiments Q49 to Q56 wherein the protease is selected from the group consisting of calpains (e.g., calpain-2), caspases (e.g., caspase-1, caspase-3, caspase-6, caspase-7, and caspase-8), granzymes (e.g., granzyme A), trypsin, and meprin alpha.

Embodiment Q58: The composition of any one of embodiments Q49 to Q57 wherein the protease is a protease naturally occurring in CSF.

Embodiment Q59: The composition of any one of embodiments Q37 to Q58, wherein the agent is immobilized (e.g., the agent is a protease immobilized on a solid substrate).

Embodiment Q60: The composition of embodiment Q59 wherein the agent (e.g., the protease) is immobilized on a solid support.

Embodiment Q61: The composition of embodiment Q60 wherein the solid support is a porous solid support.

Embodiment Q62: The composition of embodiment Q60 or Q61 wherein the agent (e.g., the protease) is attached to the solid support by covalent binding.

Embodiment Q63: The composition of any one of embodiments Q60 to Q62 wherein the solid support is a cross-linked resin.

Embodiment Q64: The composition of embodiment Q63 wherein the cross-linked resin is an agarose resin.

Embodiment Q65: The composition of any one of embodiments Q59 to Q61 wherein the agent is immobilized by cross-linking to porous beads or membranes (e.g., the agent is a protease cross-linked to porous beads or membranes).

Embodiment Q66: The composition of embodiment Q59 wherein the agent is immobilized by precipitation (e.g., as an amorphous or crystalline precipitate).

Embodiment Q67: The composition of embodiment Q66 wherein the precipitated agent is cross-linked (e.g., to form a cross-linked amorphous or crystalline precipitate, e.g., cross-linked protease crystals, e.g., cross-linked amorphous protease precipitate).

Embodiment Q68: The composition of embodiment Q59 wherein the agent is lyophilized to form a dry powder and the powder is placed inside a porous coating to form beads.

Embodiment Q69: The method of any one of embodiments Q49 to Q51 or Q57 to Q68 wherein the protease is not selective for the degradation of toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) over other proteins normally occurring in the CSF.

Embodiment Q70: A method of diagnosing and treating a subject suffering from a neurological disorder characterized by the production of toxic proteins, the method comprising: (a) receiving information regarding the presence of toxic proteins in the cerebrospinal fluid of the subject or receiving information regarding TDP-43, SOD1 or FUS status of a subject and if the subject has been determined to have toxic proteins in the CSF, or if the subject has been determined to be TDP-43, SOD1 or FUS positive diagnosing the subject as susceptible to the treatment of step (b); and (b) treating the subject diagnosed as susceptible in step a) by contacting the cerebrospinal fluid (CSF) of the subject with an agent (e.g., an enzyme, e.g., a protease) capable of removing or degrading the toxic proteins.

Embodiment Q71: The method of embodiment Q70 wherein the neurological disorder is selected from the group consisting of amyotrophic lateral sclerosis (ALS), and frontotemporal lobar degeneration (FTLD)(e.g., frontotemporal dementia (FTD)).

Embodiment Q72: The method of embodiment Q70 or Q71 wherein the toxic protein is selected from the group consisting of toxic TDP-43, toxic SOD1 and toxic FUS/TLS.

Embodiment Q73: The method of embodiment Q70 wherein the neurological disorder is selected from the group consisting of Parkinson's disease (PD), Alzheimer's Disease (AD), Huntington's disease (HD), Creutzfeldt-Jakob disease (CJD), variant Creutzfeldt-Jakob disease (vCJD) and Amyotrophic Lateral Sclerosis (ALS).

Embodiment Q74: The method of embodiment Q70 or Q73 wherein the toxic protein is selected from the group consisting of α-synuclein, β-amyloid Huntingtin protein (HTT), Glutamate, prion proteins, e.g., inflammatory proteins such as cytokines, interleukines, tumor necrosis factors, other potentially harmful proteins and bacteria, viruses and other pathogens.

Embodiment Q75: The method of embodiment Q70 wherein the neurological disorder is a tauopathy selected from Progressive supranuclear palsy (PSP), Alzheimer's disease (AD), Parkinson's disease (PD), Primary age-related tauopathy (PART), chronic traumatic encephalopathy (CTE), corticobasal degeneration (CBD) or corticobasal ganglionic degeneration (CBGD), frontotemporal dementia with parkinsonism linked to chromosome 17 (FTDP-17), Lytico-bodig disease, ganglioglioma, meningioangiomatosis, post-encephalitic Parkinsonism and subacute-sclerosing panenecephalitis (SSPE).

Embodiment Q76: The method of embodiment Q70 wherein the neurological disorder is progressive supranuclear palsy (PSP).

Embodiment Q77: The method of embodiment Q70 wherein the neurological disorder is frontotemporal lobar degeneration (FTLD)(e.g., frontotemporal dementia (FTD)).

Embodiment Q78: The method of embodiment Q70 wherein the neurological disorder is Alzheimer's disease.

Embodiment Q79: The method of any one of embodiments Q70, Q73 and Q75 to Q78 wherein the toxic protein is a toxic tau protein (e.g., tau protein aggregates, tau protein tangles, tau oligomers, hyperphosphorylated tau proteins, soluble tau proteins, tau dimers).

Embodiment Q80: The method of embodiment Q70 to Q73, wherein the TDP-43, SOD1 or FUS status of a subject is determined by analyzing a biological sample from the subject.

Embodiment Q81: The method of embodiment Q80, wherein the biological sample is a blood sample.

Embodiment Q82: The method of embodiments Q80 or Q81 wherein the biological sample is analyzed for the presence of mutations in the TDP-43, SOD1 or FUS genes.

Embodiment Q83: The method of embodiment Q82 wherein if the subjects status has been determined to be TDP-43, SOD1 or FUS positive, step a) of the method further comprises receiving information regarding the presence of toxic proteins in the CSF of the subject, and if the subject has been determined to have toxic proteins in the CSF, diagnosing the subject to be susceptible to the treatment of step b).

Embodiment Q84: The method of any one of embodiments Q70 to Q83 wherein the agent is an enzyme.

Embodiment Q85: The method of embodiment Q84 wherein the enzyme is a protease.

Embodiment Q86: The method of embodiment Q85 wherein the protease is able to reduce the concentration of toxic protein (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) in the CSF by 20% or more (e.g., by 30% or more, by 40% or more, by 50% or more, by 60% or more, by 70% or more, by 80% or more, by 90% or more, by 95% or more, by 99% or more) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment Q87: The method of embodiment Q85 or Q86 wherein the protease can reduce the concentration of toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) below 1000 ng/mL (e.g., below 100 ng/mL, below 10 ng/mL, below 2.5 ng/mL, below 2 ng/mL, below 1.5 ng/mL, below 1 ng/mL, below 0.5 ng/mL, below 0.25 ng/mL, below 0.1 ng/mL, below 0.05 ng/mL, below 0.025 ng/mL, below 0.01 ng/mL, below 0.005 ng/mL, below 0.0025 ng/mL, below 0.001 ng/mL) in less than a month (e.g., in less than a week, in less than a day, in less than 12 hours, in less than 6 hours, in less than 60 minutes, in less than 30 minutes, in less than 20 minutes, in less than 10 minutes, in less than 5 minutes, in less than 2 minutes).

Embodiment Q88: The method any one of embodiments Q85 to Q87 wherein the protease is characterized by an active site capable of selectively recognizing the peptide sequence of the toxic protein (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) over other proteins normally occurring in the CSF and is further capable of specific cleavage of at least one peptide bond of the toxic protein over cleavage of peptide bonds of proteins normally occurring in the CSF.

Embodiment Q89: The method of any one of embodiments Q85 to Q88 wherein the protease is capable of effecting the degradation of the toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) without significant effects on the concentration of proteins naturally occurring in the CSF.

Embodiment Q90: The method of any one of embodiments Q85 to Q89 wherein the protease has higher specificity and lower affinity for the toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) compared to proteins normally occurring in the CSF.

Embodiment Q91: The method of any one of embodiments Q85 to Q89 wherein the protease has higher specificity and higher affinity for the toxic (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) compared to proteins normally occurring in the CSF.

Embodiment Q92: The method of any one of embodiments Q85 to Q91 wherein the protease has higher efficiency cleaving at least one peptide bond of the toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) compared to the peptide bonds of proteins normally occurring in the CSF.

Embodiment Q93: The method of any one of embodiments Q85 to Q92 wherein the protease is selected from the group consisting of calpains (e.g., calpain-2), caspases (e.g., caspase-1, caspase-3, caspase-6, caspase-7, caspase-8), granzymes (e.g., granzyme A), trypsin, and meprin alpha.

Embodiment Q94: The method of any one of embodiments Q85 to Q93 wherein the protease is a protease naturally occurring in CSF.

Embodiment Q95: The method of any one of embodiments Q70 to Q94 further comprising a step of removing the CSF from the subject prior to contacting it with the agent and a step of reintroducing the CSF back into the subject after contacting it with the agent.

Embodiment Q96: The method of embodiment Q95 wherein the agent is immobilized (e.g., the agent is a protease immobilized on a solid substrate).

Embodiment Q97: The method of embodiment Q96 wherein the agent (e.g., the protease) is immobilized on a solid support.

Embodiment Q98: The method of embodiment Q97 wherein the solid support is a porous solid support.

Embodiment Q99: The method of embodiment Q97 or Q98 wherein the agent (e.g., the protease) is attached to the solid support by covalent binding.

Embodiment Q100: The method of embodiments Q97 to Q99 wherein the solid support is a cross-linked resin.

Embodiment Q101: The method of embodiment Q100 wherein the cross-linked resin is an agarose resin.

Embodiment Q102: The method of any one of embodiments Q96 to Q98 wherein the agent is immobilized by cross-linking to porous beads or membranes (e.g., the agent is a protease cross-linked to porous beads or membranes).

Embodiment Q103: The method of embodiment Q96 wherein the agent is immobilized by precipitation (e.g., as an amorphous or crystalline precipitate).

Embodiment Q104: The method of embodiment Q103 wherein the precipitated agent is cross-linked (e.g., to form a cross-linked amorphous or crystalline precipitate, e.g., cross-linked protease crystals, e.g., cross-linked amorphous protease precipitate).

Embodiment Q105: The method of embodiment Q96 wherein the agent is lyophilized to form a dry powder and the powder is placed inside a porous coating to form beads.

Embodiment Q106: The method of any one of embodiments Q95 to Q105 further comprising a step of filtering the CSF prior to reintroducing the CSF back into the subject.

Embodiment Q107: The method of any one of embodiments Q70 to Q94 wherein the agent is directly introduced into the CSF of the subject.

Embodiment Q108: The method of any one of embodiments Q70 to Q87 and Q93 to Q107 wherein the protease is not selective for the degradation of toxic proteins (e.g., toxic TDP-43 protein, e.g., toxic SOD1 protein, e.g., toxic FUS/TLS protein, e.g., a toxic tau protein (e.g., tau protein aggregates, tau protein tangles, tau oligomers, hyperphosphorylated tau proteins, soluble tau proteins, tau dimers), e.g., α-synuclein, e.g., β-amyloid, e.g., Huntingtin protein (HTT), e.g., glutamate, e.g., prion proteins, e.g., inflammatory proteins such as cytokines, interleukines, tumor necrosis factors, e.g., other potentially harmful proteins and bacteria, viruses and other pathogens) over other proteins normally occurring in the CSF.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. In the cases where elements are presented as lists, e.g., in Markush group format, each subgroup of the elements is also considered to be disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

The entire disclosure of the issued patents, published patent applications, journal articles, and other publications, referred to herein is incorporated by reference. If the information in the incorporated references conflicts with the instant specification, the specification shall control. Any particular embodiment of the present invention that falls within the prior art may be explicitly excluded from any one or more of the claims. As such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating amyotrophic lateral sclerosis (ALS) or frontotemporal dementia (FTD) in a subject, the method comprising:

contacting the cerebrospinal fluid (CSF) of said subject with trypsin immobilized on an agarose substrate at a concentration of 1-10 milligrams per milliliter, wherein said CSF comprises TDP-43 and said contacting removes TDP-43 from said CSF, thereby treating said subject wherein trypsin is immobilized on an agarose substrate in the form of a concentration gradient of 1-10 milligrams per milliliter of trypsin.

2. The method of claim 1, further comprising the step of detecting said TDP-43 from the CSF of the subject.

3. The method of claim 2, wherein the step of detection is conducted prior to the step of contacting, thereby identifying the subject as suitable for the treatment.

4. The method of claim 1, wherein said contacting comprises contacting the CSF of a subject in need thereof in situ.

5. A method of treating amyotrophic lateral sclerosis (ALS) or frontotemporal dementia (FTD) in a subject, the method comprising:

contacting the cerebrospinal fluid (CSF) of said subject with elastase immobilized on an agarose substrate at a concentration of 1-10 milligrams per milliliter, wherein said CSF comprises TDP-43 and said contacting removes TDP-43 from said CSF, thereby treating said subject wherein elastase is immobilized on an agarose substrate in the form of a concentration gradient of 1-10 milligrams per milliliter of elastase.

6. The method of claim 5, wherein said contacting comprises contacting the CSF of a subject in need thereof in situ.

7. The method of claim 5, further comprising the step of detecting said TDP-43 from the CSF of the subject.

8. The method of claim 7, wherein the step of detection is conducted prior to the step of contacting, thereby identifying the subject as suitable for the treatment.

* * * * *